United States Patent
Hayworth et al.

(10) Patent No.: US 10,288,532 B2
(45) Date of Patent: May 14, 2019

(54) METHODS, APPARATUSES AND SYSTEMS FOR COLLECTION OF TISSUE SECTIONS

(71) Applicant: President and Fellows of Harvard College, Cambridge, MA (US)

(72) Inventors: Kenneth Jeffrey Hayworth, Ashburn, VA (US); Richard Schalek, Wakefield, MA (US); Juan Carlos Tapia, Bronx, NY (US); Narayanan Kasthuri, Cambridge, MA (US); Jeff Lichtman, Cambridge, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/670,784

(22) Filed: Aug. 7, 2017

(65) Prior Publication Data

US 2018/0080856 A1 Mar. 22, 2018

Related U.S. Application Data

(63) Continuation of application No. 13/821,028, filed as application No. PCT/US2011/050704 on Sep. 7, 2011, now Pat. No. 9,784,648.

(Continued)

(51) Int. Cl.
| | | |
|---|---|---|
| *G01N 1/06* | (2006.01) | |
| *A61B 16/00* | (2006.01) | |
| *G01N 35/00* | (2006.01) | |

(52) U.S. Cl.
CPC ............... *G01N 1/06* (2013.01); *A61B 16/00* (2013.01); *G01N 35/00009* (2013.01);
(Continued)

(58) Field of Classification Search
CPC ............... G01N 1/06; G01N 2001/065; G01N 2001/066
See application file for complete search history.

(56) References Cited

U.S. PATENT DOCUMENTS

| | | |
|---|---|---|
| 2,822,726 A | 2/1958 | Blum |
| 3,540,335 A | 11/1970 | Sitte |
| (Continued) | | |

FOREIGN PATENT DOCUMENTS

| | | |
|---|---|---|
| DE | 3500596 A1 | 7/1986 |
| WO | WO 91/02960 A1 | 3/1991 |
| (Continued) | | |

OTHER PUBLICATIONS

International Search Report and Written Opinion dated Apr. 23, 2012 for International Application No. PCT/US2011/050704.

(Continued)

*Primary Examiner* — Paul M. West
(74) *Attorney, Agent, or Firm* — Wolf, Greenfield & Sacks, P.C.

(57) ABSTRACT

Methods, apparatuses and systems for facilitating automated or semi-automated collection of tissue samples cut by a microtome. In one example, a collection apparatus may be moved back and forth between respective positions at which the collection apparatus is operatively coupled to a microtome so as to collect cut tissue samples, or routine access to the microtome is provided. Relatively easy movement and positioning of the collection apparatus is facilitated, while at the same time ensuring structural stability and appropriate alignment and/or isolation between the collection apparatus and the microtome. A fluid reservoir receives samples cut by the microtome, and the collection apparatus may collect samples via a conveyor-like substrate disposed near/in the reservoir. A linear movement of the substrate may be controlled based on a cutting rate of the microtome, and the fluid (Continued)

level in the reservoir may be automatically maintained to facilitate effective sample collection.

15 Claims, 33 Drawing Sheets

Related U.S. Application Data

(60) Provisional application No. 61/393,185, filed on Oct. 14, 2010, provisional application No. 61/380,484, filed on Sep. 7, 2010.

(52) U.S. Cl.
CPC . *G01N 2001/061* (2013.01); *G01N 2001/065* (2013.01); *G01N 2001/066* (2013.01); *G01N 2001/068* (2013.01)

(56) References Cited

U.S. PATENT DOCUMENTS

| | | | |
|---|---|---|---|
| 3,733,948 A * | 5/1973 | Pickett | G01N 1/06 134/191 |
| 3,845,659 A | 11/1974 | Wikefeldt et al. | |
| 3,939,019 A | 2/1976 | Pickett | |
| 4,272,049 A | 6/1981 | Kindel | |
| 4,545,831 A | 10/1985 | Ornstein | |
| 4,577,516 A | 3/1986 | Wyser | |
| 4,588,119 A | 5/1986 | Fernandez-Acebal | |
| 4,752,347 A | 6/1988 | Rada | |
| 4,914,022 A | 4/1990 | Furmanski et al. | |
| 5,282,404 A | 2/1994 | Leighton et al. | |
| 5,451,500 A | 9/1995 | Stapleton | |
| 5,533,342 A | 7/1996 | Gordon | |
| 5,713,255 A | 2/1998 | Izvozichikov et al. | |
| 5,746,855 A | 5/1998 | Bolles | |
| 5,974,923 A | 11/1999 | Rigby et al. | |
| 6,253,653 B1 | 7/2001 | Walter et al. | |
| 6,330,348 B1 | 12/2001 | Kerschmann et al. | |
| 6,387,653 B1 | 5/2002 | Voneiff et al. | |
| 6,634,268 B1 | 10/2003 | Guenther et al. | |
| 7,152,493 B2 | 12/2006 | Otsuka | |
| 7,374,907 B1 | 5/2008 | Voneiff et al. | |
| 7,677,289 B2 | 3/2010 | Hayworth et al. | |
| 8,366,857 B2 | 2/2013 | Hayworth et al. | |
| 9,304,067 B2 | 4/2016 | Hayworth et al. | |
| 9,784,648 B2 | 10/2017 | Hayworth et al. | |
| 9,927,327 B2 | 3/2018 | Hayworth et al. | |
| 2003/0022271 A1 | 1/2003 | Voneiff et al. | |
| 2003/0094571 A1 | 5/2003 | Lykken et al. | |
| 2005/0173632 A1 | 8/2005 | Behar et al. | |
| 2006/0008790 A1 | 1/2006 | Hayworth et al. | |
| 2008/0101666 A1 | 5/2008 | Hunt | |
| 2009/0087904 A1 | 4/2009 | Heid et al. | |
| 2010/0093022 A1 | 4/2010 | Hayworth et al. | |
| 2010/0323445 A1 | 12/2010 | Hayworth et al. | |
| 2011/0215081 A1 | 9/2011 | Beer | |
| 2013/0216451 A1 | 8/2013 | Hayworth et al. | |
| 2014/0026683 A1 | 1/2014 | Hayworth et al. | |
| 2016/0139007 A1 | 5/2016 | Hayworth et al. | |

FOREIGN PATENT DOCUMENTS

| | | |
|---|---|---|
| WO | WO 2008/066846 A2 | 6/2008 |
| WO | WO 00/62035 A1 | 10/2009 |

OTHER PUBLICATIONS

International Preliminary Report on Patentability dated Mar. 21, 2013 for International Application No. PCT/US2011/050704.
Partial Supplementary European Search Report for Application No. 11824074.6 dated Jan. 9, 2018.
Extended Search Report dated May 2, 2018 in connection with European Application No. 11824074.6.
[No Author Listed], Lathe. Dictionary.com. http://dictionary.reference.com/browse/lathe [last accessed Apr. 6, 2009]. 1 page.
Briggman et al., Towards Neural Circuit Reconstruction with Volume Electron Microscopy Techniques. Curr Opin Neurobiol. Oct. 2006;16(5):562-70.
Denk et al., Serial Block-Face Scanning Electron Microscopy to Reconstruct Three-Dimensional Tissue Nanostructure. PLoS Biol. Nov. 2004;2(1):1900-9.
Harris et al., Uniform Serial Sectioning for Transmission Electron Microscopy. J Neurosci. Nov. 2006;26(47):12101-3.
Hayworth et al, Automating the Collection of Ultrathin Serial Sections for Large Volume TEM Reconstructions. Microscopy Microanal. Aug. 2006;12(2):86-7.

* cited by examiner

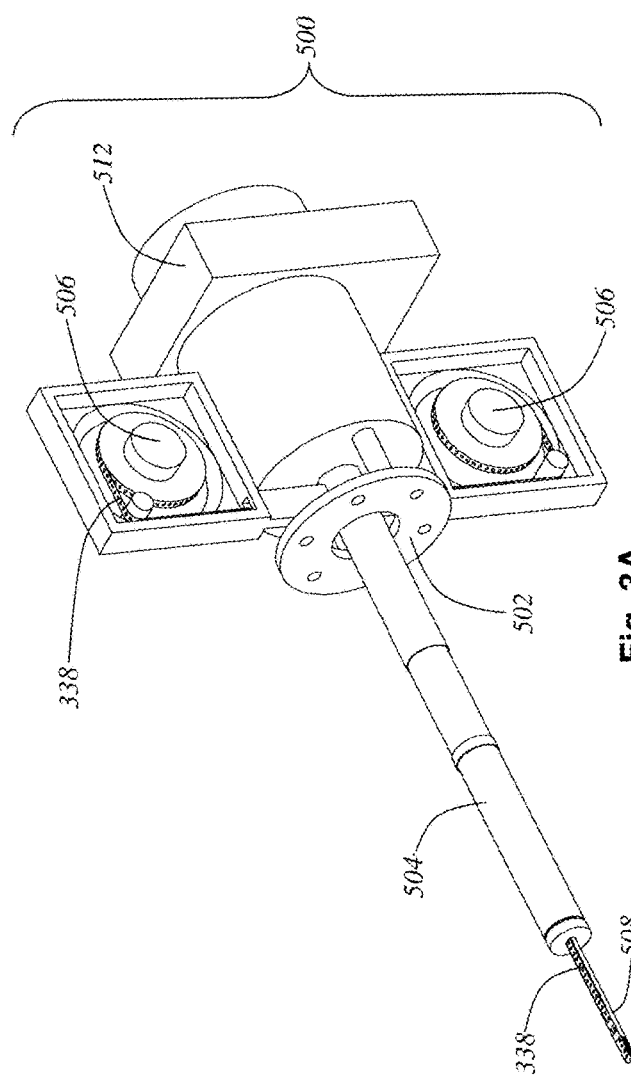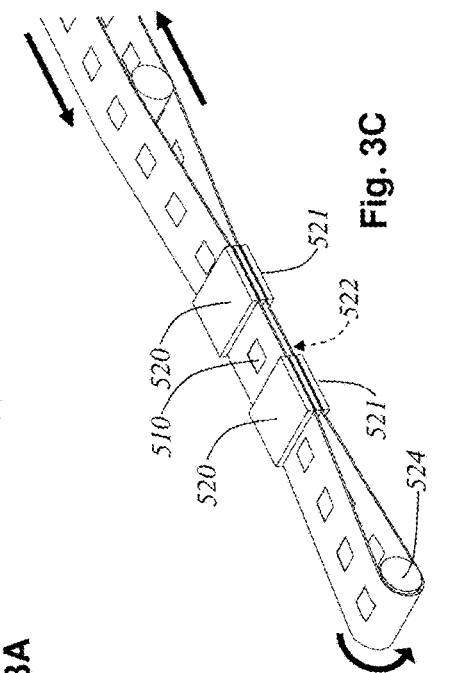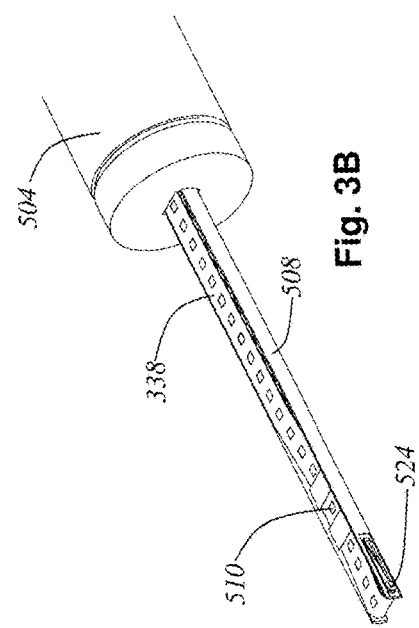

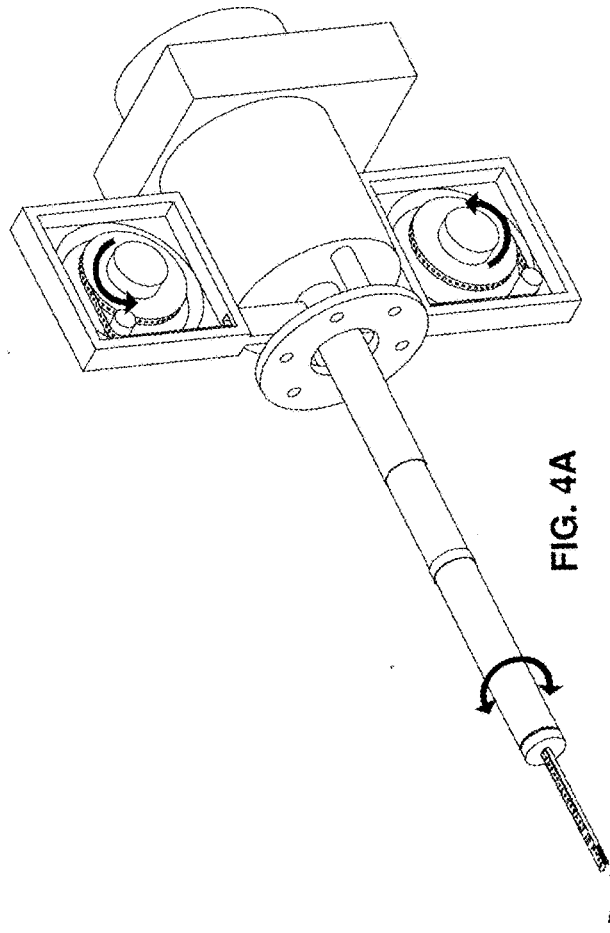
FIG. 4A
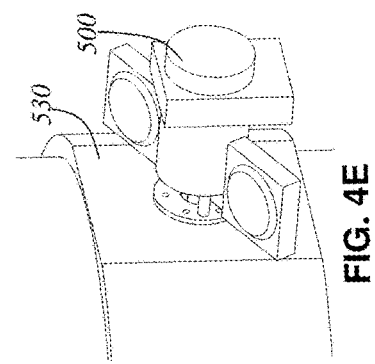
FIG. 4E
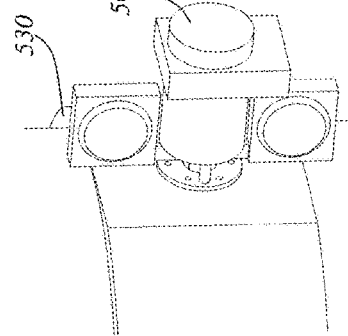
FIG. 4D
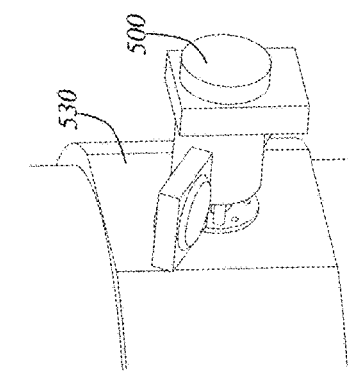
FIG. 4C
FIG. 4B

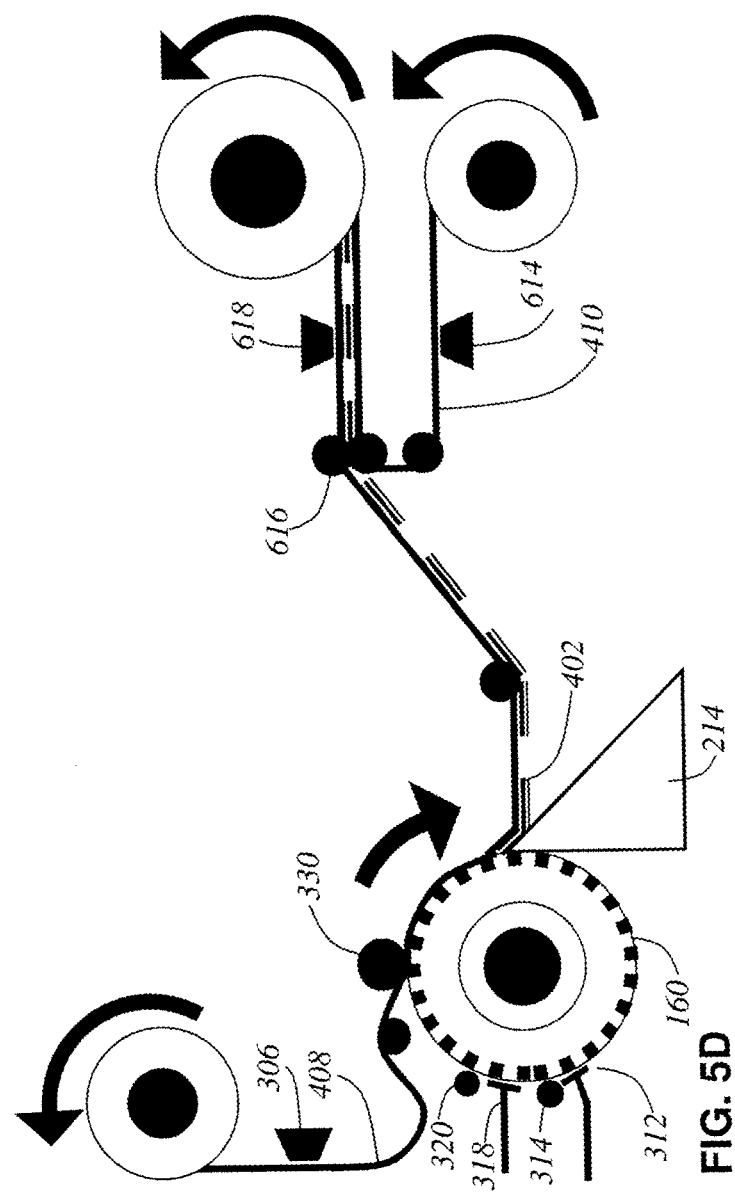

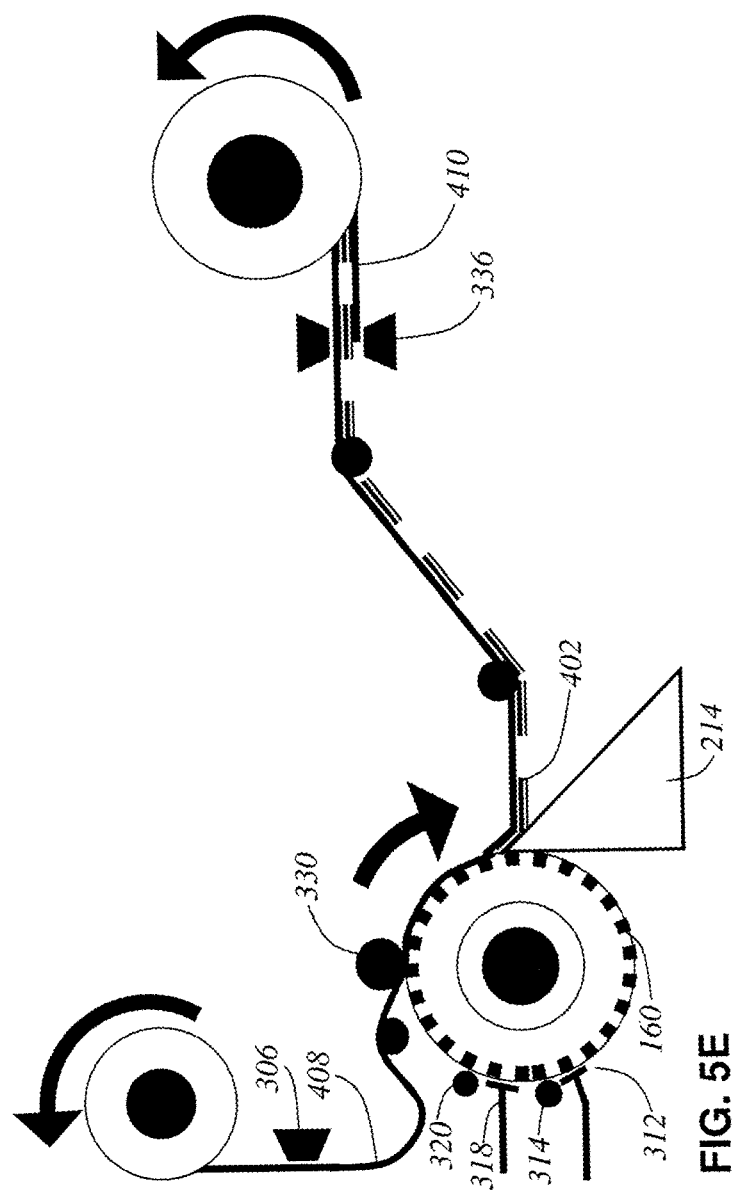

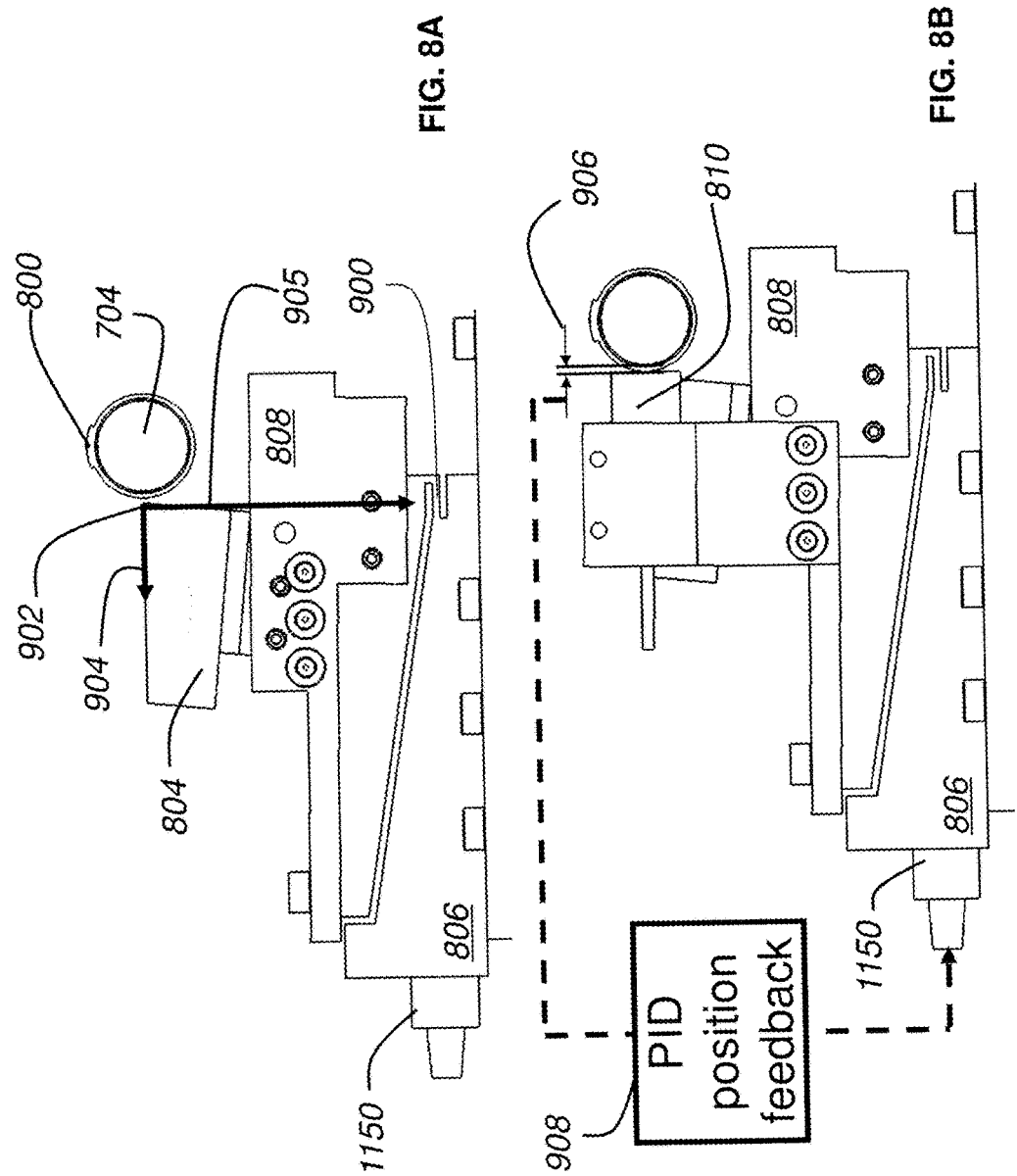

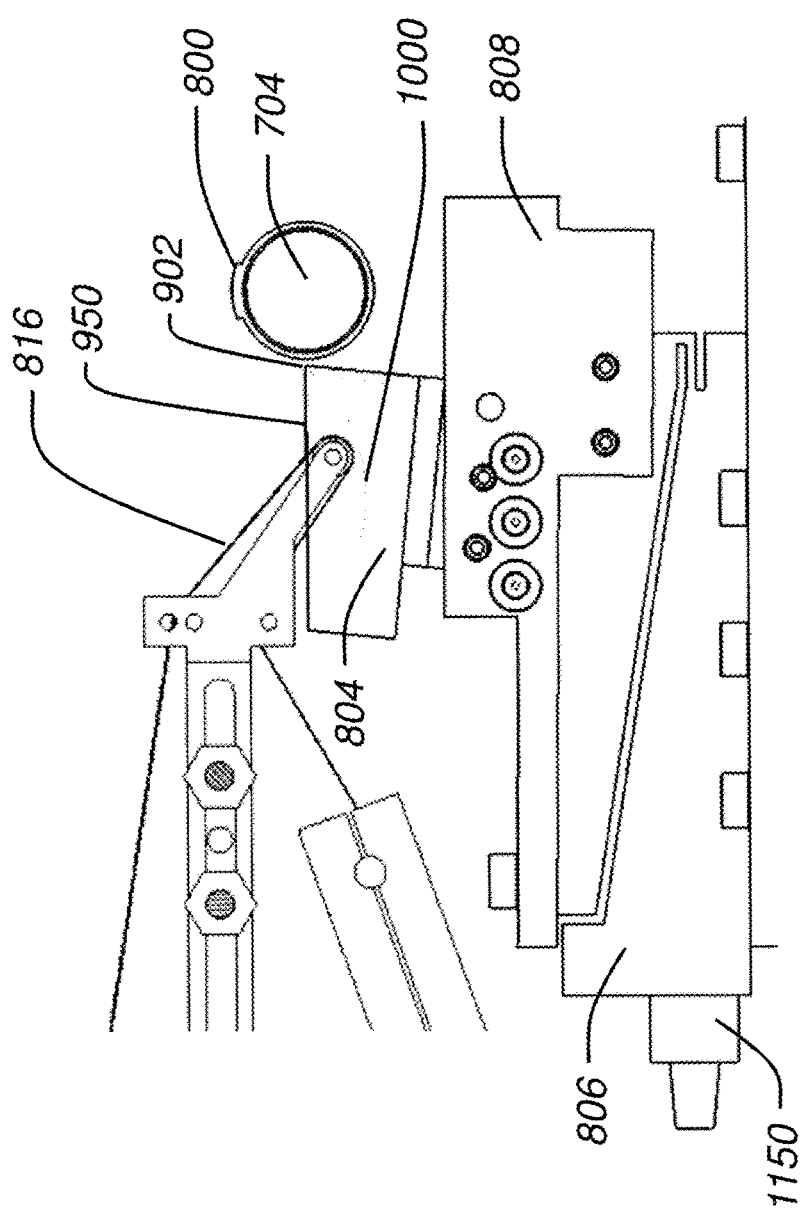

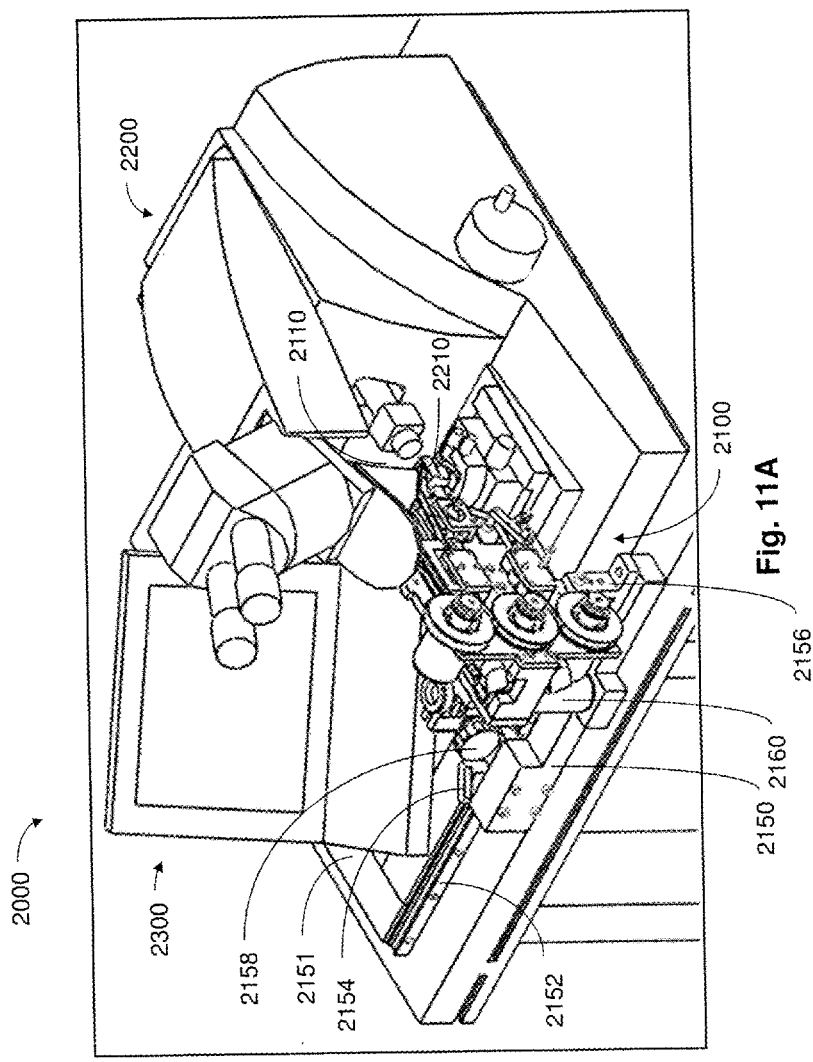

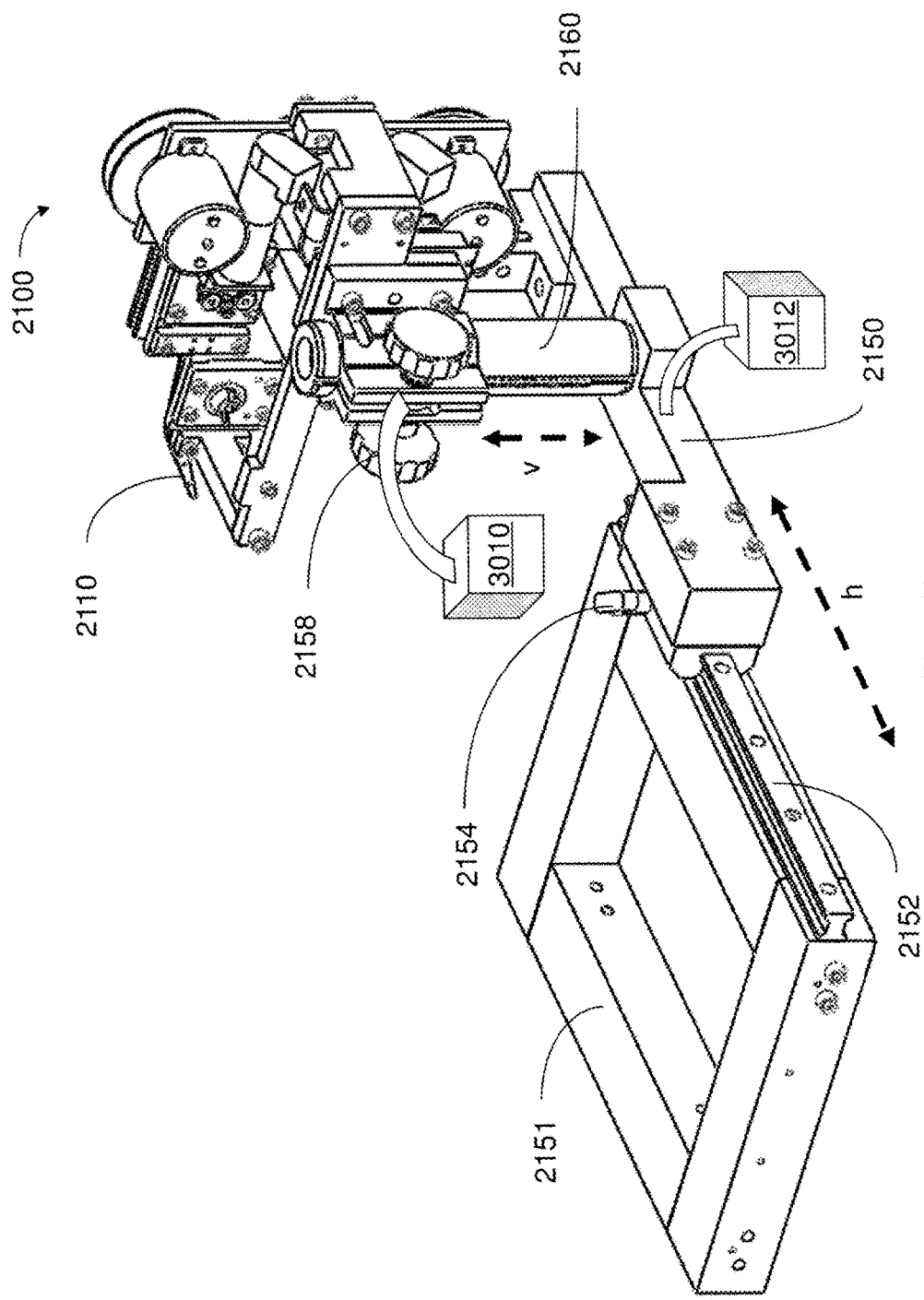

METHODS, APPARATUSES AND SYSTEMS FOR COLLECTION OF TISSUE SECTIONS

RELATED APPLICATIONS

This application is a continuation of U.S. patent application Ser. No. 13/821,028 which is a national stage filing under 35 U.S.C. § 371 of international PCT application PCT/US2011/050704, filed Sep. 7, 2011, which claims priority to U.S. Provisional Application No. 61/393,185 filed Oct. 14, 2010, entitled "Methods, Apparatuses and Systems for Collection of Tissue Sections" and to U.S. Provisional Application No. 61/380,484 filed Sep. 7, 2010, entitled "Automatic Tape-Collection Mechanism for Ultramicrotomes," the entire contents of each being incorporated herein by reference.

GOVERNMENT FUNDING

This invention was made with government support under 1P50MH094271, 5R01NS020364, 5RC2NS069407 awarded by the National Institutes of Health. The U.S. government has certain rights in the invention.

DESCRIPTION OF RELATED ART

Today neuroscientists are routinely carrying out increasingly advanced physiological experiments and cognitive scientists are proposing and testing increasingly comprehensive models of brain function. Such experiments and models involve brain systems where incomplete information regarding the system's underlying neural circuitry presents one of the largest barriers to research success. It is widely accepted within the neuroscience community that what is needed is a comprehensive and reliable wiring diagram of the brain that will provide a neuroanatomical scaffolding (and a set of foundational constraints) for the rest of experimental and theoretical work in the neuro- and cognitive sciences. The current approach of attempting to integrate thousands of individual in vivo tracing experiments into a coherent whole has been considered to be a virtually impossible task.

There is an alternative approach that avoids the problem of stitching together the results of thousands of in vivo tracer injection experiments. The imaging of a single post-mortem brain at a sufficiently high resolution to resolve individual neuronal processes and synapses, while maintaining registration across size-scales, would allow direct tracing of a brain's connectivity. Researchers using the raw data in such a synapse-resolution brain connectivity atlas would be able to map all the regions, axonal pathways, and synaptic circuits of the brain; and unlike separate specialized experiments, the results would immediately and easily be integrated because they are all performed on the same physical brain.

The creation of such a synapse-resolution atlas has been achieved for tiny invertebrate animals such as *C. Elegans* (a round worm measuring 1 mm in length and less than 100 um in diameter). The fundamental technology used, that of serial section electron reconstruction, currently requires the painstaking manual production of thousands of extremely thin (<1 μm) tissue slices using a standard ultramicrotome in which newly sliced tissue sections are floated away from the cutting knife on water and manually placed on slotted TEM specimen grids a few sections at a time.

Because of the manual nature of this current process, this technique is impractical to apply to larger brain structures and so it is currently unable to address the needs of the larger community of neuroscientists who require a map of the brain connectivity of rodent and primate brains. Extending these manual tissue imaging technologies to map structures that are $1 \times 10^5$ (mouse brain) and $1 \times 10^8$ (human brain) times as large as *C. Elegans* presents a significant challenge.

There are a number of patents pertaining to microtomes and their automation. However, these designs are targeted toward automating the slicing process only, and do not address the tissue collection and handling processes. Today the term "automated microtome" has become synonymous with a manual microtome merely having motorized knife advance. Thus, current conventional "automated microtome" designs still require manual slice retrieval and manual slide or grid mounting for imaging.

A tissue sample sectioned by an ultramicrotome typically results in fragile strips of tissue that come off the ultramicrotome knife and float on a surface of water contained within a knife boat of the ultramicrotome. The fragile strips of tissue are manually collected onto slot grids for use in transmission electron microscopy (TEM) by employing a highly unreliable and painstaking positioning process. The process involves the use, by a highly trained technician, of an "eyelash" instrument to maneuver the fragile sections onto the slot grid(s). Such manual slice retrieval necessitates that skilled, delicate, and incredibly time-consuming work be expended on each tissue slice (or small series of slices) as it involves "fishing" each tissue slice out of a water boat attached to the knife of the conventional ultramicrotome instrument and onto a TEM grid. Such a collection process drastically limits the total volume of tissue that can be sectioned and imaged. In addition, no matter how experienced and skilled the technician may be at moving tissue strips to the slot grids, manual intervention will inevitably result in damage to at least some of the collected tissue sections. Further, the manual nature of the collecting process also requires continual starting and stopping of the ultramicrotome to allow for the tissue sections to be manually collected, adversely impacting the precision of the cutting process. To compensate for such disturbances, tissue sections are typically cut thicker, thus, limiting the overall resolution of electron microscopy imaging to be performed on the tissue.

SUMMARY

The inventors have recognized and appreciated that automating in some manner a tissue sample collection process (e.g., in connection with slicing thin tissue samples using a conventional ultramicrotome) would mitigate potential damage to samples collected during a manual collection process, and significantly facilitate imaging of greater numbers of collected samples. In these respects, automated tissue sample collection techniques would provide an appreciable advance toward mapping larger tissue structures.

In view of the foregoing, various inventive embodiments disclosed herein relate generally to apparatus, systems and methods for facilitating automated collection of tissue samples that are sliced from a microtome. In one exemplary implementation, a collection apparatus that is placed into coupling engagement with a microtome such that the collection apparatus collects thin tissue sections sliced from the microtome. The collection apparatus may be adapted to move back and forth repeatedly from a position that is suitable for automated and prolonged collection of thin tissue sections. When the collection apparatus is not in an appropriate position for automated and prolonged thin tissue section retrieval, thin tissue sections may be collected from the microtome according to routine methods (e.g., the eyelash method).

Systems and methods described also relate to automatically maintaining fluid contained in a reservoir of the microtome at a level suitable for automated and prolonged collection of thin tissue sections. In some cases, a current level of fluid within the reservoir is monitored with respect to an edge of a microtome-quality knife. When the current level of fluid within the reservoir drops below an operating level suitable for automated and prolonged thin tissue section collection, fluid is automatically introduced into the reservoir to restore the current level of fluid within the reservoir to the suitable operating level. A computing device having a processor may be subject to feedback control and used in conjunction with a fluid input apparatus to appropriately maintain fluid levels in the reservoir to be suitable for automatic and prolonged retrieval of thin tissue sections, for example, on to a support substrate.

During operation of the collection apparatus to retrieve thin tissue sections from the microtome, a computing device having a processor may be used in conjunction with appropriate monitoring equipment, to monitor the rate at which a tissue sample is sliced by the microtome knife. According to the rate at which thin tissue sections are produced, the speed of a support substrate moving along the collection apparatus may be controlled for appropriate collection of thin tissue sections on to the support substrate.

In an illustrative embodiment, a device for processing a tissue sample is provided. The device includes a collection apparatus for collecting at least one thin tissue section provided from a microtome, wherein the collection apparatus is constructed and arranged to move back and forth in a repeated motion between a collecting position and a non-collecting position relative to the microtome.

In another illustrative embodiment, a system for processing a tissue sample is provided. The system includes a microtome adapted to slice at least one thin tissue section from a tissue sample; and a collection apparatus for collecting the at least one thin tissue section from the microtome, wherein the collection apparatus is constructed and arranged to move back and forth repeatedly between a collecting position and a non-collecting position relative to the microtome.

In a different illustrative embodiment, a method for processing a tissue sample is provided. The method includes causing movement of a collection apparatus from a non-collecting position to a collecting position relative to a microtome; operating the collection apparatus to collect at least one thin tissue section produced from the microtome; and causing movement of the collection apparatus from the collecting position to the non-collecting position relative to the microtome.

In yet another illustrative embodiment, a system for processing a tissue sample is provided. The system includes a microtome having a reservoir containing fluid automatically maintained at a substantially constant level within the reservoir, the microtome adapted to slice at least one thin tissue section from a tissue sample such that the at least one thin tissue section contacts the fluid within the reservoir; and a collection apparatus for collecting the at least one thin tissue section from the fluid within the reservoir.

In a further illustrative embodiment, a method for using a microtome including slicing a tissue sample with a microtome-quality knife to produce at least one thin tissue section, and bringing the at least one thin tissue section into contact with a fluid within the reservoir of the microtome. The method includes monitoring a current level of fluid within the reservoir with respect to an edge of the microtome-quality knife; and automatically restoring the current level of fluid within the reservoir to an operating level of fluid when the current level of fluid within the reservoir is less than the operating level of fluid.

In another illustrative embodiment, a non-transitory computer-readable storage medium having computer-executable instructions adapted to perform, when executed, steps for controlling hardware coupled to the computer-readable storage medium for processing a tissue sample. The steps include monitoring a rate of slicing of the tissue sample with a microtome-quality knife in producing a plurality of thin tissue sections; and controlling a speed of a support substrate moving on a collection apparatus in accordance with the rate of slicing of the tissue sample to collect the plurality of thin tissue sections on to the support substrate.

In a different illustrative embodiment, a non-transitory computer-readable storage medium having computer-executable instructions adapted to perform, when executed, steps for controlling hardware coupled to the computer-readable storage medium for maintaining a level of fluid in a reservoir. The steps include monitoring a current level of fluid within the reservoir with respect to an edge of the microtome-quality knife; and automatically restoring the current level of fluid within the reservoir to an operating level of fluid when the current level of fluid within the reservoir is less than the operating level of fluid.

The foregoing is a non-limiting summary of the invention, which is defined by the attached claims. Other aspects, embodiments, features will become apparent from the following description.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The accompanying drawings are not intended to be drawn to scale. In the drawings, each identical or nearly identical component that is illustrated in various figures is represented by a like descriptor. For purposes of clarity, not every component may be labeled in every drawing.

The advantages and features of this invention will be more clearly appreciated from the following detailed description, when taken in conjunction with the accompanying drawings.

FIG. 3A is a perspective view showing an electron tomography tape cassette with side panels removed to reveal tissue tape reels disposed within;

FIG. 3B is a close-up view of a specimen stage tip of the electron tomography tape cassette of FIG. 3A;

FIG. 3C is a close-up view of the specimen stage tip of the electron tomography tape cassette of FIG. 3A where the sides of the tip have been removed to reveal the tape path and clamping mechanism within;

FIG. 4A is a perspective view of an electron tomography tape cassette with arrows drawn to display the main degrees of freedom of movement allowed by the mechanism;

FIG. 4B depicts a stylized transmission electron microscope (TEM) with the electron tomography tape cassette of FIG. 4A inserted into its specimen port;

FIGS. 4C, 4D, and 4E are three close-up views of the electron tomography tape cassette of FIG. 4A detailing how the entire cassette mechanism can rotate relative to the TEM in order to perform a tomographic tilt-series on the tissue sample at the tip;

FIG. 5D is a schematic side view of yet another embodiment;

FIG. 5E is a schematic side view of a different embodiment;

FIG. 8A is a side plan view of a nanosectioning lathe ultramicrotome without some sensors according to an embodiment of the present invention;

FIG. 8B is a side plan view of a nanosectioning lathe ultramicrotome with a sensor and PID feedback mechanism according to an embodiment of the present invention;

FIG. 9A is a side plan view of a nanosectioning lathe ultramicrotome with a conveyor belt mechanism according to an embodiment of the present invention;

FIG. 11A is a perspective view of a system for processing tissue samples in accordance with embodiments described;

FIG. 12 is a perspective view of portions of a system for processing tissue samples in accordance with embodiments described;

DETAILED DESCRIPTION

Figure 1B:
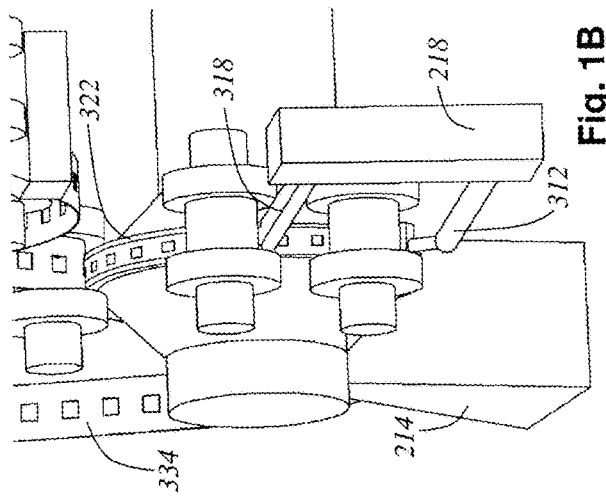
FIG. 1B is a close-up view of the back of the tissue block of FIG. 1A, including blockface applicator mechanisms.

It should be understood that aspects of the invention are described herein with reference to the figures, which show illustrative embodiments in accordance with aspects of the invention. The illustrative embodiments described herein are not necessarily intended to show all aspects of the invention, but rather are used to describe a few illustrative embodiments. Thus, aspects of the invention are not intended to be construed narrowly in view of the illustrative embodiments. It should be appreciated, then, that the various concepts and embodiments introduced above and those discussed in greater detail below may be implemented in any of numerous ways, as the disclosed concepts and embodiments are not limited to any particular manner of implementation. In addition, it should be understood that aspects of the invention may be used alone or in any suitable combination with other aspects of the invention.

I. Overview

Various embodiments disclosed herein relate generally to automated collection of tissue samples (also referred to herein as "thin tissue sections") cut from a microtome. In some exemplary implementations, collection apparatuses and associated methods may be employed with various types of conventional microtomes, wherein the microtome is unmodified and the collection apparatuses and methods are configured as an add-on or retrofit to be used in conjunction with the microtome to facilitate automated tissue sample collection. In other implementations, some modifications may be made to a conventional microtome to facilitate integration with automated sample collection apparatuses and methods according to the inventive concepts described herein. In yet other implementations, an integrated system is contemplated including a microtome comprising various inventive features disclosed herein relating to automated sample collection features, and/or a microtome (either conventional or modified) that is operatively coupled to an automated sample collection apparatus.

For example, in some embodiments, collection apparatuses may be positioned in a coupled arrangement with any appropriate microtome where thin tissue sections cut from the microtome can be automatically collected on to a support substrate for long periods of time and without added user intervention. When not positioned in a coupled arrangement with a microtome in a manner that supports automatic retrieval of thin tissue sections for long time periods, collection apparatuses described may be disposed in a position apart from the microtome so as not to interfere with the ability for a user to perform standard microtome activities (e.g., performing block trimming, setting the position of the knife, initial microtome sectioning, eyelash method collection of tissue sections, etc.).

In the foregoing embodiment, when automatic and prolonged collection of tissue sections from the microtome is desired, the collection apparatus may be moved toward and into coupled engagement with the microtome. In exemplary implementations, the collection apparatus may be constructed and arranged to facilitate relatively easy movement and positioning of the collection apparatus by a user (e.g., technician/operator) into and out of coupled engagement with a microtome, while at the same time ensuring structural stability and appropriate alignment and/or isolation of the collection apparatus. In other implementations, movement and positioning of the collection apparatus into and out of coupled engagement with a microtome may be accomplished automatically or semi-automatically (e.g., without significant user intervention).

In one aspect, when a collection apparatus is disposed in a suitable collecting position, thin tissue sections produced from the microtome may be automatically collected on to a suitable support substrate without user intervention. In some cases, even when the collection apparatus is coupled with the microtome in a collecting position, a microtome user may still have access to certain functions of the microtome (e.g., usage of control panel, hand wheel, stereo microscope, water boat access, etc.).

For instances when manual collection of tissue sections is desired, the collection apparatus may be appropriately moved away from and out of engagement with the microtome, providing space for the operator to perform manual collection. Accordingly, a collection apparatus may be caused to move back and forth repeatedly between a collecting position and a non-collecting position relative to the microtome. Such movement between collecting and non-collecting positions may be effected manually through user intervention, or alternatively, movement of the collection apparatus may occur automatically through actuation via a control device.

It should be appreciated that collection apparatuses described are not limited to the type of microtome the collection apparatus may be placed in coupled arrangement with, and may be suitable for use with any appropriate microtome. For example, collection apparatuses described may be appropriately coupled to any microtome known in the art, such as and without limitation, rotary microtomes, lathe microtomes, ultramicrotomes, sled microtomes, vibrating microtomes and laser microtomes. Although aspects of the invention are not so limited, embodiments of collection apparatuses coupled with lathe microtomes and ultramicrotomes are described in further detail below.

Apparatuses, systems and methods described herein also may provide for fluid contained in a reservoir of a microtome to be automatically maintained at a level suitable for producing thin tissue sections and to support automated collection of the thin tissue sections in a reliable and prolonged manner. For example, during automated collection, the current level of fluid within the reservoir may be monitored and a determination made as to whether the current level of fluid is within an operating level suitable for reliably slicing a tissue sample to produce and continuously collect thin tissue sections on to a support substrate. In an embodiment, if the current level of fluid is below a threshold of the operating level required for automatic and continuous operation of the collection apparatus for prolonged periods of time (e.g., more than 30 minutes), then additional fluid is automatically introduced into the reservoir (e.g., via a fluid input apparatus coupled to the reservoir) for restoring the current fluid level to a suitable operating level.

Aspects of a microtome and/or collection apparatus may be controlled through executable instructions suitably encoded on to a computing device electrically coupled to the microtome and/or the collection apparatus. In certain embodiments, appropriate software instructions are encoded on to a computing device coupled to the microtome through appropriate hardware so as to control the level of fluid within the reservoir of the microtome to be appropriately maintained for continuous and automatic operation of the microtome and collection of thin tissue sections. Automated collection of thin tissue sections may occur for prolonged periods of time (e.g., more than 30 minutes, more than 12 hours, several days, etc.).

In some embodiments, appropriate executable instructions are encoded on to a computing device in a system coupled with a microtome and a collection apparatus for monitoring a rate at which a tissue sample is sliced to produce thin tissue sections. Based on the rate of thin tissue section production, the system controls the speed of movement of the support substrate on the collection apparatus to match the rate of sectioning so as to automatically collect thin tissue sections in an orderly fashion. In certain embodiments, executable instructions encoded on to a computing device in a system coupled to a collection apparatus provide for monitoring of the tension of a support substrate on the collection apparatus and controlling the tension of the support substrate so as to automatically and continuously collect thin tissue sections in a suitable manner.

The collection apparatus may have a conveyor portion at least partially submerged in fluid contained within a reservoir and in close proximity to the edge of a microtome knife. Tissue sections that slide off a surface of the knife float on the surface of the fluid and are retrieved by a moving support substrate on the conveyor portion. In one embodiment, the support substrate is controlled so as to move at a speed matching the speed of microtome slicing so that each section is gently pulled off the fluid surface and laid flat on to the substrate surface, without bunching or layering together of the tissue sections. In some embodiments, automatic collection is permitted without user intervention for more than twelve hours, thereby facilitating collection of thousands of sections between 10 and 50 nm thick (e.g., approximately 30 nm thick).

Systems that involve methods for automatic collection of thin tissue sections produced from a microtome are disclosed in U.S. Patent Publication No. 2010/0093022 entitled "Methods and Apparatuses for Providing and Processing Sliced Thin Tissue"; U.S. Pat. No. 7,677,289 entitled "Methods and Apparatuses for the Automated Production, Collection, Handling, and Imaging of Large Numbers of Serial Tissue Sections"; and U.S. Provisional Application No. 60/867,487, filed Nov. 28, 2006, entitled "Methods and Apparatus for Providing and Processing Serial Tissue Sections" all of which are incorporated herein by reference in their entirety. Accordingly, a large volume of thin tissue sections may be automatically collected on to a support substrate and imaged at nanometer resolution, for example, by electron microscopy such as TEM and/or scanning electron microscopy (SEM). Following below is a description of exemplary systems according to the above-identified references to provide appropriate context for collection apparatuses and methods, and integrated systems of collection apparatuses and microtomes, described in greater detail herein.

II. Exemplary Methods, Apparatuses and Systems Based on Integrated Systems

The above-identified references relate generally to an automatic tape collecting lathe ultramicrotome (ATLUM), in which the basic cutting motion of the microtome is redesigned, replacing the conventional discontinuous ratcheting motion with a continuous rotary motion of a lathe. In other aspects, irrespective of cutting based on lathe-like continuous rotary motion or discontinuous ratcheting motion, other aspects of the above-identified references relate to the production of tissue samples and appropriate mounting of samples on substrates to facilitate various imaging techniques involving electron microscopy and, in particular, scanning electron microscopy (SEM). It should be appreciated that automated collection apparatuses, systems and methods described in greater detail below may be based on or incorporate several concepts relating to an ATLUM and/or production of tissue samples suitable for imaging based on electron microscopy; at the same time, it should be understood that collection apparatuses, systems and methods described herein are not limited to application with an ATLUM or particular techniques for preparing collected samples for imaging.

In an ATLUM, a block of tissue sample having various geometries may be sliced into a continuous ribbon of thin tissue, or multiple thin tissue sections, and disposed on an appropriate substrate to facilitate subsequent imaging of the sliced thin tissue. A continuous lathe cutting design may provide for continuous taping and slice collection. A mechanically stable, reliable, fast, and easily constructed design may result, facilitating fully automated production, collection, handling, imaging, and storage of thousands of semi-thin and ultra-thin tissue sections.

Closed-loop control of section thickness of thin tissue sections or ribbons sliced from a tissue sample may be implemented to produce thinner sliced tissue sections or ribbons having tightly controlled thickness. Thinner samples with predictable thickness in turn facilitate high quality volume reconstructions of biological samples. In one exemplary implementation, one or more capacitive sensors are employed in an ATLUM to facilitate regulation of a distance between a slicing knife and a tissue sample to be sliced, thereby controlling sliced tissue thickness with improved precision. Other types of distance sensing techniques may be employed in other implementations to control and regulate sliced tissue thickness.

Thin tissue sections or ribbons may be particularly processed/prepared to facilitate imaging with a scanning electron microscope (SEM) (e.g., in electron backscatter mode). Imaging via a SEM is generally a significantly simplified process as compared to imaging via a TEM (transmission electron microsope), and images may be obtained via SEM of sufficient quality, and in many instances equivalent quality, to conventional TEM images. Collected tapes of thin tissue sections or ribbons sliced from a tissue sample are used to create UltraThin Section Libraries (UTSLs) that allow for fully automated, time-efficient imaging in the SEM.

Accordingly, thinner tissue sections having tightly controlled thickness may be produced in a fully automated fashion. In exemplary applications, tens of meters of ultrathin sections may be automatically sliced and collected on a tape that is subsequently stained with heavy metals and mounted onto plates for any appropriate imaging mode in a scanning electron microscope (SEM), such as, but not limited to, electron backscatter imaging. Sections retrieved by automated collection systems described herein may provide images equivalent to TEM images, showing detail down to individual synaptic vesicles within synapses. Automated collection systems can also quickly create a UTSL of many cubic millimeters of tissue, enough to encompass multiple brain regions and their interconnecting axonal tracts. The UTSL can also be swiftly SEM imaged, and this can be used to intelligently direct subsequent time intensive high-resolution imaging forays. In this manner, researchers may efficiently map out specific neural circuits spanning several millimeters with a resolution in the nanometer range.

Figure 1C:
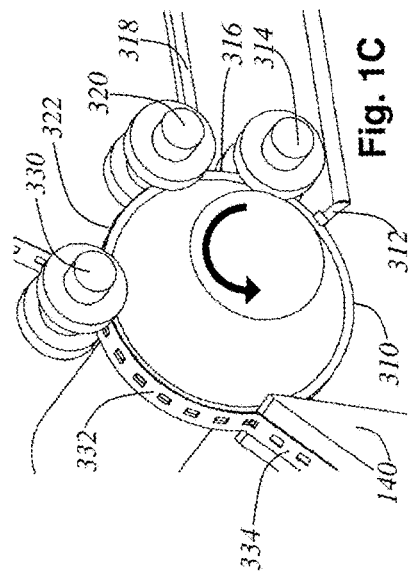
FIG. 1C is a close-up view of the side of the tissue block of FIG. 1A during operation of an automatic taping lathe-microtome.
Figure 1A:
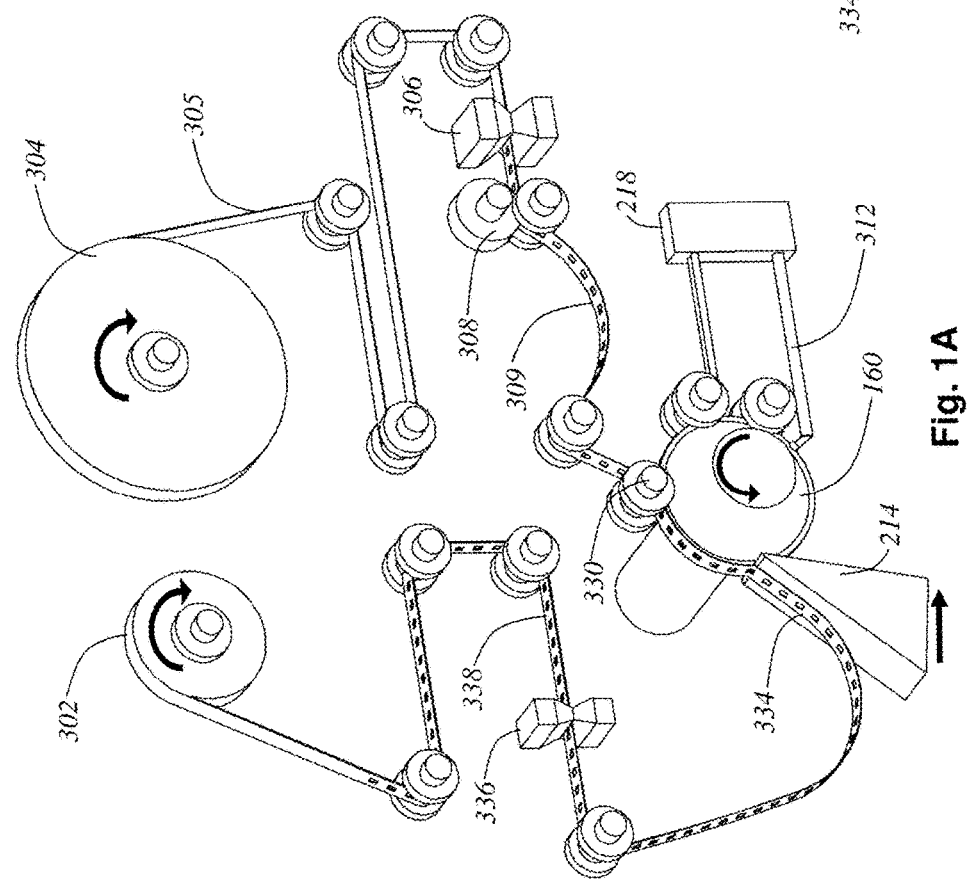
FIG. 1A is a perspective view of a tape-collecting mechanism and cylindrical tissue block.

A general discussion of suitable methods for collecting thin tissue sections cut from a microtome will now be provided in accordance with a number of illustrative examples. FIG. 1A is a perspective view detailing the tape-web mechanism 300 and cylindrical tissue block 160 only. The lathe body and cross-slide components have been removed for clarity. FIG. 1B shows the same mechanism, but a close-up view from behind the tissue block detailing the blockface application mechanism. FIG. 1C is a close-up view of the side of the tissue block during operation.

Starting at the top of the mechanism, a top base tape feed roll 304 supplies a continuous stream of plastic tape 305 into the mechanism. A tape hole puncher mechanism 306 punches square viewing holes into the plastic top base tape 305. The tape is driven forward by tape drive rollers 308 which maintain a slack (no tension) region 309 in the web. This slack region assures that no tension forces from the tape disturb the motion of the cylindrical tissue block 160 or the blockface taping process.

The slack, hole-cut tape 309 is adhered to the block 160's surface at a blockface taping pressure roller 330. The timing of the hole cutting performed by the tape hole puncher mechanism 306 is synchronized to the current angle of the cylindrical tissue block 160 such that each hole will be precisely aligned directly over an embedded tissue cube 140 when the tape 309 is adhered to the block 160. A section 332 of top base tape is adhered for a quarter-turn of the block 160 before it is sliced off the block 160 at the knife 214 along with a thin ribbon 402 (detailed in FIG. 2A) of the tissue block 160. The thickness of this ribbon of tissue is set by the relative rotary speed of the lathe spindle 206 and the linear speed of the knife 214. Both speeds are constant and serve to cut off a continuous spiral ribbon of embedded tissue 402 which is already adhered to the tape 332 at the time of cutting producing a freshly microtomed ribbon of tissue adhered to top base tape 334.

Figure 2B:
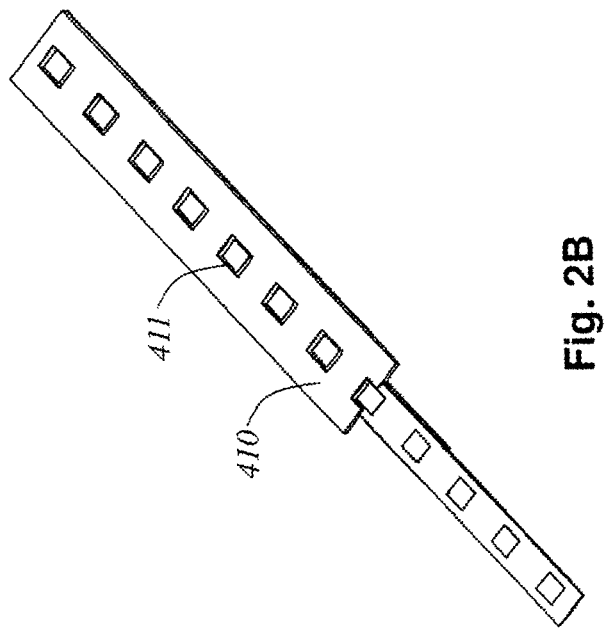
FIG. 2B is a view of a final composite tape sandwich from the underside.
Figure 2A:
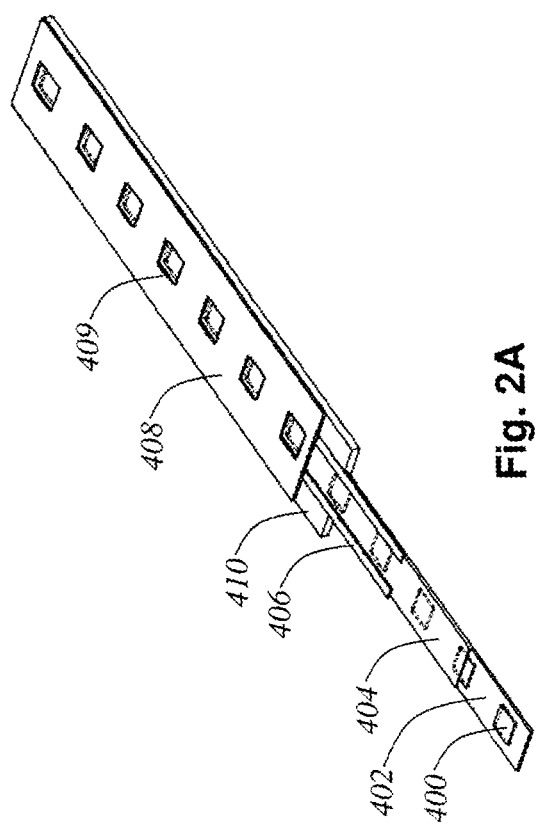
FIG. 2A is a perspective view of a composite tape sandwich, where each layer in the composite sandwich is peeled away and labeled.

The ribbon of tissue adhered to tape 334 is reeled up by a final composite tissue tape-sandwich take-up reel 302, but before it gets there the tape 334 is driven past a bottom base tape applicator (and blowout hole mechanism) 336 that applies (prints) a covering bottom base tape 410 (detailed in FIG. 2A). The blowout hole function of 336 will be discussed later during the section on tape imaging. This produces a TEM-ready composite tape sandwich (abbreviated tissue-tape) 338 which is reeled up onto take-up reel 302.

FIGS. 1B and 1C more clearly show the blockface preparation steps leading up to the production of the adhered section of tape 332. The freshly cut surface of cylindrical tissue block 310 comes into contact with the TEM support film head 312 which lays down a thin-film on the entire surface of the block with the help of a smoothing and drying roller mechanism 314. This produces a support film coated block surface 316. This surface next comes in contact with two adhesive strip applicator heads 318 that, with the help of a smoothing and drying roller mechanism 320, lay down two strips of adhesive on the block face 322. This section of the block's surface with TEM support film and adhesive strips applied is now ready to accept the hole-cut tape 309 for blockface taping via the pressure roller 330.

FIG. 2A shows the composition of the tissue-tape 338. FIG. 2B shows the backside of the tissue-tape. In these figures, each layer in the composite sandwich has been peeled away and labeled. The tissue tape 338 includes a composite tape-sandwich where the microtomed ribbon cut off the tissue block 402 is secured and protected between top 408 and bottom 410 base tapes. A multitude of 1 mm$^2$ microtomed tissue slices 400 (each 100 nm to 1 µm thick) are seen to be embedded in the ribbon 402. Further, this ribbon 402 is covered by a TEM support film coating 404 providing support for each tissue slice 400 across the viewing slots (holes) in tapes 408 and 410 (these holes are labeled 409 in the top tape FIG. 2A, and 411 in the bottom tape FIG. 2B). The adhesive strips 406 laid down by the applicator heads 318 just before blockface taping by pressure roller 330 are seen clearly in FIG. 2A. Notice how these strips avoid obstructing the view of the tissue slices 400 but still provide adherence between the tissue ribbon 402 and the top tape 408.

Seen in the close up view offered by FIG. 2A, one can appreciate the tissue-tape 338's similarity to the film in a movie projector. Each tissue slice 400 resides in its own frame, acting as a TEM slot grid. This analogy to the film in a movie projector can be taken further. In this form, the tissue-tape 338 can be reeled up without damage to the delicate tissue slices 400 since the slices are protected on both sides by the base tapes 408 and 410. These reels of tissue-tape can be handled and stored efficiently, and can be fed into an electron tomography tape cassette 500 (shown in FIG. 3A) for fast random access ultrastructure imaging in a standard commercial TEM.

FIG. 3A shows the electron tomography tape cassette 500. Side panels have been removed to reveal two tissue-tape reels 506. The electron tomography tape cassette 500 is designed to act like a standard TEM specimen stage, and thus can slide into the specimen port of a standard TEM 530 (see FIG. 4B). The main difference between the electron tomography tape cassette and a traditional TEM specimen stage is the addition of a set of tape reels and motors 506 for mounting the tissue tape 338 on, and the addition of internal mechanisms that allow the tissue tape 338 to be fed all the way out to the specimen stage's tip 508 and thus into the TEM's electron beam for ultrastructure imaging of the tissue slice 510 clamped at the stage's tip 508. There is a TEM mounting flange 502 which secures the body of the electron tomography tape cassette 500 to the side of a TEM 530. There is also a cylindrical specimen stage body 504 which slips into the vacuum port on the TEM 530 and forms a tight vacuum seal with it, yet simultaneously allows rotation around the long axis of the cylindrical specimen stage body 504. This rotation allows the incidence angle at which the electron beam impinges upon the tissue slice 510 to be varied by rotating the entire assembly of the cylindrical specimen stage body 504 and the cassette reels and motors 506 relative to the mounting flange 502 (see FIGS. 4C, 4D, and 4E). This rotation of the cylindrical specimen stage body 504 relative to the flange 502 is driven by a drive motor 512. Changing this angle of incidence allows for 3D reconstruction of the tissue slice having better resolution in depth than the slice thickness would allow if only 2D (non-tilt series) imaging were performed, and is a standard technique in electron microscopy today.

FIG. 3B shows a close-up view of the specimen stage tip 508. FIG. 3C is a close-up view of the specimen stage tip 508 where the sides of the tip have been removed to reveal the tape path and clamping mechanism within. The tissue-tape 338 wraps around a pulley 524 at the very front of the tip 508. During operation, the tape drive motors 506 reel the tissue tape 338 such that the tissue slice to be imaged 510 is centered between two top clamps 520 and is thus inline with the TEM's electron beam. These two top clamps 520 then engage, securing that section of tissue-tape containing the slice to be imaged 510 stably in position. The pulley 524's position is then adjusted electronically to lengthen or shorten the section of tape 338 between the top clamps 520 and a pair of bottom clamps 521 in order to bring a blowout hole 522 into position between the two bottom clamps 521. These bottom clamps 521 are then engaged to secure the entire tape 338 for imaging.

This blowout hole 522 is one of a multitude of blowout holes spaced periodically throughout the tape 338. These holes are made within the automatic taping lathe microtome's bottom tape applicator and blowout hole mechanism 336 by simply directing a puff of air at the fragile section of sliced ribbon 402 in periodically spaced frames of the tissue tape 338. Recall that a few tooth-indentation cavities 132 are specifically left empty of tissue cubes 140 during the embedding process for this reason. Thus, the final axle-mounted tissue block 160 had three tissue-free regions 162 around its periphery. These holes 522 are purposely blown out to allow the wrapped around section of the tissue tape 338 which resides between the bottom clamps 521 to not obstruct the imaging of the tissue slice 510 directly above it. The cutaway view of the specimen stage tip 508 in FIG. 3C shows both sets of clamps 520 and 521 engaged securely holding a single slice of tissue 510 in position inline with the TEM's electron beam. Directly below this tissue slice 510 is a blowout hole 522 in the tissue tape 338 and thus only the particular slice to be imaged 510 will be seen by the TEM's electron beam.

FIG. 4A shows the electron tomography tape cassette 500 with arrows drawn to display the main degrees of freedom of movement allowed by the mechanism. The reels of tissue tape 506 can rotate in synchrony to bring any desired slice of tissue in the tape out to the specimen tip and thus into the electron beam for imaging. Exact positioning of the field of view is set by driving the whole tip mechanism along the two degrees of freedom perpendicular to the electron beam's cavity (depicted by arrows shown near tip). Also, the entire cassette and stage body 504 can rotate relative to the TEM mounting flange 502 as described below.

FIG. 4B depicts a stylized transmission electron microscope (TEM) with the electron tomography tape cassette inserted into its specimen port. The tape cassette (with cassette covers, which were removed in previous view, installed) is hermetically sealed and can thus share the TEM's vacuum via its seal along the stage's body 504. The tissue tape 338 within the tape cassette 500 is electronically advanced using reel motors 506 to bring a particular tissue slice 510 to be imaged inline with the TEM's electron beam. Clamps (520 and 521) engage to allow stable unobstructed viewing of the slice 510. Any X-Y motions of the stage are now performed to address a small section within the slice (using standard X-Y specimen stage motors present in the electron tomography tape cassette 500 but, for clarity, not depicted here). A tomographic tilt-series (a set of 121 2D electron micrograph images of the tissue slice 510) can be taken by stepping the incidence angle in 1° increments from −60° to +60°.

In FIGS. 4C, 4D, and 4E the manner in which the body of the electron tomography tape cassette rotates relative to the TEM mounting flange 502 is depicted. Those three figures show the tape cassette mechanism at three different incidence angles (−60°, 0°, and +60° respectively).

At each angle, a 2D electron micrograph is produced and all 121 of these images are fed into a standard electron tomographic volume reconstruction algorithm in order to compute a 3D voxel volume digital image of the particular piece of tissue 510 under examination. The system is designed such that any of the multitude of tissue slices in the tissue-tape 338 loaded into the electron tomography tape cassette 500 can be randomly and automatically accessed for 2D or 3D tomographic imaging (at ultrastructure resolution) without ever cracking the vacuum of the TEM. Thus, this avoids any time-consuming manual intervention in the imaging process.

The following describes some alternative examples for the automatic taping lathe-microtome. The following descriptions of alternative examples of the invention are presented for the purposes of illustration and description. They are not intended to be exhaustive or to limit the invention to the precise form disclosed. Some of these alternative designs involve variations on the blockface taping and tissue collection processes, as depicted in a series of schematic side views in FIGS. 5A through 5D. The previously disclosed example is re-represented in FIG. 5E in this same schematic form to further promote ease of comparison.

Figures 5A, 5B:
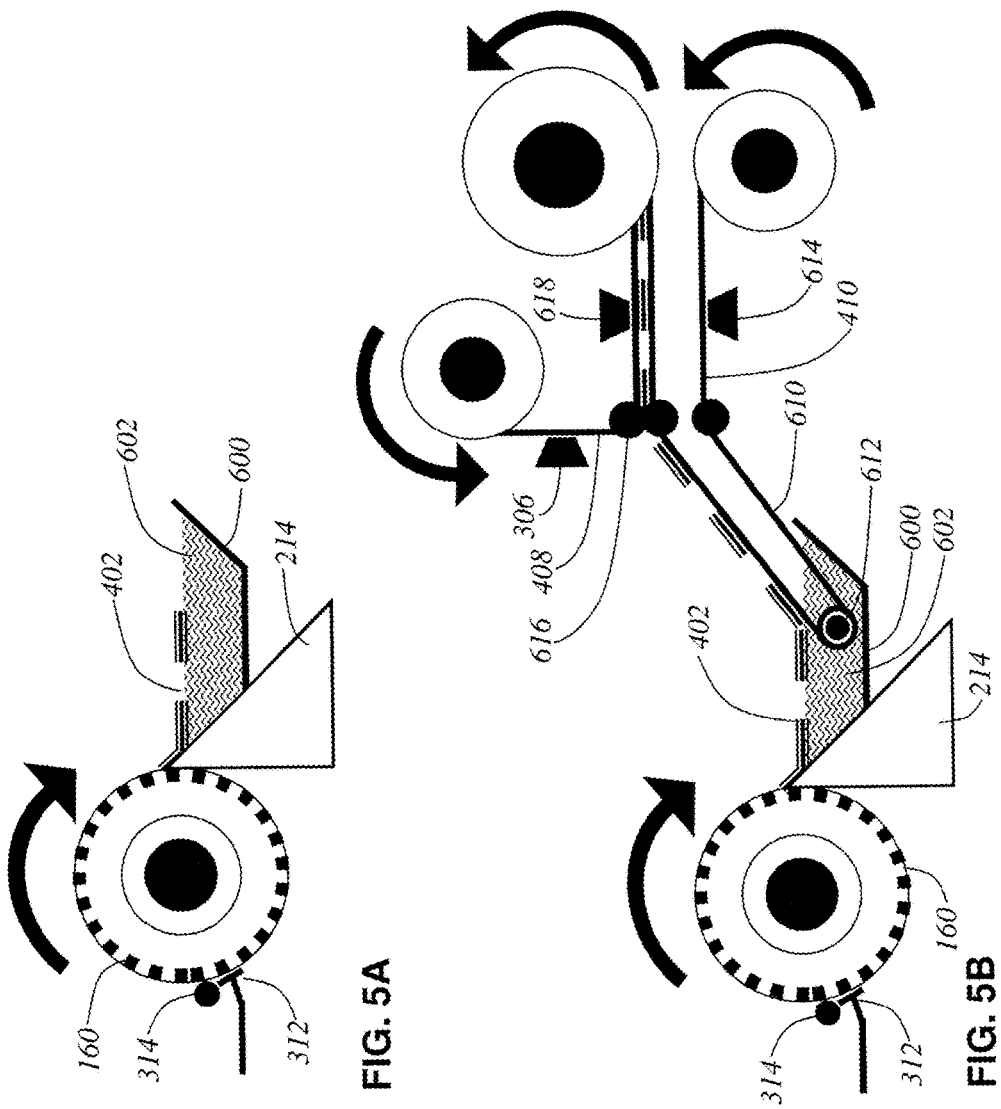
FIG. 5A is a schematic side view of an embodiment.
FIG. 5B is a schematic side view of another embodiment.

FIG. 5A shows a minimalist core design (alternative design #1) of the lathe-microtome. The axle-mounted cylindrical tissue block 160 is rotated against the knife 214 in order to liberate a thin ribbon of tissue slices in embedding medium 402. There is no blockface taping in this design (just thin-film support film deposition by 312 and 314) and so a boat 600 filled with water 602 must be attached to the knife 214 in order to collect the fragile un-taped tissue ribbon 402 as it comes off the knife. In this design, once the tissue ribbon becomes longer than the water boat, manual collection of the tissue ribbon is required, thus this design cannot be considered truly automated.

FIG. 5B show alternative design #2. This is a modification to the minimalist core design in which a submerged conveyor belt 610 is made up of the bottom base tape 410 looped around a pulley 612 firmly attached to the knife's water boat and submerged in its water 602. This arrangement allows the fragile floating tissue ribbon 402 to be gently and continuously lifted out of the water by the conveyor belt 610 as shown in the figure. A bottom base tape hole punching mechanism 614 punches viewing holes in the bottom base tape, and its punches are synchronized with the angle of the tissue block 160 such that each tissue slice 400 in the tissue ribbon 402 resides over a viewing hole. The top tape 408 after having similar viewing holes punched in it by hole puncher 306 is aligned and pressed onto the top of the conveyor belt by pressure roller 616. This produces a tape-sandwich which can be sealed by a sealing mechanism (e.g. a heated pressure roller) 618 before finally being reeled up as a finished TEM-ready tissue tape. This design is fully automated and produces a tissue tape-sandwich capable of automated imaging using the electron tomography tape cassette 500. This design (FIG. 5B) does not employ blockface taping meaning that there is a place in the mechanism where a fragile, freely-floating ribbon of tissue 402 is unsecured by any base tape. This reduces the reliability of the design, but it also reduces its complexity by eliminating blockface taping.

Figure 5C:
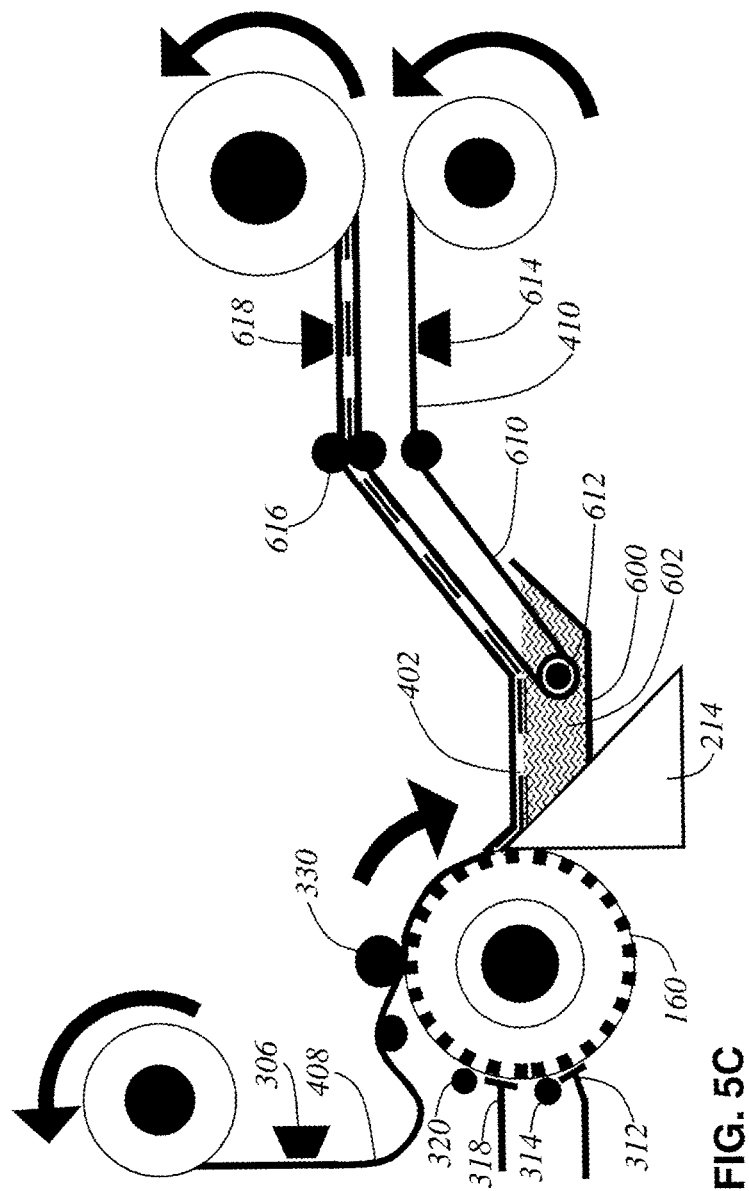
FIG. 5C is a schematic side view of a further embodiment.

FIG. 5C shows alternative design #3 which simply adds blockface taping to the submerged conveyor-belt design. This design is similar to the previously disclosed embodiment's in its use of a blockface taping pressure roller 330 adhering the top base tape 408 directly to the blockface before cutting. In this way there is never a fragile, unsupported tissue ribbon. This design has both the advantage of blockface taping tissue support at the knife and the advantage of a knife water boat to prevent friction-induced damage with the knife. It, however, suffers from the complexity of both a water boat and blockface taping mechanism.

FIG. 5D shows alternative design #4 in which the water boat has been removed and the conveyor-belt formed by the bottom base tape is no longer submerged. The blockface taping has provided enough support for the tissue ribbon 402 coming off the knife 214 such that the water boat support can be eliminated.

Finally, FIG. 5E shows the previously disclosed example in the same schematic manner as the just described alternative designs. In it, the conveyor-belt made up of the bottom tape is replaced by a printing head 336 that manufactures the bottom base tape 410 in situ. This simplifying change can be tolerated if the final tissue tape-sandwich still has sufficient strength provided now only by the top tape. The in situ manufactured bottom tape is then only acting as a relief to protect the tissue from friction damage during reel-up operations.

Another alternative example, which is not depicted in the figures, is to forgo cutting viewing holes in the top and/or bottom base tapes within the microtome, and instead, as a later step, etch these holes using an acid to reveal the tissue slices within. If the top and bottom base tapes are made of a solid material (preferably a metal such as copper) and no holes are cut in the microtome in these tapes, then the composite tape sandwich taken-up on the final take-up reel 302 will not be ready for imaging since the tissue slices between the top and bottom tapes will be hidden by the overlying tapes. This tape-sandwich can then be put through an etching machine where a mask is placed around each section of tape covering up all areas of tape except those having tissue directly beneath. Then the tape is exposed to an etchant (acid in the case of metal tapes) that will dissolve the parts of the top and bottom tape directly above and below each tissue slice. The etchant is chosen so as not to damage the delicate tissue slice which is revealed via the etching process. The advantage of this viewing hole etching method is that it allows the blockface taping step to proceed with a solid tape instead of one with viewing holes. This implies that the tissue slice being cut can be supported across its entire width during the cutting procedure.

Yet another example of the present invention is directed to the production and preparation of "tissue tapes" (one or more thin tissue sections or ribbons disposed on a substrate) that may be imaged with a scanning electron microscope (SEM). As discussed above, various examples of lathe microtomes may be designed to produce tapes for transmission electron microscope (TEM) imaging; however, according to other examples, images may be maintained via an SEM, generally resulting in a significant simplification of the overall process, while obtaining SEM images of sufficient (e.g., equivalent) quality to standard TEM images. In one aspect of this example, tissue tapes prepared and collected via an ATLUM may be used to create UltraThin Section Libraries (UTSLs) that allow for fully automated, time-efficient imaging in the SEM.

In one exemplary TEM implementation described above, the block face was coated continuously with a TEM support film and a metal tape was used to collect the cut sections. This metal tape was later etched with holes to reveal the tissue sections and make them ready for transmission EM imaging. In some instances this may be a complicated process and as such may reduce reliability. In contrast to TEM imaging, in examples directed to producing tissue tapes ready for SEM imaging, the automatic lathe microtome process may be improved in one or more of the following ways: SEM imaging eliminates the need to create viewing holes in the tissue tape (either during the collection process or after the tape is collected); SEM imaging eliminates the need for TEM support film; SEM imaging allows use of a (carbon coated) plastic collection tape such as boPET (biaxially-oriented polyethylene terephthalate) as opposed to metal tape (plastic tapes do not wrinkle, are more dimensionally stable, and are in general better suited to the automatic tape collection mechanism of the lathe microtome); SEM imaging allows the entire tissue tape to be imaged (TEM viewing holes left some parts of the tape obscured), which allows for much larger regions of tissue to be imaged; the resulting tissue tapes for SEM imaging are more robust to handling since the ultrathin sections are adhered directly to the surface of a thick plastic tape (unlike lathe microtomes employing TEM imaging, where these ultrathin sections were supported only at their edges).

In addition to these improvements of the collection process, an automatic lathe microtome configured for SEM imaging creates tissue tapes that can be more efficiently imaged. For example, the tissue tapes can be taken off the lathe microtome and immediately stained with heavy metals and SEM imaged, and no other processing may be required.

More specifically, in one exemplary example directed to SEM imaging, the tissue tape is cut into long strips (at points where there is no tissue), and these strips are mounted onto the surface of a thin metal plate. The protective cover tape (which the automatic lathe microtome adheres to the tissue tape during the collection process) is removed and the plate with sections attached is bathed in heavy metal staining solutions. The resulting "tissue plate" is then mounted in an SEM having a stage with large x-y range (like those designed for semiconductor wafer inspection whose stages can accept large wafers up to 300 mm wide). Any point on the plate's surface (i.e. any section of the collected tissue) can thus be electron backscatter imaged within the SEM at resolutions in the nanometer range.

A set of a few dozen tissue plates would constitute an UltraThin Section Library (UTSL), a permanent repository containing the ultrathin sections of a large volume of brain tissue. For example, with 50 nm sections a set of 100 plates would hold up to 50 cubic millimeters of tissue, any point of which could be imaged at nanometer resolution at any time simply by loading the appropriate plate in the SEM. The automatic lathe microtome can quickly create an UTSL of many cubic millimeters of tissue, enough to encompass multiple brain regions and their interconnecting axonal tracts. The UTSL can then be swiftly SEM imaged at intermediate resolution, and this can be used to intelligently direct subsequent (time intensive) high-resolution imaging forays. In this way a researcher can efficiently map out specific neural circuits spanning many millimeters with a resolution in the nanometer range, a feat impossible with any other imaging technology.

More specifically, in one example, an ATLUM directed to SEM imaging produces a continuous ribbon of thin tissue by lathing an extremely thin strip off the surface of a cylindrical block containing one or a multitude of embedded tissue samples. This continuous ribbon of tissue is simultaneously collected onto a plastic support tape by the taping mechanism of the ATLUM and is subsequently reeled up for later heavy metal staining and SEM backscatter imaging of the ultrathin tissue sections it contains.

An exemplary process according to one example starts by mounting the cylindrical tissue block on a metal axle that is held and rotated by a high-precision rotary stage. A diamond ultramicrotome knife (with attached water boat) is driven forward into the rotating block by means of a high-precision linear stage capable of steps on the order of a few nanometers. By synchronizing the rotational speed of the rotary stage with the advancement speed of the knife, the knife's edge is caused to trace a spiral path through the cylindrical tissue block thus producing a continuous ribbon of tissue of the desired thickness. This process is exactly analogous to a conventional lathe producing a continuous "chip."

The continuous ribbon of tissue produced in this manner comes streaming off of the knife's edge and flows across the surface of the water in the knife's water boat. The automatic lathe microtome uses a conveyor belt (made of specially coated plastic tape) submerged in the water boat to collect this streaming ribbon of tissue. The conveyor belt is driven such that its collection speed is closely matched to the knife's cutting speed. In this way, the ultrathin ribbon of tissue, which is continuously being produced at the knife's edge, floats for a short time across the water of the knife boat and is quickly collected by the conveyor belt of collection tape.

In the ATLUM, the fragile tissue ribbon is always under complete control of the mechanism, being attached at one end to the block (from which it is being produced) and being attached at the other end to the collection tape (submerged conveyor belt) to which it is being permanently attached for later imaging. The continuous nature of the ATLUM's sectioning and collection process in this example, and its constant control of the fragile ribbon, allows the ATLUM to operate with complete autonomy and with high reliability and to produce larger volumes of ultrathin tissue sections than any previous conventional microtome design.

In one aspect of this example, the ATLUM's tape collection mechanism includes a continuous reel-to-reel mechanism containing a plastic film (tape) coated with carbon, as discussed in further detail below. Part of this tape web is submerged in the knife's water boat in order to collect the tissue ribbon on the tape's carbon-coated surface. Immediately after the ribbon is collected on the collection tape an adhesive cover tape is applied for protection during subsequent handling (this cover tape has adhesive on its sides but not along its center, thus it protects the tissue ribbon without actually coming into contact with it). The final "tissue tape" (carbon-coated plastic film, collected tissue ribbon, and cover tape) is reeled up on a final take-up spool. Recall that all aspects of this collection process are continuous and are synchronized with the continuous cutting process.

The plastic film used in one example for preparation of a tissue tape is boPET, which is strong, does not wrinkle as it goes through the mechanism, has an exceptionally smooth surface, and which has a high degree of dimensional stability. The smooth surface is important for later imaging since the tissue ribbon should lie down as flat as possible on the tape. In some exemplary examples directed to SEM imaging, the boPET tape is coated with with a layer of carbon (approximately one micron thick) on the side that will pick up the tissue. This carbon coating does three things: 1) it prevents charging in the SEM by providing an electrically conductive path; 2) it prevents electron beam damage by providing an efficient heat conductor under the tissue; and 3) it provides a highly uniform, low density (low z-number) substrate on which the tissue can rest. Since the tissue may be imaged via SEM using backscattered electrons it is important that the substrate itself generate as little interfering backscatter signal as possible and carbon provides this benefit. In other examples discussed in greater detail below, a polyimide tape such as Kapton® may be employed as a suitable substrate to facilitate SEM imaging.

Once collected, the tissue tape is cut into long strips (at points where there is no tissue), and these strips are mounted onto the surface of a thin metal plate. The protective cover tape is removed and the plate with sections attached is bathed in heavy metal staining solutions. The solutions (typically uranyl acetate and lead citrate) stain selected biological structures within the sections with heavy (high z-number) atoms producing high electron backscatter signals during subsequent SEM imaging. The resulting "tissue plate" is then mounted in an SEM having a stage with large x-y range and a researcher can subsequently use the SEM to image any point on the tissue plate at high resolution.

A single ATLUM run can potentially produce hundreds of meters of tissue tape from a single biological sample a few tens of cubic millimeters in volume. This extremely long tape can then be used to produce a set of approximately 100 tissue plates. In this way the original biological sample has been reduced to an "UltraThin Section Library" (UTSL). This concept of a UTSL is important to understanding the usefulness of the automatic lathe microtome to researchers. For example, with 50 nm thick sections a set of 100 plates would hold up to 50 cubic millimeters of tissue, any point of which could be imaged at approximately 5 nm in plane resolution at any time simply by loading the appropriate plate into the SEM. At this resolution this UTSL would potentially represent 40,000 terabytes of imaging data. This is an almost unimaginable amount of data to store and process and the SEM imaging time required to image the entire UTSL is on the order of centuries. However, the UTSL itself is quite compact (just one hundred plates) and any point within this massive data set can be imaged at will by simply loading (e.g., manually or robotically) the corresponding tissue plate into an SEM.

The ability to efficiently direct nanometer resolution imaging anywhere within a volume of many cubic millimeters of biological tissue is what neuroscience researchers require to map the circuits of the brain. A typical neural circuit includes several interconnected neurons each sending long thin axonal processes many millimeters into separate brain regions. These axonal processes subsequently branch out and make synaptic contacts within these regions that can only be seen with nanometer resolution imaging. Thus neuroscientists are faced with the significant challenge of producing nanometer resolution volume images of large volumes. The UTSL allows just that. The neuroscientist researcher can produce a UTSL containing the brain regions and connecting axonal pathways they wish to study. The researcher can then intelligently direct the SEM to image just those regions within the massive volume that are needed to trace out the circuit of interest. Since the UTSL is a permanent repository of this neural volume, this or another researcher could easily follow-up on the original circuit study by tracing additional branches of the very same neurons. In this way a single UTSL could allow a whole set of collaborative circuits mapping studies over a series of years, potentially revealing the complicated web of neural circuits the brain uses to perceive, remember, reason about, and purposefully act upon the world.

Another example of the present invention is directed to closed-loop feedback control in an ATLUM to regulate thickness of thin tissue sections or ribbons sliced from a block or bulk tissue sample. As described above, conventional microtomes typically move a tissue block along a linear path past a knife edge to produce a section, and then retract the knife during a reset phase in preparation for the next section. For a lathe microtome, operation may be more continuous without need for knife retraction. A tissue block may be mounted on an axle which may be rotated such that the tissue traces a circular path around the rotational axis in close proximity to an advancing knife. As the tissue block moves along its circular path, it may intersect the knife edge, allowing a section to be sliced off in the process. In various examples of the ATLUM design, sectioning performance may be improved, along with allowing thinner sectioning below 40 nm thick with greater reliability and uniformity. The tissue sample to be sectioned may be embedded in and/or around a smooth axle and mounted on a rotary stage of the ATLUM. Capacitive sensors may be used to precisely measure the distance between the knife edge and the axle surface. This distance measurement may be fed back to the knife stage via, but not limited to, an analog PID controller which endeavors to maintain a target distance from the knife edge to the axle surface. In this manner, variable forces encountered at the knife edge during sectioning that would normally produce section thickness variations may be compensated in real time via closed-loop feedback control.

When attempting to cut very thin sections, it is advantageous to reduce section thickness variations where possible. For example, if a user were attempting to section at 40 nm thickness and a variability of +/−20 nm exists in the knife edge position relative to the block, then one may cut 20 nm too thick on a part of the Nth section and 20 nm too thin on the (N+1)th section. These two errors would combine to reduce a part of the (N+1)th section to zero thickness, leading to a break. Such breaks, if they occur often enough, may be problematic for automatic collection of sections.

To address the foregoing, according to one example of the present invention one or more capacitive sensors mounted to the knife stage and positioned so as to effectively measuring the distance from the knife edge to the rotating steel axle containing the tissue block may allow for the knife edge to be stabilized during sectioning to vary significantly less than +/−20 nm. In some examples, knife edge stabilization may occur during sectioning such that section thickness variations are less than +/−10 nm. In further examples, knife edge stabilization may occur during sectioning such that section thickness variations are less than +/−5 nm. In even more examples, knife edge stabilization may occur during sectioning such that section thickness variations are less than +/−1 nm. Once section thickness variation is suitably limited, reliable sectioning may occur to thicknesses less than 40 nm and lengths greater than 5 mm. From aspects presented herein, collection of hundreds of large area sections at thicknesses at or below 50 nm may occur for large volume electron microscopic reconstructions of brain tissue.

Figure 6A:
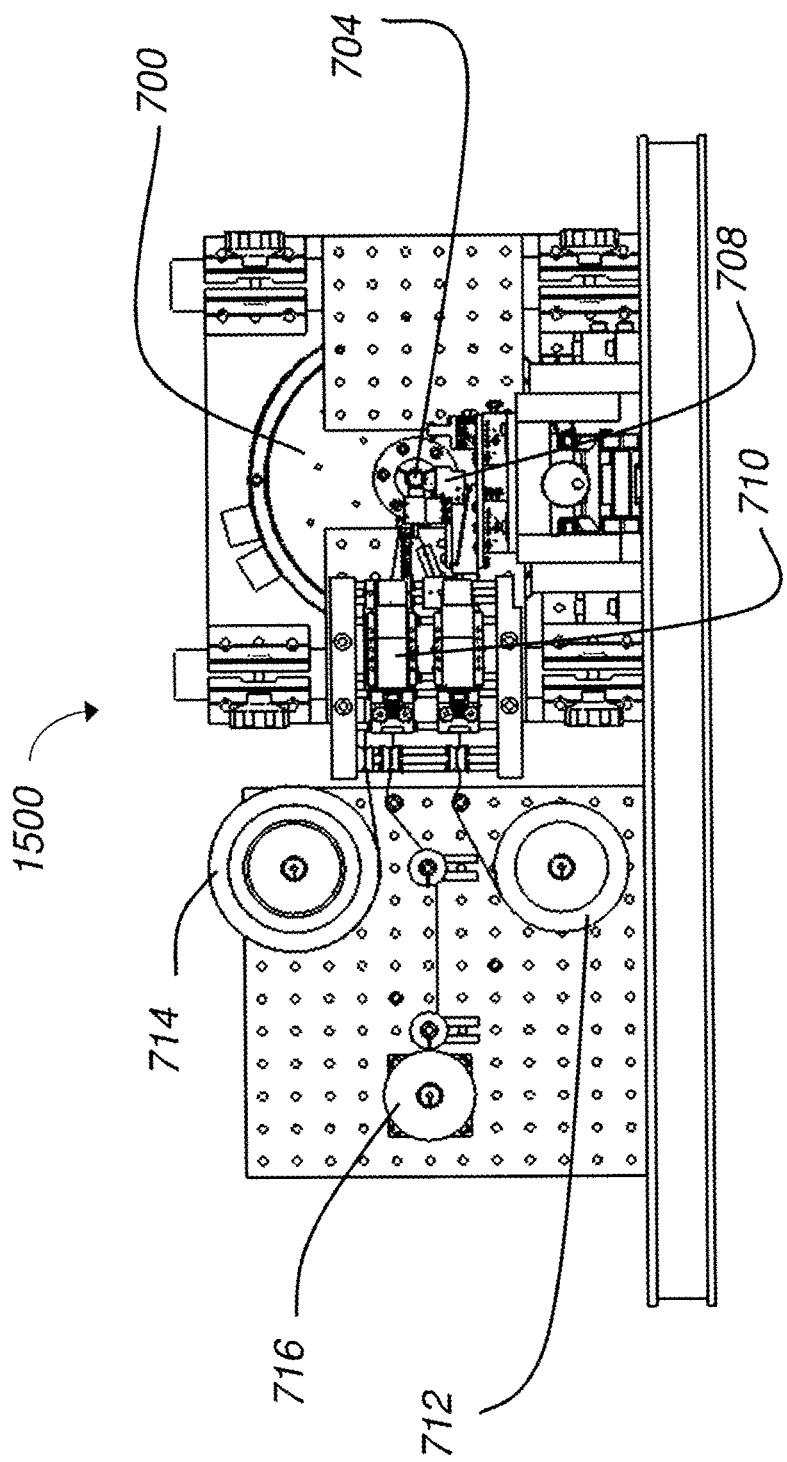
FIG. 6A is a front plan view of a nanosectioning lathe ultramicrotome according to an embodiment of the present invention.
Figure 6B:
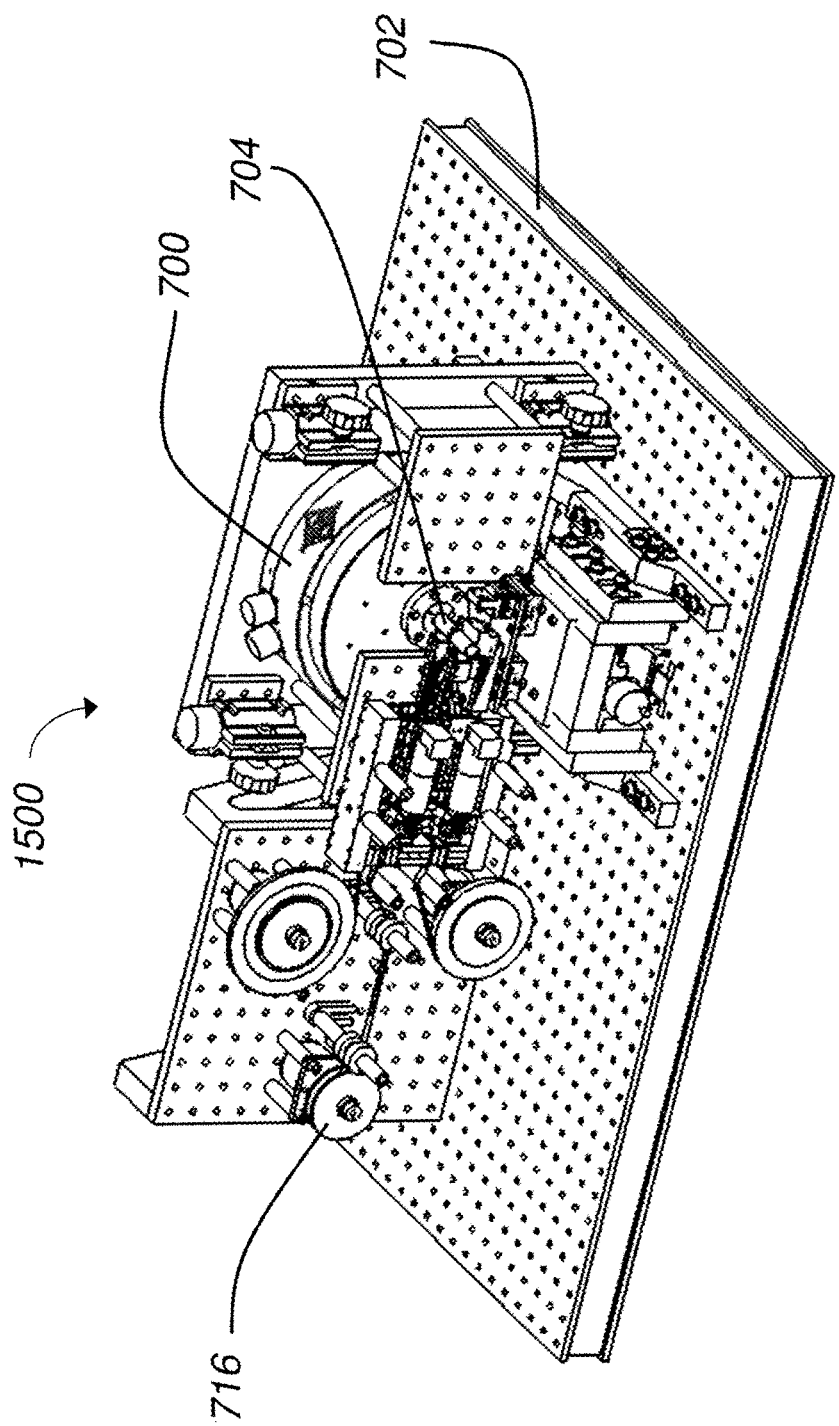
FIG. 6B is a perspective view of a nanosectioning lathe ultramicrotome according to an embodiment of the present invention.

Various aspects of an ATLUM configured with closed-loop feedback control of sliced tissue thickness based on a capacitive sensing technique are discussed in further detail below. For example, FIG. 6A shows a front plan view of an ATLUM 1500 and FIG. 6B shows a perspective view of the same ATLUM 1500 according to one example of the present invention in which closed-loop feedback control is implemented. In the figures, an air bearing rotary stage 700 may be securely mounted to an optical table 702 floated on air for vibration isolation. A steel axle 704 with a tissue sample may be mounted in the rotary stage 700 via a collet chuck. In some examples, the steel axle 704 may have a 0.5 inch diameter. In other examples, the steel axle 704 may have a diameter greater than 1 inch. A diamond knife stage 708 allows for the rotating block of tissue sample to be sectioned or sliced upon contact with a knife edge, and a conveyor belt collection mechanism 710 allows these sections to be automatically collected on a substrate (or "support film") supplied by feed reel 712 to form a "tissue tape." This tissue tape may be temporarily sealed with a protective top tape supplied by feed reel 714, and the assembly of substrate, sliced thin tissue, and protective top tape may be collected on the final take up reel 716. After completion of a run, tape collected of ultrathin sections may be stained with heavy metals and imaged in a SEM using an electron backscatter signal, as discussed above, to produce high-quality, high-resolution images of the tissue's ultrastructure (e.g., sufficient for mapping the synaptic connectivity of brain tissue). It should be understood that in the example shown, any suitable type of thin tissue section(s) or ribbon(s) may be produced. Tissue samples may be prepared for slicing in any appropriate manner as well, such as through embedding, as described previously. In various examples, a tissue sample may be mounted on a rotatable axle 704 for slicing by placing a round block that contains tissue to be sectioned around the axle 704. In further examples, a tissue sample may be mounted on a rotatable axle 704 for slicing by placing a block of any shape into a receiving portion of the axle 704 which may be rotated such that the top of the block may be appropriately sliced by the knife edge with each revolution of the rotatable axle 704. As discussed further below, the tissue samples mounted to the axle 704 may be cylindrical in nature, or have wedge-like geometries.

In one example, the substrate supplied by feed reel 712 may exhibit qualities that enable the thin tissue sections mounted thereon to be imaged effectively using SEM techniques. In SEM, several high-voltage electrons (~10 kV) in an incident imaging beam typically pass through the thinly sliced tissue and interact with the substrate/support film underneath the tissue. If the support film degrades due to excessive electron exposure during imaging, the tissue above it will likely degrade also. In this regard, one salient characteristic of a substrate suitable for use in SEM imaging of thinly sliced tissue includes resistance to bombardment with radiation and/or electrons. Another salient characteristic of a substrate suitable for use in SEM imaging of tissue sections includes a relatively high resistance to heat. In this respect, an exemplary suitable substrate has a high melting point relative to local temperatures found during SEM imaging and/or the ability to conduct heat so that tissue is not exposed to high temperatures for extended periods of time. Material containing atoms with low Z-number and atomic weight, providing little intrinsic backscatter signal so as to not interfere with SEM and/or backscattered electron imaging, also provide a suitable substrate for SEM imaging of the thinly sliced tissue.

In some examples, as discussed above, the substrate upon which thin tissue sections are mounted may be boPET (e.g., Mylar). In further examples, so that the substrate exhibits a greater degree of conductivity, substrates may incorporate a carbon additive in any suitable form, such as, for example, in an extra layer deposited on the top and/or bottom of the substrate. In other examples, the substrate upon which thin tissue sections are mounted may be polyimide (e.g., Kapton® produced by DuPont™). Kapton® remains stable at temperatures up to 400 degrees Celsius and has excellent radiation resistance as well. In various examples, thin tissue sections may be collected directly on the surface of bare Kapton® (without a previous carbon coat) and subsequently a very thin layer (~10 nm) of carbon may be deposited on top of the tissue for charge dissipation purposes. In this respect, this tissue section thusly prepared may facilitate sufficient quality high-resolution SEM images of the tissue while appearing to withstand multiple, high-current image captures without damage to the tissue. In addition, use of bare or lightly carbon coated Kapton® makes the feed substrate materials for the ATLUM machine less expensive, avoiding depositing a thick carbon coat (~1 micron thick) onto the long collection tape, which can be an expensive procedure. In general, users of an ATLUM-created UTSL may often require that the same region of a section be imaged multiple times, for example when conducting multiscale imaging or collecting a scanning electron tomographic tilt series. In this regard, collection of tissue on bare or lightly carbon coated Kapton® facilitates repetitive high resolution imaging.

Figure 7:
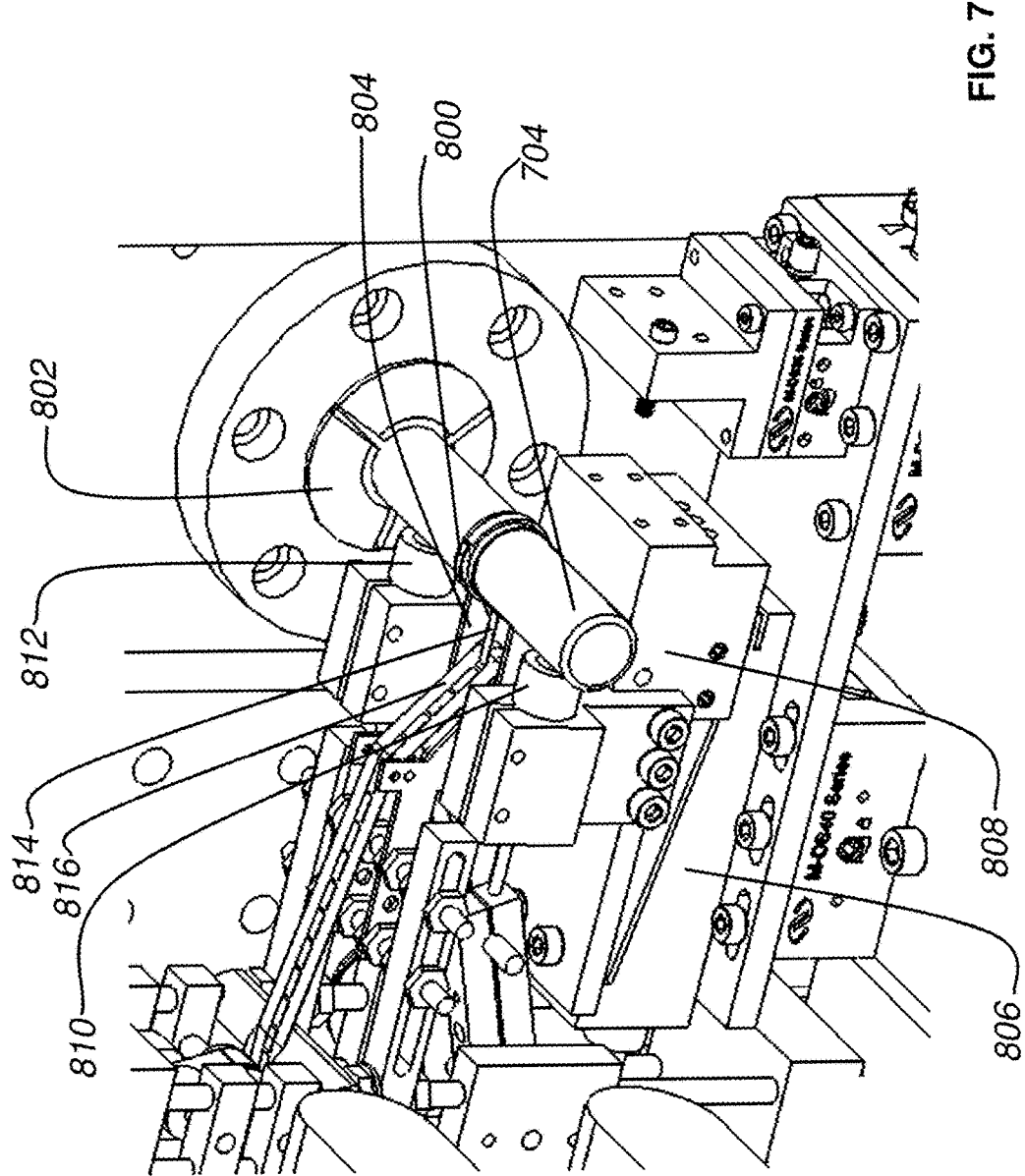
FIG. 7 is a close up perspective view of a knife stage, tissue axle, and conveyor belt collection mechanism according to an embodiment of the present invention.

FIG. 7 shows a closer view of the knife stage, tissue axle, and conveyor belt collection mechanism. A wedge-shaped tissue sample 800 may be mounted on the rotatable axle 704, which may, as discussed above, be mounted in the rotary stage via a collet chuck 802. A diamond ultramicrotome knife 804 may be attached to a piezo tilt stage 806 via a mounting bracket 808. Mounting bracket 808 may also hold a pair of capacitive sensors 810 and 812. These capacitive sensors 810 and 812 may be mounted at essentially the same height as the ultramicrotome knife 804 edge, and configured to measure a distance between the knife edge and the surface of the steel axle 704. Capacitive sensors 810 and 812 may be mounted on either side of the knife, and thus their averaged distance measurement can effectively measure the distance of the knife edge to the axle surface (with some absolute offset). This averaging of symmetrically mounted sensors can produce a distance measurement that may compensate for any wobble of the axle during its rotation. It should be understood that any appropriate type and number of sensors may be used to measure the distance between knife edge and the steel axle 704. Indeed, it is possible for only one sensor to be used in measuring this distance. The sensor may function in any suitable manner, one example being through a capacitive sensing system. As a result, from knowing the rate at which the knife edge moves towards the steel axle 704 and the rotational velocity of the tissue block around the steel axle 704, the thickness of the resulting sliced tissue section may be suitably estimated. Floating tissue section 814 may be collected from a water boat positioned along with the knife 804 via a partially submerged conveyor belt 816 or any other appropriate method.

FIG. 8A shows the piezo tilt stage 806 from a side plan view with sensors 810 and 812 removed in this view for clarity. A fulcrum 900 of the tilt stage 806 may be positioned directly below the edge of the knife 804. In this respect, the largest cutting forces may be absorbed by the stiffest part of tilt stage 806. When a linear piezo actuator within tilt stage 806 expands it causes the knife to rotate forward around fulcrum point 900. This tilt causes the knife edge 902 to move forward toward axle 704 and to cut off a section of tissue wedge 800 as the axle 704 rotates.

As mentioned above, in one aspect, the tilt stage 806 compensates for variable forces encountered during sectioning. The greatest force on the knife 804 during sectioning is often the force that occurs in the direction that the knife is plowing through the tissue, which force is depicted in FIG. 8A by force vector 905. In various examples, the fulcrum point 900 may be placed directly in line with this force component, reducing torque that may arise which also could move the knife. Smaller forces applied to the knife edge in the direction depicted by force vector 904 may occur during sectioning as well, giving rise to a likelihood for the knife to move away from the axle due to the stage's finite tilt stiffness and due to the stage's finite x-stiffness (x direction parallel to arrow 904). In one aspect, the tilt stage 806 may be piezo actuated, allowing for ~5 nm positioning resolution of the knife edge. In this regard, due to construction of the piezo tilt stage, tilt stiffness and x-stiffness may both be coupled to the piezo actuator and may thus be compensated. When using capacitive feedback (e.g., via the capacitive sensors 810 and 812), an integral control term may effectively provide infinite stiffness, limited by bandwidth, to the piezo actuator. As the tilt stage may couple forces at the knife edge to the piezo actuator, the knife edge may be effectively rigid relative to the axle 704 surface, allowing for reductions in section thickness variations such that large block faces may be sectioned at thicknesses at or below 50 nm. It should be understood that any suitable actuation mechanism may be incorporated in operation of the tilt stage, including, but not limited to, piezo actuation, electromechanical actuation, or any other appropriate method.

It is noted that as a result of use of a tilt stage, as the knife advances during a run, the clearance angle of the knife may change. In some instances, changing clearance angle may be problematic if the clearance angle were to change drastically; however, in the example depicted in FIGS. 7 and 8, the clearance angle may change by only a fraction of a degree over the full range of knife travel, which may be approximately ~300 microns.

FIG. 8B shows the piezo tilt stage 806 from a side plan view with capacitive sensor 810 also shown. The distance that the sensors 810 and 812 are measuring is depicted by dimension 906. This distance may be tightly controlled by a controller 908 which drives the piezo actuator in tilt stage 806. In some examples, the controller 908 may be a proportional-integral-derivative controller or any other suitable feedback controlling device.

Figure 9B:
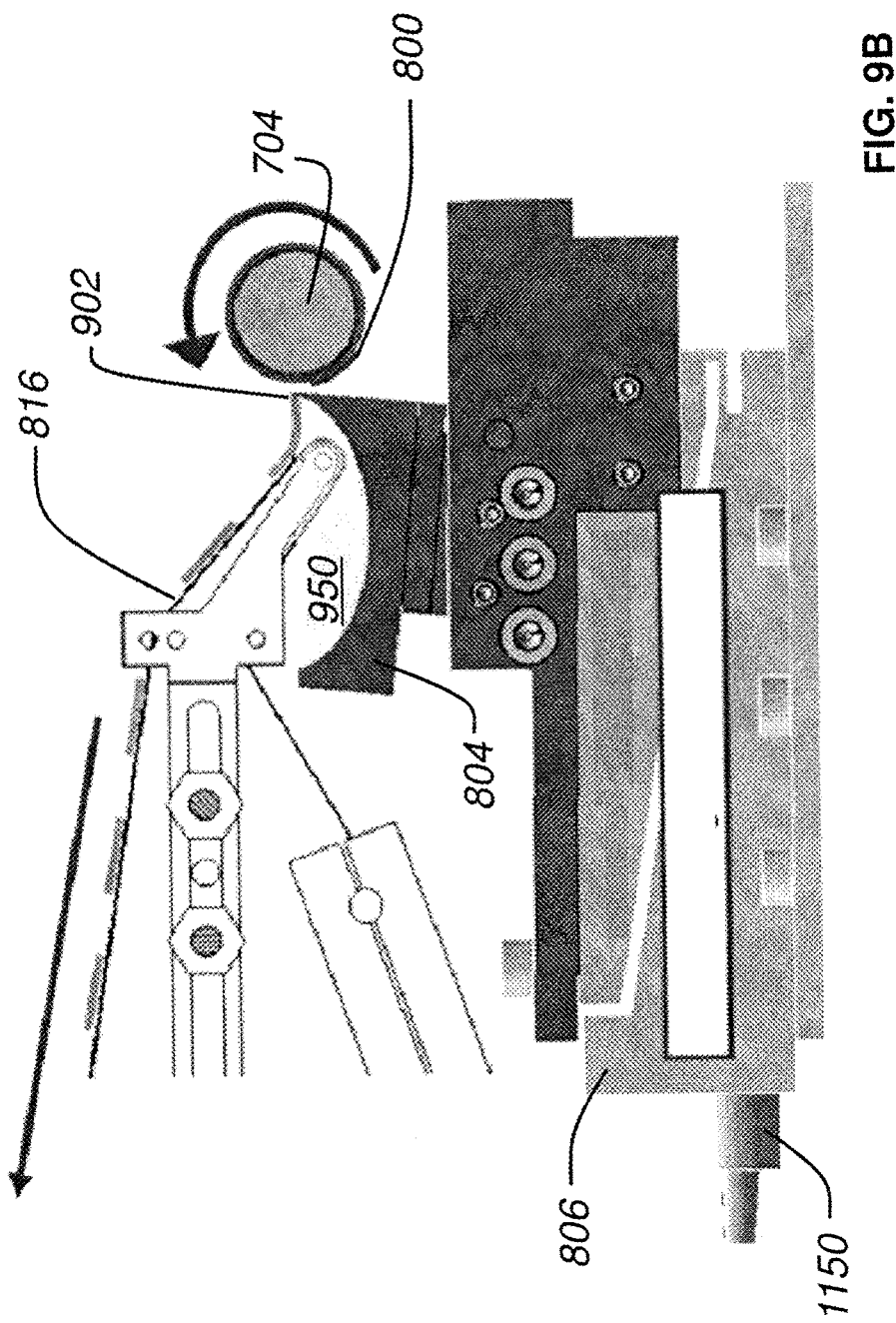
FIG. 9B is a side plan view of a nanosectioning lathe ultramicrotome with a conveyor belt mechanism in operation according to an embodiment of the present invention.

FIG. 5A shows another close-up side view of the piezo tilt stage 806 shown in FIGS. 7 and 8, further illustrating the conveyor belt 816 partially submerged in the water of a water boat 950 behind the edge 902 of knife 804. The water boat may be incorporated directly behind the knife edge such that the surface tension of the water may support the fragile thin tissue section as it is being sliced from the tissue sample 800 on the rotatable axle 704. The surface tension may provide a suitable frictionless support for the thin tissue section, allowing it to stream smoothly off the knife edge. The submerged conveyor belt 816 may also be provided in the water boat close to the knife edge running at a similar speed to that of the tissue sections streaming off the knife edge. In this manner, each tissue section may be gently collected onto the surface of the conveyor belt. The curved bottom 1000 of the water boat 950 is depicted with a dashed line to show how conveyor belt 816 dips into the water but does not scrape the bottom 1000 of the water boat. In this respect, the angle that the edge of the water boat makes with a tangent of the steel axle 704 at the point of slicing may be relatively coincident so that a thin tissue section may come off the axle 704 smoothly and into the water boat. In one example of operation, FIG. 9B shows a tissue block with a protruding tissue wedge 800 mounted on to the steel axle 704 that rotates in proximity to the knife 804. In this example, once the tissue wedge 800 rotates into the knife edge, a thin tissue section may be smoothly sliced off on to the water surface of the water boat. The thin tissue section may then migrate towards the conveyor belt 816 which takes up the thin tissue section for further processing.

In another aspect of the present invention, lathe microtomes may section cylindrical blocks of tissue sample, wedge shaped blocks (which are partial cylinders that do not extend all the way around the rotary axle), or any other shape that may be suitably sectioned. When sectioning a cylindrical block of tissue sample, the knife smoothly advances while the block is rotated. The knife does not disengage from the block of tissue sample and traces a spiral path through the cylindrical block, producing a continuous ribbon of thinly sliced tissue. This process is similar to how a rotary lathe cuts continuous wood veneers by rotating a log past a very wide knife edge. When sectioning a wedge shaped block of tissue sample for a desired section thickness, the knife may be stepped forward once per revolution during the part of the rotation cycle when the tissue wedge is not being cut by the knife. The knife may then be left in place or may move only slightly forward during the part of the rotation cycle when the knife is sectioning the wedge. In these block sectioning modes, rotational motion of the lathe is not required to reverse direction, and knife motion is not required to retract, typically moving forward into the block. In this respect, such attributes, including having stable cutting performance, make lathe microtomes appropriate for automated section collection techniques.

Figure 10C:
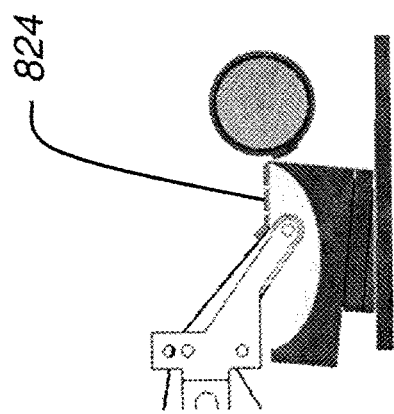
FIG. 10C is a side plan view of a nanosectioning lathe ultramicrotome with a conveyor belt mechanism in operation where the thin tissue section length is shorter than the distance from the knife edge to the conveyor belt according to an embodiment of the present invention.
Figure 10B:
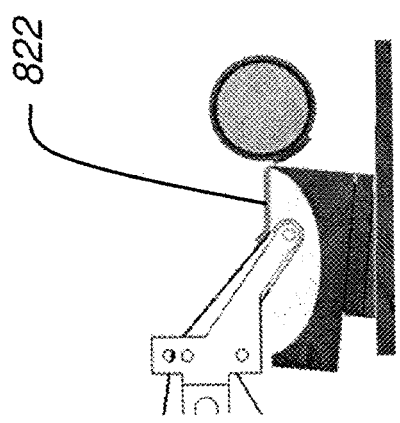
FIG. 10B is a side plan view of a nanosectioning lathe ultramicrotome with a conveyor belt mechanism in operation where the thin tissue section length is longer than the distance from the knife edge to the conveyor belt according to an embodiment of the present invention.
Figure 10A:
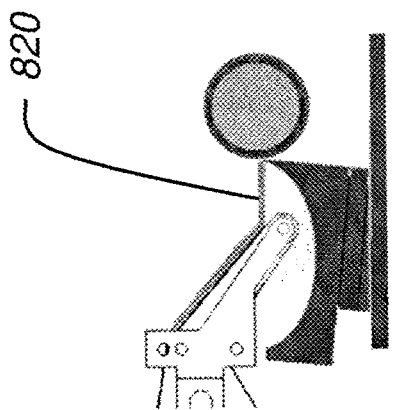
FIG. 10A is a side plan view of a nanosectioning lathe ultramicrotome with a conveyor belt mechanism in operation where the thin tissue section is continuously sliced according to an embodiment of the present invention.

In different examples presented herein, if a continuous ribbon 820 of tissue is being sectioned from a full cylindrical block of tissue sample, as shown in FIG. 10A, then the ribbon 820 may extend from the knife edge, across the water boat for a few millimeters, and to the conveyor belt, where the ribbon 820 may be continuously collected. In this regard, the conveyor belt collection speed should be well matched to the sectioning speed.

In other examples, if a partial cylinder block, or wedge of tissue sample, is being sectioned then it should be considered whether the thin sliced tissue section has a relatively longer length 822, i.e., longer than the distance from the knife edge to the conveyor belt, as shown in FIG. 10B, or whether the sliced tissue section has a relatively shorter section length 824, i.e., shorter than the distance from the knife edge to the conveyor belt, as shown in FIG. 10C. In both of these cases each section may be momentarily secured only at the knife edge while the leading edge of the section is pushed toward the conveyor belt by the momentum of the rest of the section being created behind it. For section lengths 822 that are longer than the distance from the knife edge to the conveyor belt, in order to minimize the tendency for the thin tissue section to bend on its way to the conveyor belt, it may be beneficial for the knife edge to be accurately adjusted so that it is relatively parallel to the tangent of the rotational axis of the lathe at the point of contact. To further minimize tendencies for the thin tissue section to bend on its way to the conveyor belt, the section width may be relatively wide compared to the distance from the knife edge to the conveyor belt. As an example, for a 7 mm distance from the knife edge to the conveyor belt, a section width of 1-2 mm may be used. Further, for reliable collection and full automation to be achieved, the conveyor belt collection speed should be well matched to the sectioning speed.

If the section length 824 is shorter than the distance from the knife edge to the conveyor belt, as shown in FIG. 10C, the sections can still be collected reliably and automatically, where the Nth section may simply be pushed toward the conveyor belt by the (N+1)th section. In this respect, the leading and trailing edges of each section should be relatively straight to prevent the free Nth section from being pushed at an angle by the (N+1)th section. This condition may be met by being sure that the wedge shaped block of tissue sample is shaped such that the leading and trailing edges are substantially parallel to the knife edge. Also, for a greater degree of collection reliability and ability for full automation to be achieved, the knife edge may be accurately adjusted so that it is relatively parallel to the tangent of the rotational axis of the lathe at the point of contact. In addition, the section width may be relatively wide compared to the distance from the knife edge to the conveyor belt. For the case where the section length is shorter than the distance from the knife edge to the conveyor belt, it should be noted that it is not necessary for the conveyor belt collection speed to be well matched to the sectioning speed, but the conveyor belt collection speed should be fast enough to ensure that sections do not bunch up in the water boat.

III. Movable Automated Collection Apparatuses, Systems and Methods

Figure 11B:
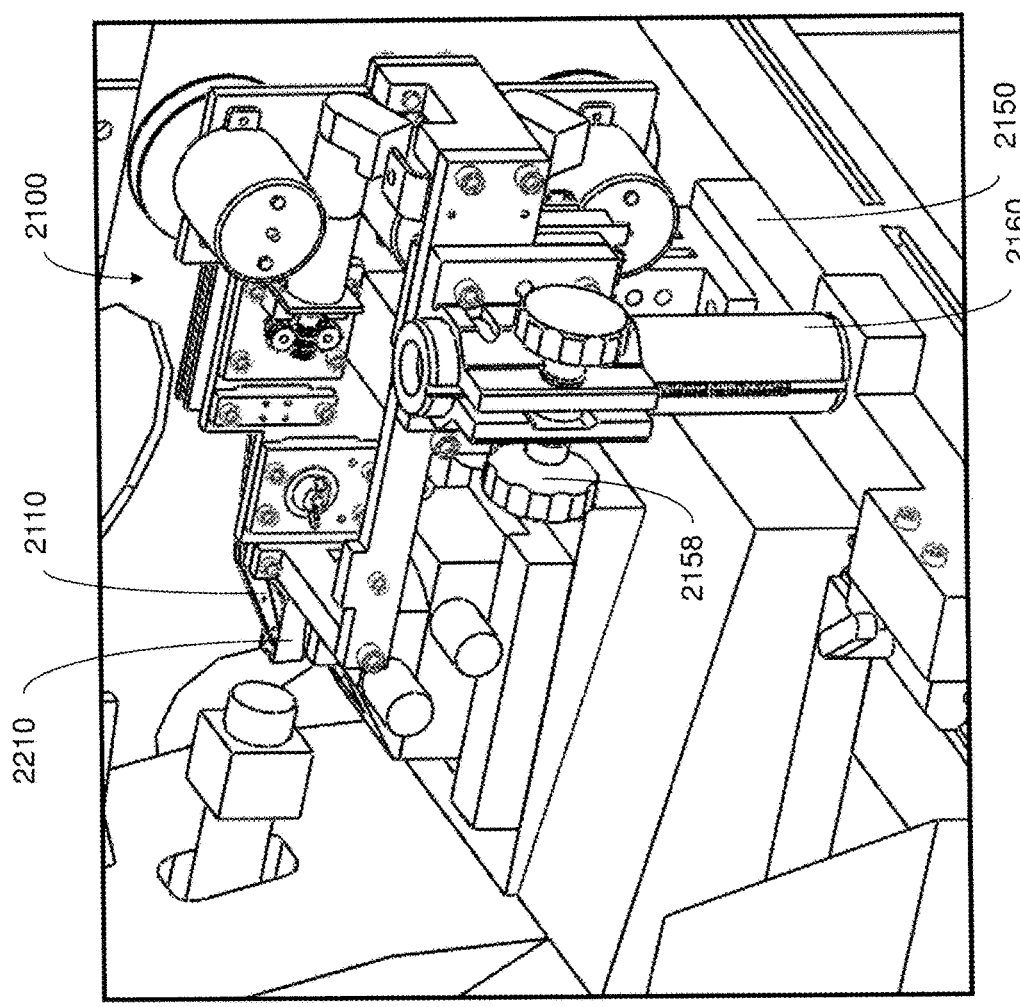
FIG. 11B is a close up perspective view of the collection apparatus of FIG. 11A.
Figure 11C:
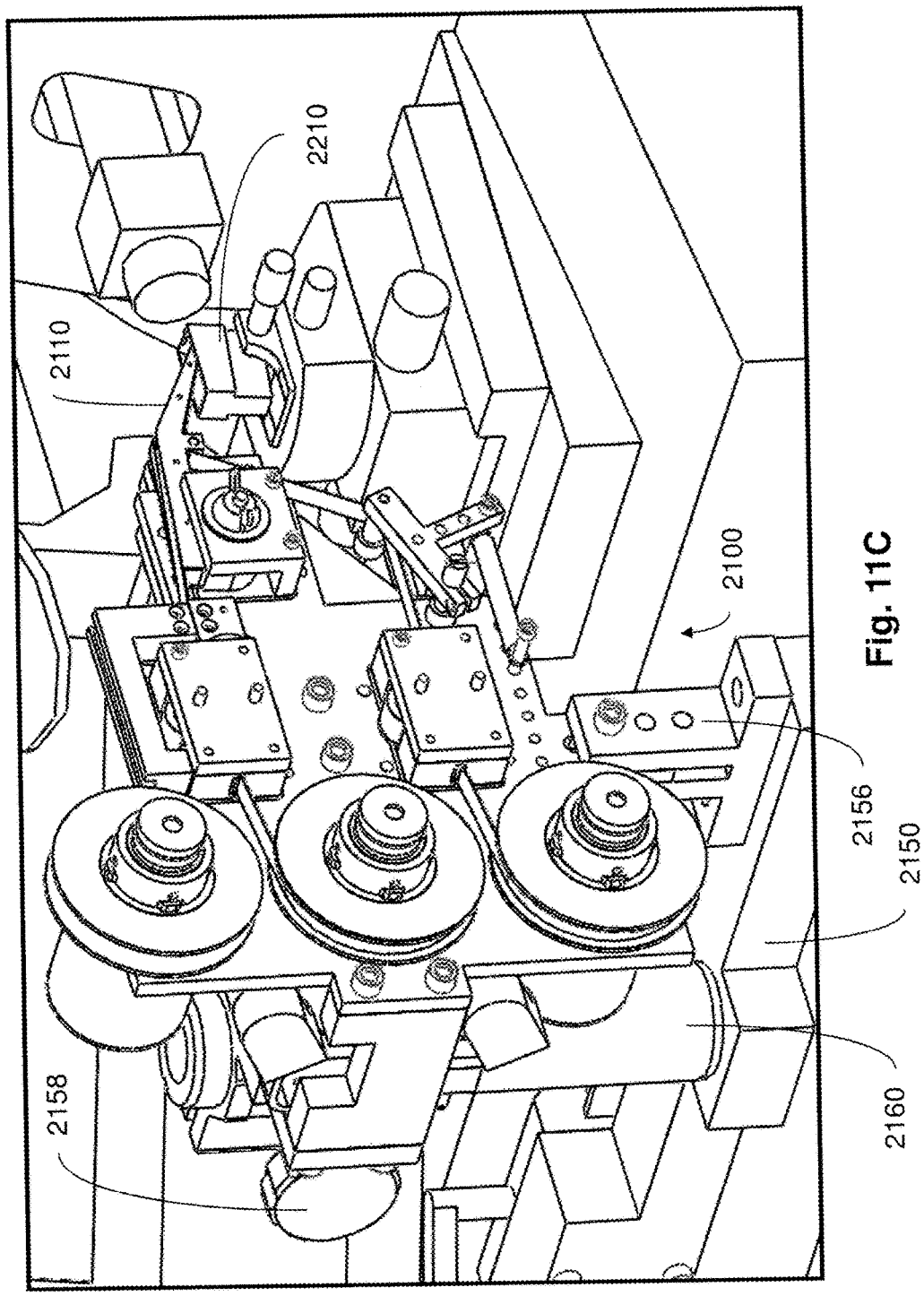
FIG. 11C is another close up perspective view of the collection apparatus of FIG. 11A.

In various inventive embodiments described herein, a collection apparatus may be constructed to be mobile with respect to the microtome, with the ability to be positioned in and out of coupled engagement with any microtome, as appropriately desired. FIGS. 11A-11C illustrate an embodiment of a system 2000 for producing thin tissue sections by slicing a tissue sample, and collecting the thin tissue sections on to a support substrate. The system 2000 includes a collection apparatus 2100 coupled with a microtome 2200 and with certain aspects of the system controlled by a computing device 2300. In the embodiment illustrated, the microtome 2200 is a conventional microtome that functions to slice a tissue sample into thin tissue sections which may float on a liquid surface once they are cut from the microtome knife. The collection apparatus 2100 is positioned at an orientation so as to be engaged with the microtome 2200 to automatically and suitably collect the thin tissue sections from fluid contained within a reservoir 2210 of the microtome. As discussed above, the collection apparatus may be coupled to any suitable microtome known in the art. Collection apparatuses discussed are particularly suitable to be coupled with microtomes where thin tissue sections, upon slicing, come into contact with a fluid surface. In some embodiments, the sole region of physical contact between the collection apparatus 2100 and the microtome 2200 is through the fluid disposed within the reservoir 2210 of the microtome.

A tissue sample is secured in an appropriate position on the microtome from which thin tissue sections are sliced, as can be appreciated by those having ordinary skill in the art. When sliced, for certain embodiments, a thin tissue section slides away from the knife of the microtome on to a surface of fluid (e.g., water) having a surface tension that permits the thin tissue sections to float across the fluid surface. The thin tissue sections are then collected on to a support substrate (e.g., a support tape) where the support substrate moves up a conveyor portion 2110 of the collection apparatus toward a take-up region.

In some embodiments, and without limitation, the collection apparatus 2100 may be suitably attached to a first base portion 2150 which is coupled to a second base portion 2151, as shown in FIG. 12. Either or both of the base portions 2150, 2151 may be weighted so as to keep the collection apparatus in a firm position. Although firmly secured when in operation, for some embodiments, the collection apparatus 2100 is not permanently coupled to the microtome. A rack and pinion 2158, 2160 is attached to first base portion 2150 for moving the collection apparatus 2100 in a vertical motion illustrated in FIG. 12 by double sided dashed arrow v. Second base portion 2151 is coupled to a slide rail 2152 having a lock 2154 that is suitable for fixing the collection apparatus 2100 in place, when desired. Accordingly, collection apparatus 2100 may move in a horizontal motion depicted by double sided dashed arrow h. Vertical and horizontal movement of the collection apparatus relative to the microtome will be described in more detail below.

Figure 13A:
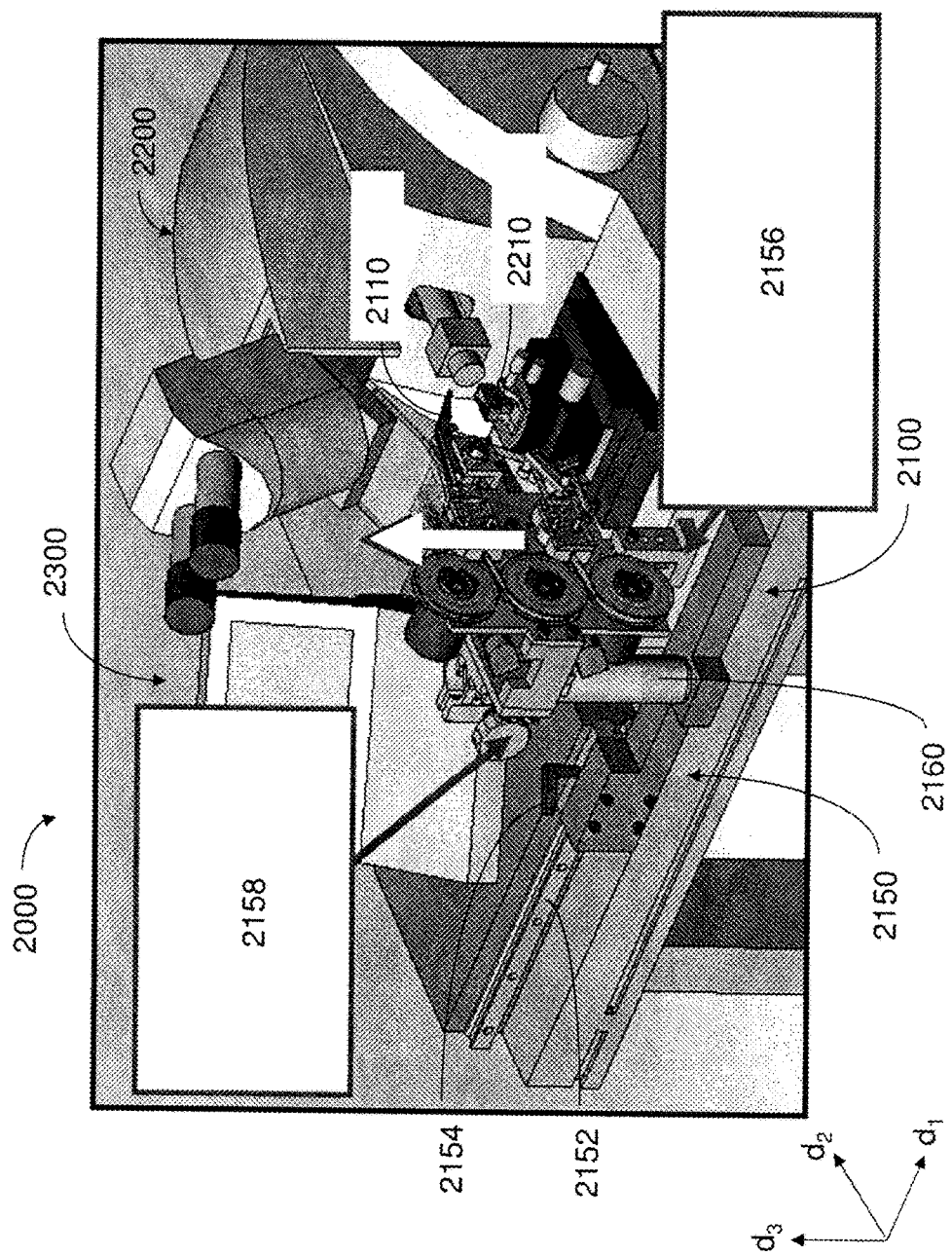
FIG. 13A is a perspective view of the system of FIG. 11A where a collection apparatus is moved away from a microtome.
Figure 13B:
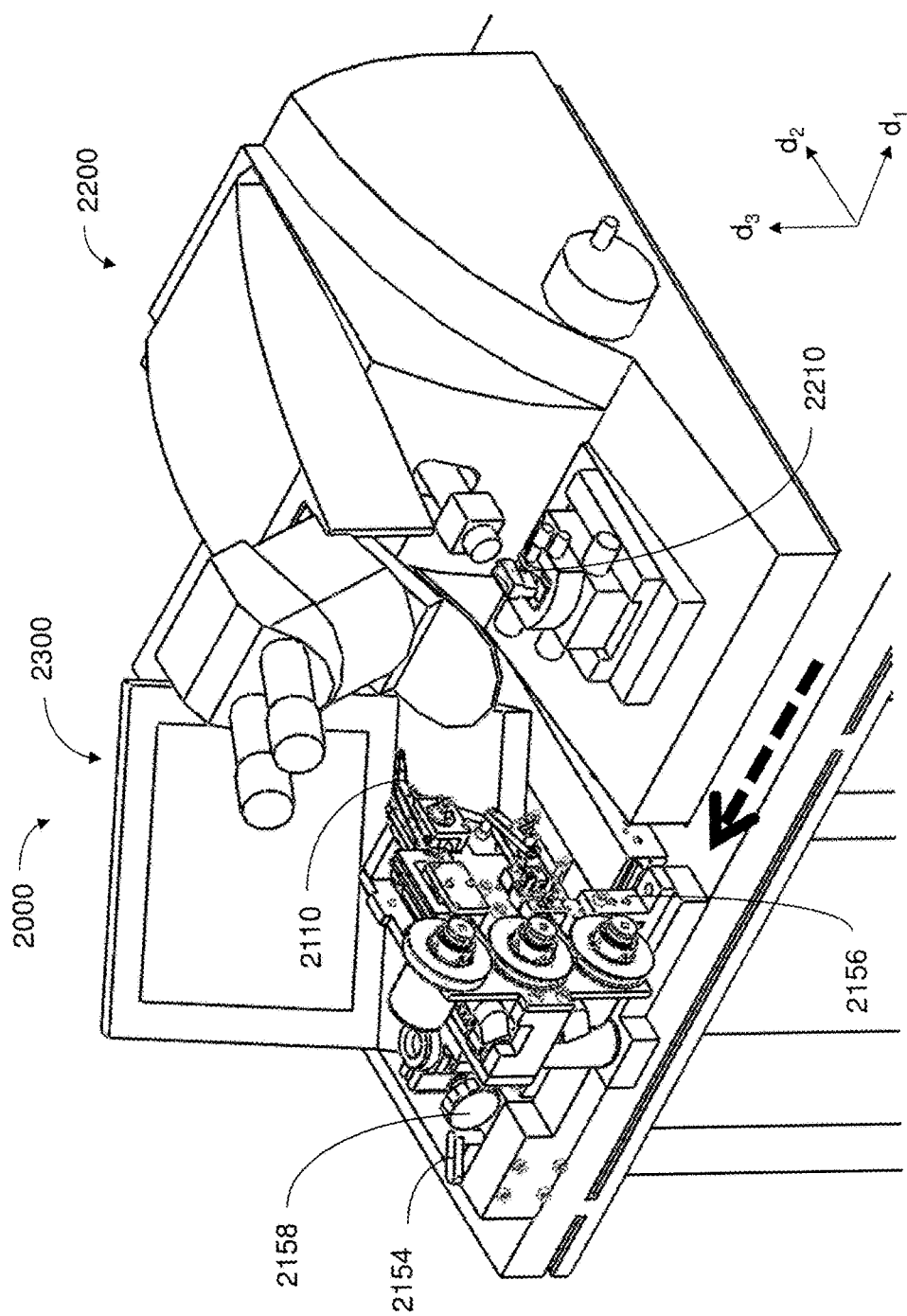
FIG. 13B is a perspective view of the system of FIG. 13A where the collection apparatus is moved further away from the microtome.

As shown in FIGS. 13A and 13B, the collection apparatus 2100 can be removed from engagement with the microtome 2200 such that the collection apparatus is not in a suitable position for automatic collection of thin tissue sections from the microtome. FIG. 13A depicts, for example, raising of the collection apparatus 2100 in a direction $d_3$ so that the conveyor portion 2110 of the collection apparatus comes out of contact with the fluid contained within the reservoir 2210. In some embodiments as discussed above, and without limitation, the collection apparatus can be moved vertically through engagement with a rack and pinion post 2160 (e.g., 2 inch wide post) having a knob 2158 for adjusting the height of the collection apparatus relative to the microtome. Once a suitable height for the collection apparatus is reached, for example, when the conveyor portion 2110 has sufficient clearance from the top of a wall of the reservoir 2210, the rack and pinion post 2160 may be suitably locked (e.g., via a clamp) in place from further vertical motion.

The collection apparatus 2100 may also be constructed to move along a slide rail 2152 upon which the collection apparatus 2100 may slide toward or away from the microtome when not in a coupled arrangement with the microtome for collecting tissue sections. For example, as shown in FIG. 13B, after the collection apparatus 2100 is raised from a position where the conveyor portion 2110 had been operatively oriented in a manner suitable to automatically collect tissue sections from the microtome 2200, the collection apparatus may slide horizontally along the rail 2152 in a direction opposite $d_1$ (along the dashed arrow) to a position further away from the microtome. At any point along the slide rail 2152, lock 2154 can be used to secure the collection apparatus in a stationary position. Upon positioning of the collection apparatus in a non-collecting position a sufficient distance away from the microtome, a user is permitted to perform activities related to routine usage of the microtome, such as block trimming or knife setup, for example. When the collection apparatus is positioned away from the microtome, a user may manually collect tissue sections, for example, using the conventional eyelash collection method.

The collection apparatus 2100 may be moved from a non-collecting position in a positive direction $d_1$ and into a collecting position where the apparatus is in a coupled arrangement with the microtome; that is, where automated retrieval of thin tissue sections may suitably occur from the microtome on to portions of the collection apparatus. For example, the collection apparatus may move along rail 2152 toward the microtome and, when in a suitable horizontal position with respect to the reservoir 2210, may be lowered in a direction opposite $d_3$ into an appropriate position for automated collection of tissue sections.

A positioning feature 2156 may facilitate placement of the collection apparatus in a suitable collecting position. In some embodiments, a positioning feature 2156 includes a pedestal for preventing the collection apparatus from being excessively lowered. For some cases, it may be detrimental for the conveyor portion 2110 of the collection apparatus 2100 to be lowered beyond the surface of the fluid contained within the reservoir 2210 in a manner, for example, where the conveyor portion forcibly contacts the bottom of the reservoir. A positioning feature 2156 may incorporate a pedestal to serve as a stop feature upon lowering the collection apparatus so that a user is not required to make precise readjustments each time the collection apparatus is to be placed in a collecting position. For some cases, positioning feature 2156 may include a pin adjustment for the collection apparatus to be suitably placed at a desired height. For example, in a pin adjustment, a pin may be placed along various points in a support structure corresponding to different heights for the collection apparatus to be positioned. Accordingly, if a user determines that a collection apparatus should be placed at a collecting position that is lower than a previous collecting position, a pin may be pulled out of an existing socket and placed into a socket corresponding to a lower position.

Figure 14A:
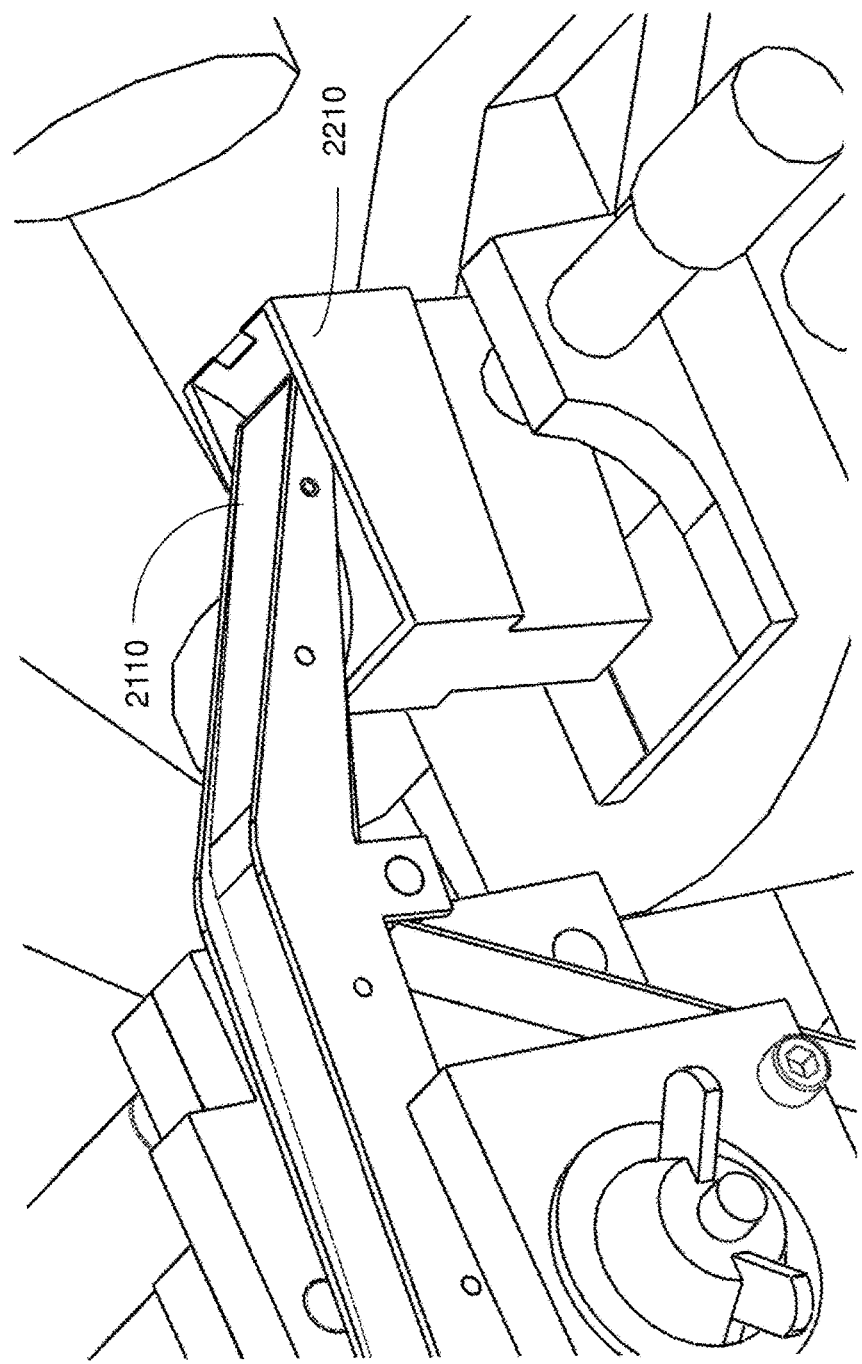
FIG. 14A is a close up perspective view of a conveyor portion and a fluid reservoir of a microtome in accordance with embodiments described.
Figure 14B:
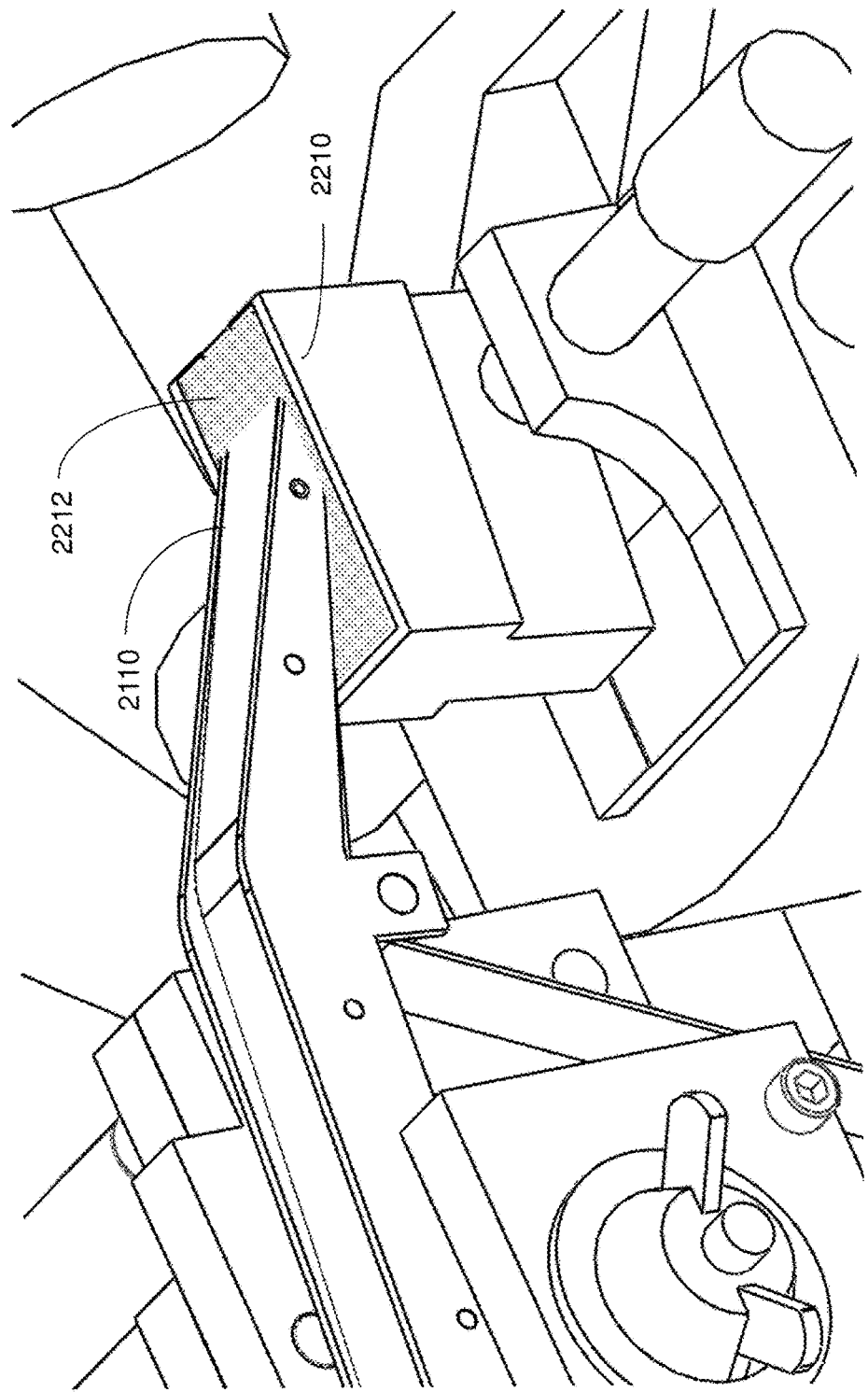
FIG. 14B is a close up perspective view of the conveyor portion and fluid reservoir of FIG. 14A with fluid disposed in the reservoir in accordance with embodiments described.

Placing the collection apparatus into a collecting position involves an arrangement that suitably results in automatic and continuous retrieval of thin tissue sections on to a support substrate for long periods of time. As discussed above, a collection apparatus initially located at a non-collecting position a distance away from the microtome may be moved toward the microtome and placed into a coupled arrangement with the microtome, as shown in FIGS. 14A and 14B. For example, part of the conveyor portion (e.g., a tip) of the collection apparatus may be partially submerged into a fluid contained within a reservoir of the microtome.

In some embodiments, coupling of the collection apparatus with the microtome involves horizontally positioning the collection apparatus in a direction along with or opposite $d_1$ so that the conveyor portion is centered with respect to the fluid reservoir. For example, the distance between side edges of the conveyor portion and side walls of the reservoir may be about 0.5 mm. Once the collection apparatus is horizontally centered, the vertical position of the collection apparatus may then be adjusted to ensure that the support substrate will be submerged in the fluid, without scraping against the bottom of the reservoir. Further, the collection apparatus may be adjusted in a forward-backward direction along or opposite $d_2$ so as to set an appropriate distance between the edge of the microtome knife and the point of collection; that is, the point where the support substrate emerges from the fluid. In some embodiments, the distance between the edge of the microtome knife and the point of collection is slightly longer than the length of a sliced tissue section. FIG. 14A depicts a suitable position of the conveyor portion 2110 of the collection apparatus with respect to the reservoir 2210 of the microtome. As shown in FIG. 14B, the reservoir 2210 contains an appropriate fluid 2212 having a surface tension suitable for supporting thin tissue sections sliced from the knife of the microtome.

In some embodiments, rather than straight horizontal and/or vertical movement of the collection apparatus with respect to the microtome, a system may provide for the collection apparatus to be rotated toward and/or away from coupled arrangement with the microtome. For example, the collection apparatus could be arranged to rotate about a pivot (not shown in the figures) with respect to the microtome.

Although movement of the collection apparatus 2100 relative to the microtome 2200 has been described with respect to manual operation, it should be appreciated that such movement of the collection apparatus into and out of a collecting position may occur automatically. For example, an operator that observes a collection apparatus positioned away from the microtome in a non-collecting position may easily initiate an automated collection process by sending a command (e.g., pressing a button) to a control system having actuators that automatically move the collection apparatus into a suitably coupled arrangement with the microtome.

Turning back to the embodiment shown in FIG. 12, a vertical actuator 3010 is coupled to the collection apparatus 2100 for automatically and suitably moving the collection apparatus 2100 in a vertical motion in accordance with double sided dashed arrow v. In addition, horizontal actuator 3020 is coupled to the first base portion 2150 of the collection apparatus for automatically and suitably moving the collection apparatus 2100 in a horizontal motion along double sided dashed arrow h via slide rail 2152. As such, vertical actuator 3010 and horizontal actuator 3012 may be in communication with a suitable computer-controlled device so as to function in tandem to mechanically move the collection apparatus into and out of a collecting position. Actuators 3010, 3012 may include appropriate electrical and/or mechanical components (e.g., solenoids, actuators, motors, etc.) that enable suitable movement of the collection apparatus without requirement for a user to manually move the collection apparatus between collecting and non-collecting positions. Any suitable number of actuators coupled between a controller and the collection apparatus may be used. For example, additional actuators for fine, coarse, linear and/or rotational movement of the collection apparatus may be incorporated. The system may also employ feedback to determine whether the collection apparatus is in a collecting position. For example, the position of the collection apparatus may be tracked through a video monitoring device and, through feedback to the controller, a signal may be sent to the actuator(s) to adjust the position (e.g., vertically, horizontally, rotationally, etc.) of the collection apparatus accordingly.

In some cases, the system may also be configured to automatically commence production and collection of thin tissue sections on to a support substrate when the collection apparatus is in an appropriate position. Thus, by initiating a simple command, actuators coupled to the collection apparatus may move the collection apparatus into suitable engagement with the microtome and once in the collecting position, automated collection of thin tissue sections is initiated. Once thin tissue sections are sufficiently collected, the system may further provide for automatic movement of the collection apparatus away from the microtome. Thus, for some cases, collection of thin tissue sections may be completely automated.

As tissue sections are collected, fluid is typically lost due to evaporation from the reservoir and removal of fluid by the support substrate. In some embodiments, fluid in the reservoir of the microtome is automatically maintained at a constant level during operation of the collection apparatus, compensating for fluid loss and ensuring that fluid is continually available at the edge of the microtome knife. Maintaining contact of tissue sections with fluid provides for appropriate lubrication of the tissue sections as well as surface tension support of the tissue sections on the fluid once cut from the knife. In manual collection schemes, fluid levels are not automatically maintained, and fluid may be added, as appropriately desired. However, when tissue sections are automatically collected, despite continual loss of fluid, it is advantageous for fluid levels to be kept constant without need for user intervention. It should be appreciated that any suitable fluid may be provided in the reservoir. For example, the fluid may be water, an aqueous solution or a non-aqueous solution.

In a representative embodiment, a reservoir contains water maintained at a level where the edge of the microtome knife is continuously wet during sample cutting. That is, the level of water is at least close enough to the knife to form a concave meniscus or is at a level that is even with the edge of the knife, keeping the cutting edge of the knife wet. In some cases, the water level is kept at a level slightly lower than the knife edge so that the concave meniscus wets the edge of the knife, enabling the tissue sections to slide down a slope formed by the concave meniscus.

A system including a computing device may be coupled to a video monitoring device for assessing the current level of fluid in a reservoir and a fluid input apparatus (e.g., perfusion pump, syringe, etc.) for introducing fluid into the reservoir when desired. The computing device may be used to send signals as a controller in a feedback system for automatically maintaining the level of fluid in the reservoir. The computing device records and analyzes video images of the fluid level in the reservoir by detecting the dark-to-light boundary of a reflective sheen produced by the fluid.

Figure 15A:
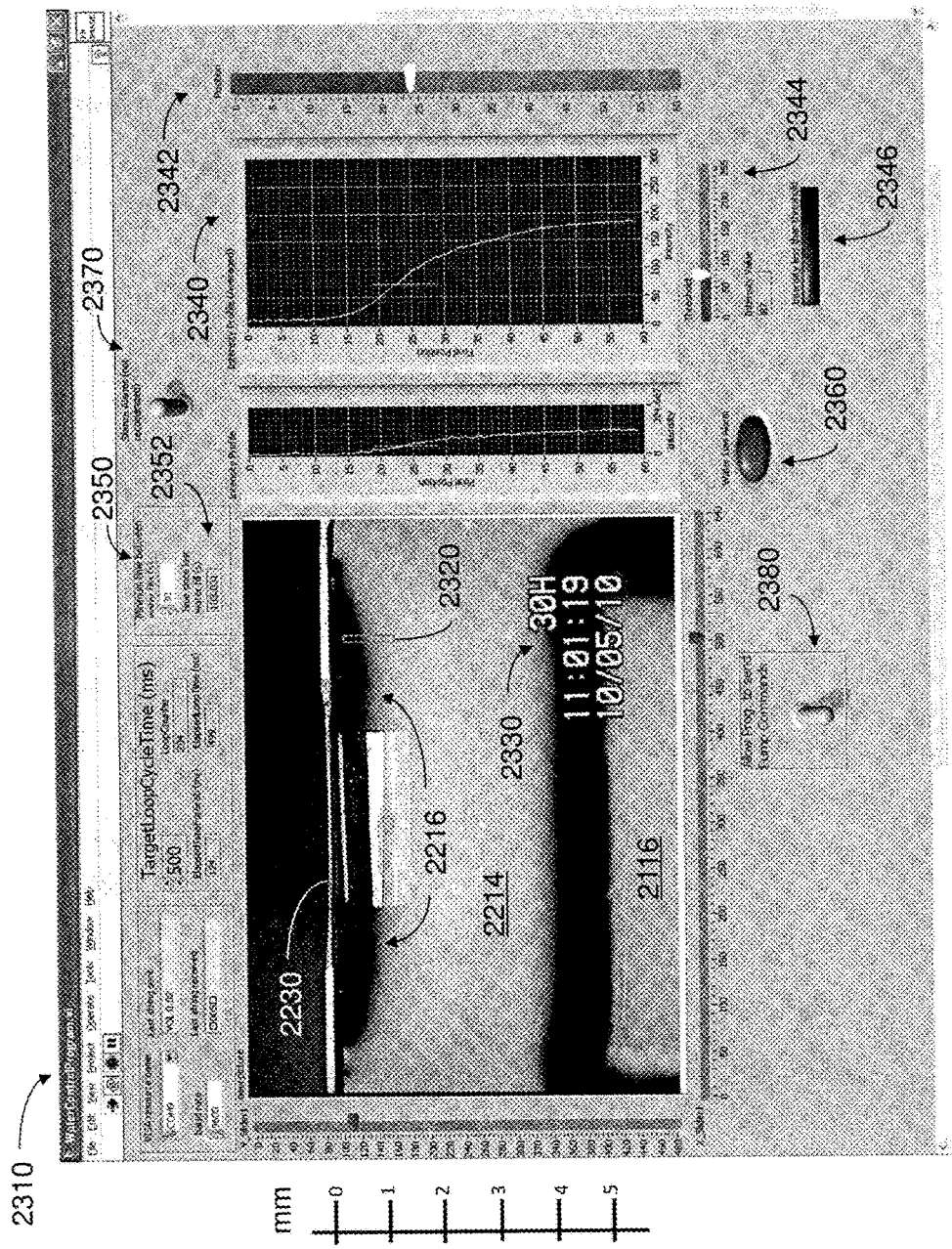
FIG. 15A is a screenshot of a user interface in accordance with embodiments described.

In an example, a computing device 2300 may provide a user interface 2310, as illustratively shown in FIG. 15A. In some embodiments, a flat water surface 2214 may reflect white diffuse light into a video monitoring device and is recorded as a uniform white color in the video image. A concave meniscus formed with the edge of the knife 2230, on the other hand, may produce an angle of reflection from the water such that recorded video images of the meniscus are black in color. The contrast in image between a flat water surface reflection 2214 and a concave meniscus may be apparent as a boundary 2216 recorded from the imaging apparatus. A contrast sensing region 2320, depicted in FIG. 15A as a slender rectangle, may be traced out in the recorded image to quantify where the boundary 2216 is located, defining the distance between the knife edge 2230 and the edge of the concave meniscus. Such a method of measure provides a sensitive technique in measuring the current level of water in the reservoir so as to provide an indication of whether a knife edge maintains wetness in a manner where thin tissue sections may be collected automatically over prolonged periods of time.

The computing device performs image analysis of the video information gathered from the video monitoring device and determines the distance of, for example, the concave meniscus from the edge 2230 of the knife. When the surface of water extends a distance from the knife edge that is beyond a threshold for suitable operation of tissue section collection, a small amount of water is injected into an appropriate region of the reservoir so as not to interfere with collection (e.g., with minimal turbulence). For example, and without limitation, the dark region of the video, signifying the presence of the concave meniscus, is maintained for suitable operation of the automatic collection system such that an edge of the dark region closest to the edge of the knife extends between about 0.2 mm and about 0.5 mm from edge of the knife, as measured by the contrast sensing region 2320. When the computing device detects, from the video information, that the edge of the dark region extends beyond 0.5 mm from the edge of the knife (e.g., due to evaporation, transport by movement the support substrate, etc.), an appropriate signal is sent to the input apparatus for an increment of water (e.g., about 0.05 mL or less, or about 0.02 mL or less) to be introduced into the reservoir. Conversely, for some embodiments, when the computing device detects that the fluid level is too high, or for example, extends above the knife edge 2230, fluid may be appropriately removed from the reservoir. It should be appreciated that the threshold boundaries for which the system is alerted to introduce into or remove fluid from the reservoir may vary as appropriately desired. Although not so limited, the distance between the knife edge 2230 and an edge of a tip 2116 of the conveyor portion may be about 5 mm, as shown in FIG. 15A.

In some embodiments, so that the water level does not increase too quickly to cause tissue sections to undesirably drift away from suitable locations for support substrate retrieval, the computing device may send appropriate signal(s) to the input apparatus to pause for a brief period of time (e.g., at least about 30 seconds) between subsequent injections. In some embodiments, the total fluid volume introduced into the reservoir of a microtome at a particular interval, when the current fluid level is detected to be less than a threshold of an operating level, is between about 0.05 mL and about 0.20 mL, for example, about 0.10 mL.

Control interface 2310 may include control features, such as those depicted in FIG. 15A. A time stamp 2330 may be provided, for example, indicating to a user what the time is during a collection process run or for how long a collection process has been run. The interface may also include a intensity profile 2340 measured across the contrast sensing region 2320 as a time averaged pixel intensity of the recorded image. In some embodiments, the location of the boundary 2216 between the flat water surface and the concave meniscus is determined by assessing the pixel position along the contrast sensing region 2320 where the change in intensity is greatest. The location of the boundary 2216 across the contrast sensing region 2320 may be indicated by a position indicator 2342. The threshold for determining at what position the boundary 2216 is to be located to trigger input of additional fluid may be set by a user through the interface 2310 via a threshold control 2344. An indicator 2346 may also be provided to alert a user when the threshold of the boundary 2216 exceeded.

With respect to other aspects of water filling provided by the user interface 2310, the minimum time between each discrete input of water may be set using control 2350. For example, if it is desired for the fluid input apparatus to pause for more than 30 seconds before introducing additional fluid into the reservoir, the time lapse between filling can be set to a greater time increment. An indicator 2352 may also show to the user the time since a last fluid input has occurred. User interface 2310 may include an alarm 2360 to alert the user when fluid levels are low. As such, the threshold for signaling the alarm may be set according to the threshold control 2344, or may be set according to another suitable level of measure.

The user interface 2310 may also permit a user to activate and deactivate certain features of the controller. For example, an alarm silence switch 2370 may be provided for a user to silence alarms associated with the system, as desired. In some cases, silencing of alarms may not be advisable since, when an alarm is silenced, a user may be less prone to be aware of a situation that requires adjustment (e.g., when the fluid level in the reservoir is too low and tissue sections are not being collected properly on to the support substrate). In addition, fluid input switch 2380 may also be provided, which permits the controller to send a signal to the fluid input apparatus for automatic fluid input into the reservoir without user intervention. Deactivating the fluid input switch 2380 may turn off the automatic fluid input feature, requiring a user to manually input fluid into the reservoir as needed.

Figure 15B:
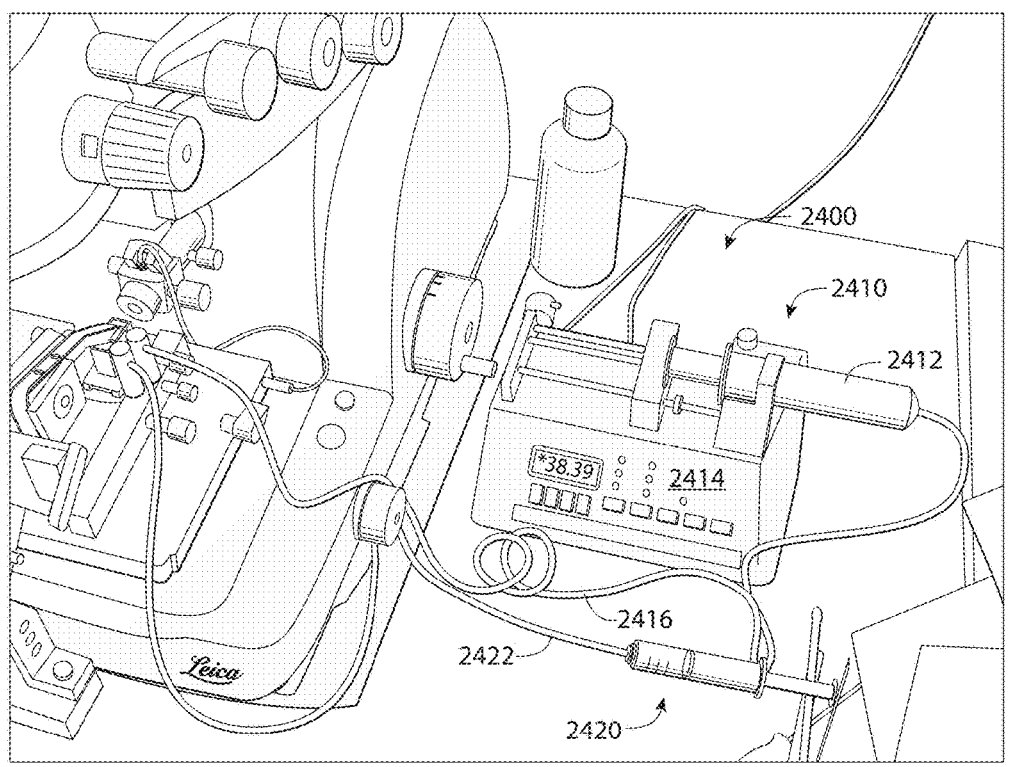
FIG. 15B is a view of a fluid input apparatus in accordance with embodiments described.
Figure 15C:
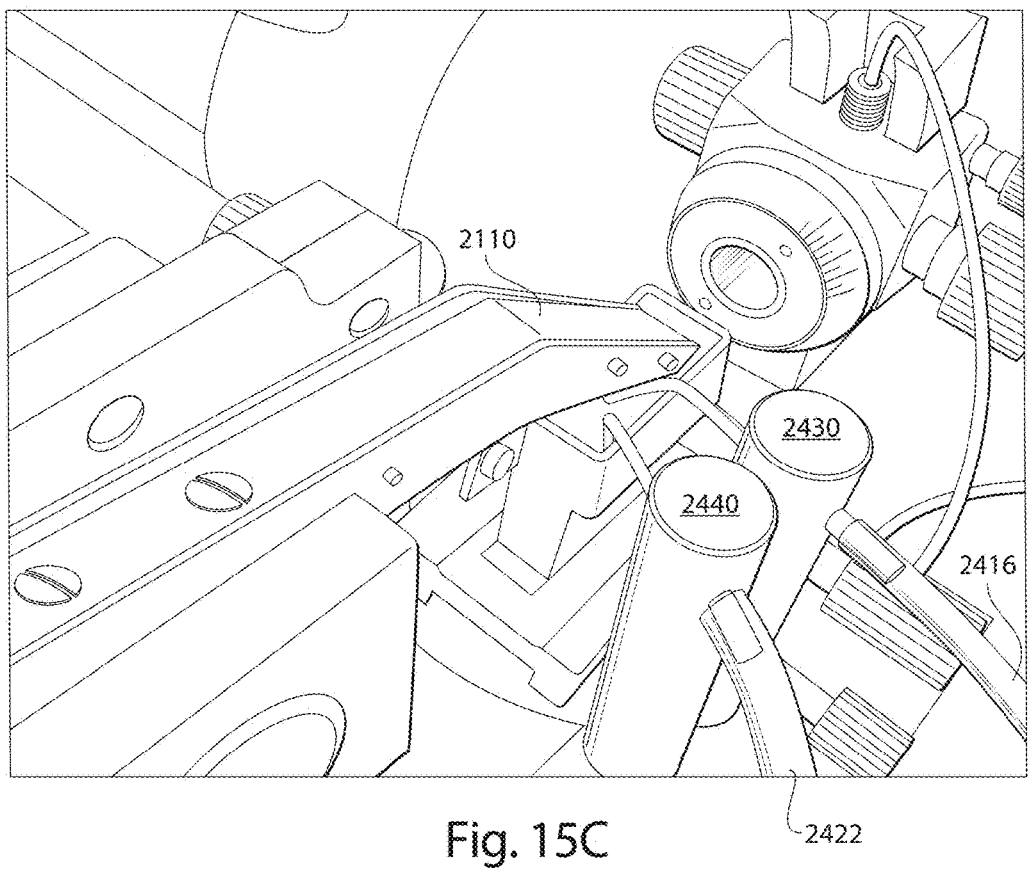
FIG. 15C is a close up view of a fluid input apparatus engaged with a reservoir in accordance with embodiments described.

An embodiments of a fluid input apparatus setup 2400 shown in FIGS. 15B and 15C includes an automatic input device 2410 and a manual input device 2420. The automatic input device 2410 includes a pump 2412, a pump controller 2414 and a channel 2416. Pump 2412 and channel 2416 are in fluid communication with the reservoir of the microtome. The pump controller 2414 may be connected with a controller of the computing device 2300 and may receive signals for the automatic input device 2410 to introduce fluid from pump 2412 into the reservoir through the channel 2416. The pump controller 2414 includes an actuating portion that applies an appropriate force to the pump 2412 when an actuation signal is received from the computing device 2300. Alternatively, a user may manually input fluid into the reservoir from manual input device 2420, shown in FIG. 15B as a syringe, through channel 2422 which are also in fluid communication with the reservoir. FIG. 15C shows a close up view of an input nozzle 2430 having a spout leading to the reservoir and in fluid communication with channel 2416 of the automatic input device 2410. Input nozzle 2440 is also shown to have a spout for fluid input into the reservoir and in fluid communication with channel 2422 of the manual input device 2420. Input nozzles may be arranged so that turbulence is minimized upon fluid input into the reservoir.

Controlling the level of fluid within the reservoir of the microtome may enable automated collection of tissue sections for extended periods of time. In some embodiments, absent a method for the fluid level in a reservoir to be maintained, automated collection runs may last until fluid levels are in need of replenishment (e.g., about 30 minutes); though, by implementing a manner under which fluid levels may be tightly controlled, collection runs may last for several days at a time.

Figure 16A:
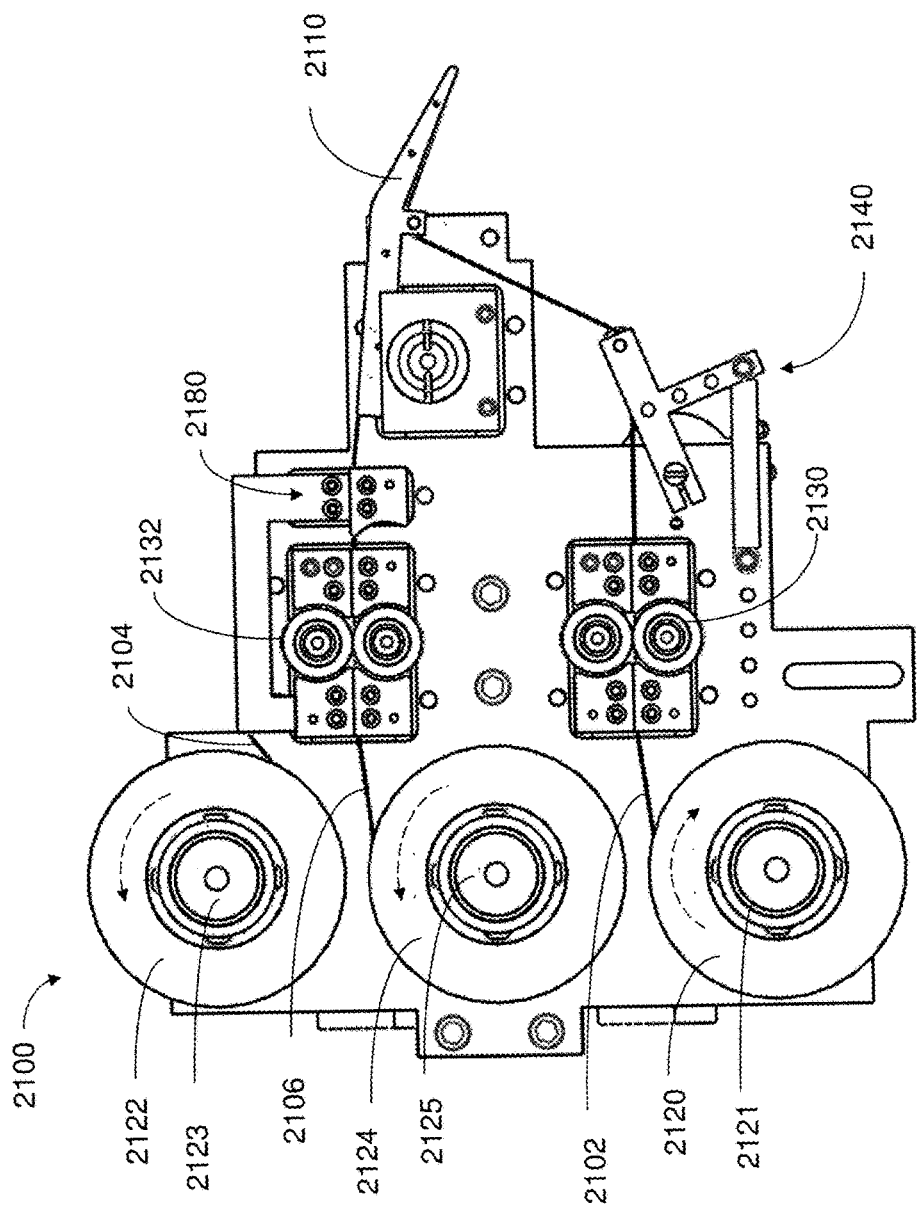
FIG. 16A is a side plan view of a collection apparatus in accordance with embodiments described.
Figure 16B:
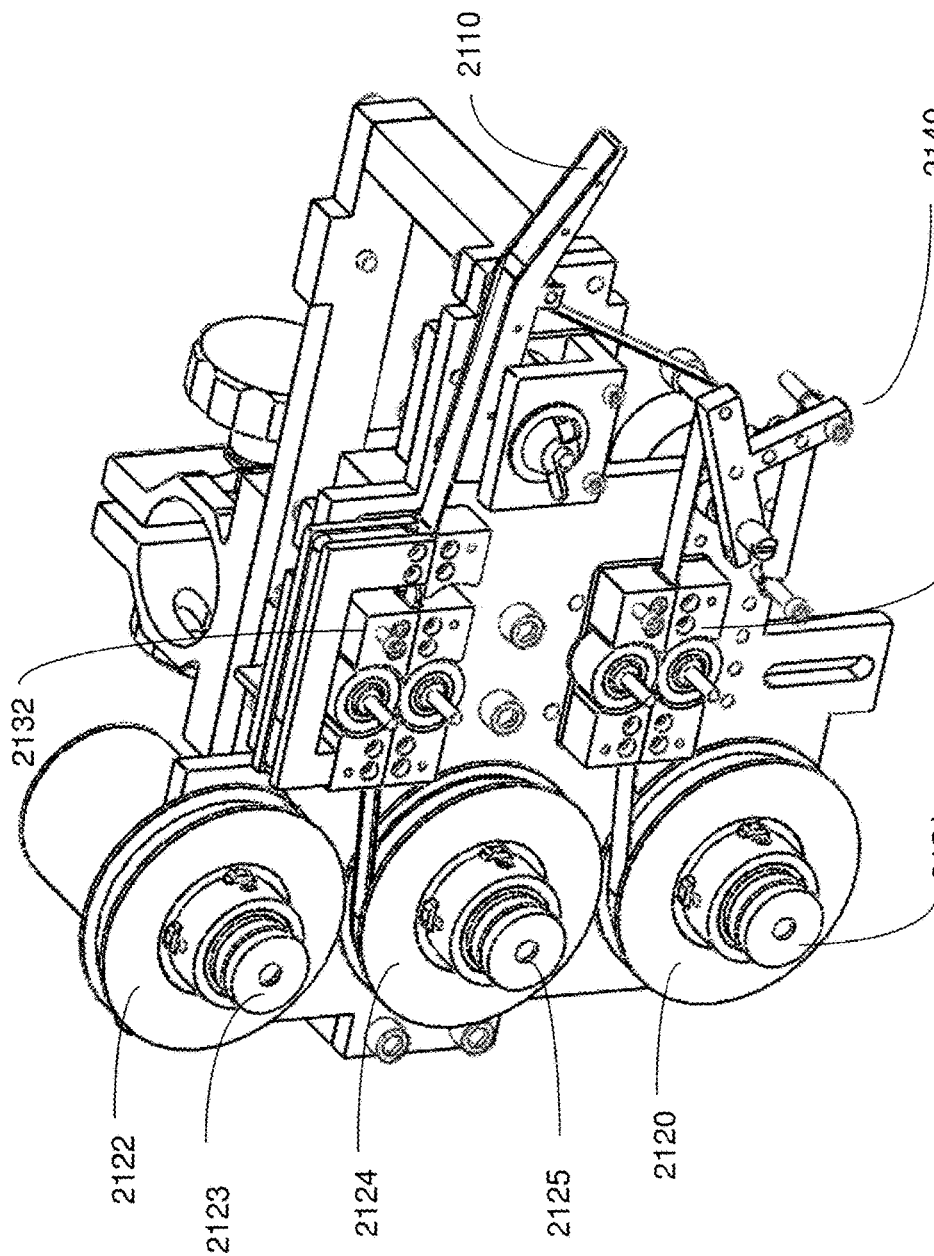
FIG. 16B is a perspective view of the collection apparatus of FIG. 16A in accordance with embodiments described.
Figure 16C:
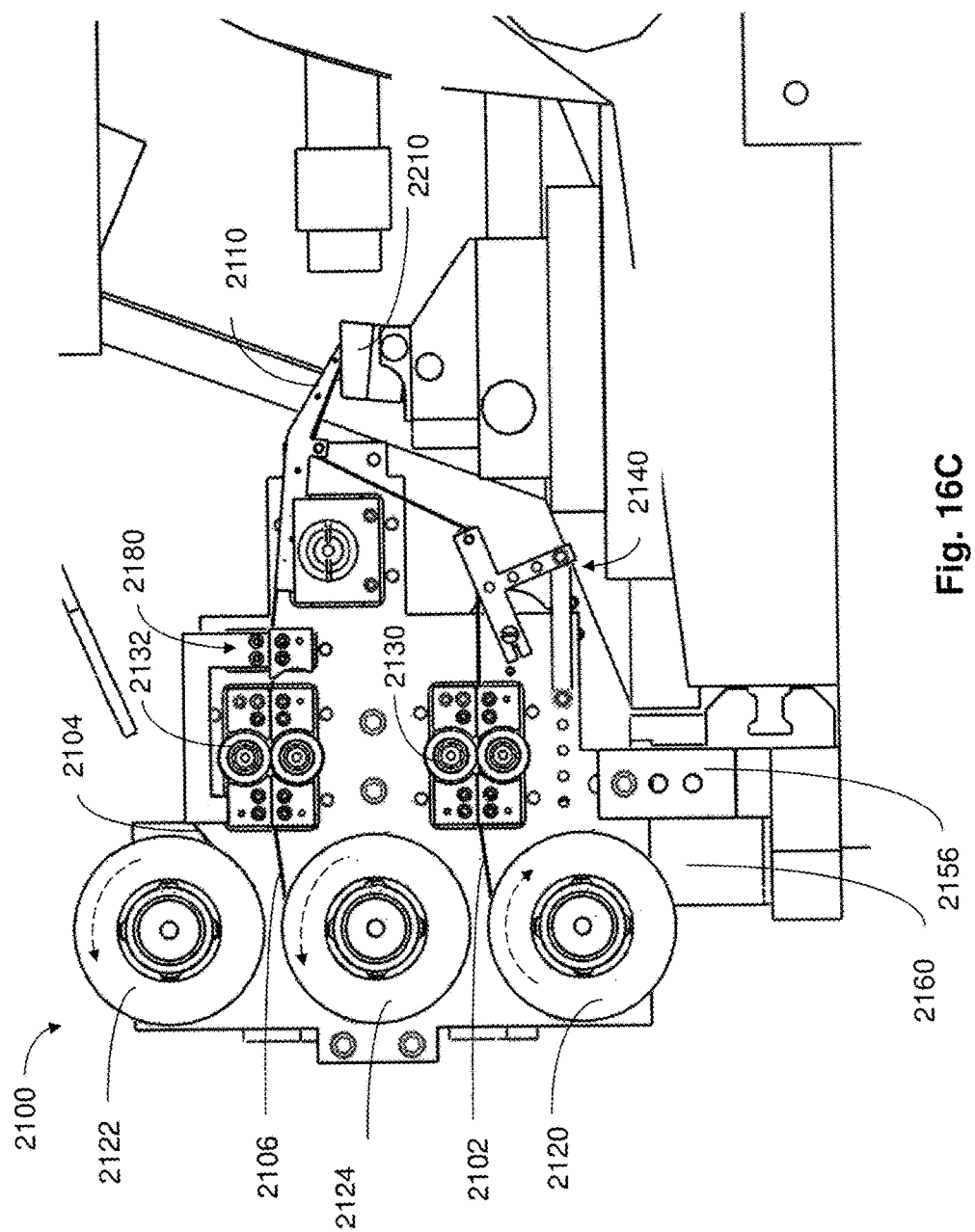
FIG. 16C is a side plan view of the collection apparatus of FIG. 16A in coupled arrangement with a microtome in accordance with embodiments described.

In certain representative embodiments, thin tissue sections may be collected on to a moving support tape that is stored on a take up reel prior to imaging. As illustrated in FIGS. 16A-16C, though not meant to be limiting, the collection apparatus 2100 may include a support tape feed reel 2120 mounted on a support tape feed reel holder 2121, a cover tape feed reel 2122 mounted on a cover tape feed reel holder 2123, and a take up reel 2124 mounted on a take up reel holder 2125.

The support tape feed reel 2120 provides a support tape 2102 for collecting thin tissue sections on to a top surface of the support tape. In this regard, the support tape feed reel 2120 rotates in a clockwise direction from the perspective of a viewer of FIG. 16A, as depicted by the dashed arrow. The cover tape feed reel 2122 rotates in a counter-clockwise direction, along the corresponding dashed arrow, in providing a cover tape 2104 that may be optionally applied to the support tape having thin tissue sections disposed thereon. Although not required, when a cover tape 2104 is applied on to the thin tissue sections disposed on the underlying support tape, the cover tape may be appropriately aligned with the support tape via an applicator 2180 once the support tape comes off the back end of the conveyor portion 2110. Further, the take up reel 2124 rotates in a counter-clockwise direction, depicted by the dashed arrow on take up reel 2124, to collect the final support substrate 2106 having thin tissue sections disposed, at least, on a support tape.

While not expressly shown, any of the reels may be appropriately removed and/or replaced when desired. For example, when the support tape feed reel 2120 is empty or when take up reel 2124 is at full capacity, either or both of these reels may be replaced by a user, or alternatively, by a suitable automated reel replacement system. Reels on a collection apparatus may be easily and conveniently replaceable. For example, reel holders may be firm to hold respective reels in place during operation, yet deformable so that reels can be conveniently removed and replaced. Reel holders may be suitably manufactured, for example, to include rubber prongs, or to have a suitable insert mechanism (e.g., slot insert) that allows a reel to be conveniently mounted and removed from the holder. In some cases, reels may be mounted on a reel holder via a suitable interference fit.

In some embodiments, portions of reels described may be transparent, allowing a user to clearly observe how much tape (e.g., support tape, cover tape, recovered tape on a take up reel) remains on a particular reel. For example, if there is very little support tape remaining on a support tape feed reel 2120, then a user may remove the feed reel and replace it with a reel having more feed stock of support tape. If the take up reel 2124 is at full capacity or almost at full capacity, the user may remove the take up reel, for further processing/imaging of the tissue sections on the take up reel at a later time, and replace it with an empty take up reel. A full feed reel may be sufficiently long (e.g., over 40 m long) for several collection runs to be performed. For example, if a support substrate is about 50 microns in thickness, approximately 10,000 thin tissue sections can be collected, spaced about 4 mm apart.

For some embodiments, it may not be desired for tissue sections to be sandwiched between a cover tape and a support tape; that is, for a cover tape to be applied to a support tape. Hence, collection runs can be performed without including a cover tape feed reel 2122 mounted on the cover tape feed reel holder 2123. Though, when desired, a cover tape feed reel 2122 may be conveniently and suitably be placed on cover tape feed reel holder 2123, and used as desired. In one embodiment, where a cover tape is not used, the top roller of the top pinch drive is oriented such that the roller only presses down on the sides of the support tape. For example, for an 8 mm wide support tape, the top pinch drive may touch only 2 mm strips on each side of the support tape leaving the middle 4 mm of the support tape untouched. Accordingly, the pinch drive roller does not interfere with or crush the tissue sections that are collected along the middle of the support tape.

While FIGS. 16A and 16B depict a collection apparatus 2100 absent one or more base portions and the microtome, FIG. 16C provides an illustration of collection apparatus 2100 disposed in a suitable coupling position with respect to the microtome. In operation, a support tape 2102 may be driven by bottom pinch drive 2130 to move from the support tape feed reel 2120 along rollers of the bottom pinch drive 2130, through a portion of a tension monitoring device 2140 and toward conveyor portion 2110. The support tape 2102 moves along a bottom surface of the conveyor portion 2110 and into a surface of fluid contained within the reservoir 2210. As the support tape 2102 moves around the tip of the conveyor portion and out of the fluid, the support tape 2102 collects thin tissue sections sliced from the microtome floating on the surface of the fluid. The support tape 2102 having thin tissue sections disposed thereon subsequently moves along a surface of the conveyor portion and toward applicator 2180 which applies cover tape 2104 to an upper surface of the support tape 2102. The support substrate combination 2106, having thin tissue sections disposed between support tape 2102 and cover tape 2104, then moves through top pinch drive 2132 and is collected into take up reel 2124. In some embodiments, when sectioning of a tissue sample by the microtome occurs, the above tissue section collecting process is automatically initiated on the collection apparatus.

In some embodiments, the support tape feed reel holder 2121, cover tape feed reel holder 2123 and take up reel holder 2125 incorporate a built in a slip clutch that engages with respective reels to maintain tape tension during operation of the collection apparatus. For example, a slip clutch may be built in to a reel holder so that a user is not required to adjust friction settings for proper engagement of a support or cover tape upon changing a corresponding reel. A slip clutch may also provide automatic compensation in tension for when the speed or geometry of the support substrate changes. In one embodiment, reel holders 2121, 2123, 2125 are, at appropriate times, driven in a reverse direction (e.g., with an electric motor) at a constant rate. Driving reel holders in a reverse direction, in combination with built-in slip clutches, may assist to ensure that the tape has a constant tension as the tape enters in and exits from the pinch drives. Such motion may avoid the occurrence of stick-slip of static friction.

As discussed above, the collection apparatus 2100 may optionally include a dual pinch drive configuration. In this respect, a bottom pinch drive 2130 may be disposed at a position upstream from take up of tissue sections before the support tape engages with the conveyor portion 2110 and the reservoir 2210. A top pinch drive 2132 may be disposed at a downstream position where tissue sections have already been collected on to the support tape. Pinch drives may be used to advance the support tape along the collection apparatus at a speed and tension suitable for automated collection of thin tissue sections for extended periods of time.

In some embodiments, the collection apparatus 2100 includes a tension monitoring device 2140 which provides feedback to a controller (e.g., computing device) regarding tension in the support tape. The controller, in turn, makes a determination as to whether settings in the top and/or bottom pinch drive should be adjusted to increase or decrease tension in the support tape. In an embodiment, tension monitoring device 2140 may include a spring-loaded dangler arm attached to a potentiometer to provide information about the tension in the support tape. Based on a desired tension for the support tape (e.g., to be maintained at a constant tension), actuation of pinch drives 2130, 2132 may be adjusted accordingly. For example, once presented with data from the potentiometer regarding the spring length of the dangler arm (i.e., the tension of the support tape), the controller makes a determination as to whether the spring length is within suitable operating conditions. If the spring length is outside of suitable operating conditions, the top or bottom pinch drive, or both, are adjusted to increase or decrease the support tape tension so as to maintain the spring length to be within operating conditions. In some cases, the tension of a support tape will be tightly controlled so as to minimize interference with the collection process, for example, arising from disturbances in the fluid of the reservoir.

In some embodiments, a feedback control mechanism is used to suitably maintain the rate of movement of the support tape on the collection apparatus. The speed of a support tape may be appropriately monitored, such as for example, by an optical encoder device (not expressly shown) that sends an electrical signal to the controller of the collection apparatus. Based on the speed of the support tape, the controller may send out a signal that results in actuation of components (e.g., a DC gear motor) of the top and/or bottom pinch drive. In some cases, the speed of a support tape is controlled to match the sectioning speed of the microtome, allowing for the collection process to be smooth and continuous.

The speed and tension of a support tape moving along a collection apparatus may be subject to a feedback mechanism (e.g., closed loop or open loop) controlled by a computing device using a suitable program (e.g., LabVIEW) that collects information regarding the speed and tension of the support tape through appropriate measuring techniques. In some embodiments, the speed and tension of the support tape during collection may be maintained at a user-specified range. For example, the speed and tension of the support tape may be kept by the controller system to be substantially constant. As discussed above, for some embodiments, pinch drives in feedback with the controller are appropriately actuated to maintain speed and/or tension of the support tape within suitable parameters. In some embodiments, reel holders are actuatable to drive a support tape along the collection apparatus, according to desired ranges of speed and/or tension.

Figure 17:
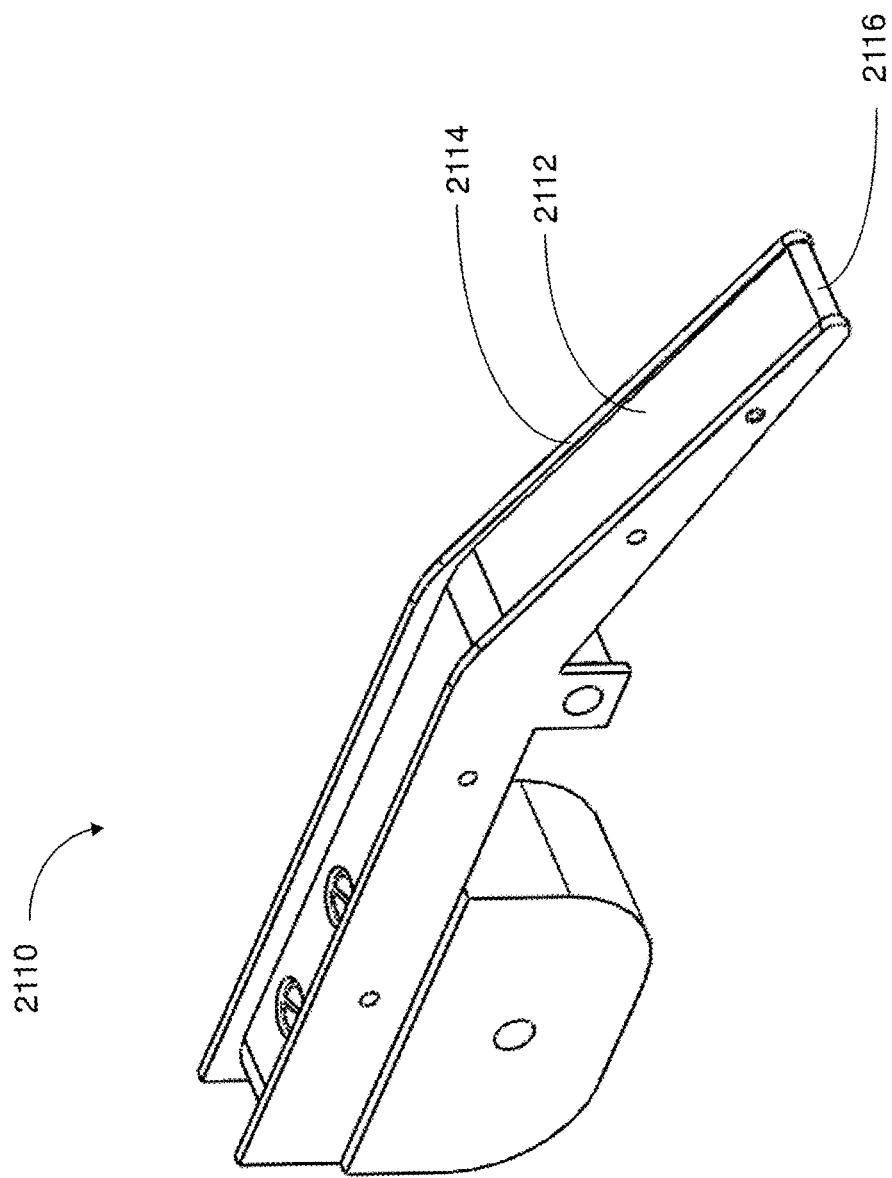
FIG. 17 is a perspective view of a conveyor portion of a collection apparatus in accordance with embodiments described.

A conveyor portion 2110 of a collection apparatus 2100 may be suitably constructed to facilitate automated collection of thin tissue sections on to a support substrate (e.g., support tape). FIG. 17 shows an embodiment of a conveyor portion 2110 that includes a collection surface 2112 upon which a support substrate may move along having collected a number of thin tissue sections. In some embodiments, the collection surface 2112 may be structured to have an inclination for guiding the support tape up from the fluid surface of the reservoir and into a subsequent portion of the collection apparatus for subsequent take up (e.g., application of cover tape and collection by a take up reel). In some cases, as shown in FIG. 17, collection surface 2112 additionally provides a relatively horizontal surface for the support tape to move along. The collection surface 2112 may provide a low-friction surface (e.g., Teflon, nylon) upon which a support tape may readily slide. The collection surface 2112 may have any suitable width, for example, between about 8 mm and about 10 mm wide, such as about 8.2 mm wide.

Side walls 2114 may act as barriers to the collection surface 2112 guiding the support substrate to maintain movement in a substantially straight direction along the conveyor. Side walls 2114 may include any suitable material, such as, and without limitation, stainless steel.

Conveyor tip 2116 may have a small radius of curvature, enabling the point of collection of thin tissue sections to be in close proximity to the edge of the knife. While for some instances, a conveyor tip 2116 may include a roller device, for other instances, a conveyor tip 2116 includes a rigid surface that is non-rotatable so as to minimize the collection of dirt on the conveyor and/or the occurrence of turbulence in the fluid through extraneous movement.

Figure 18:
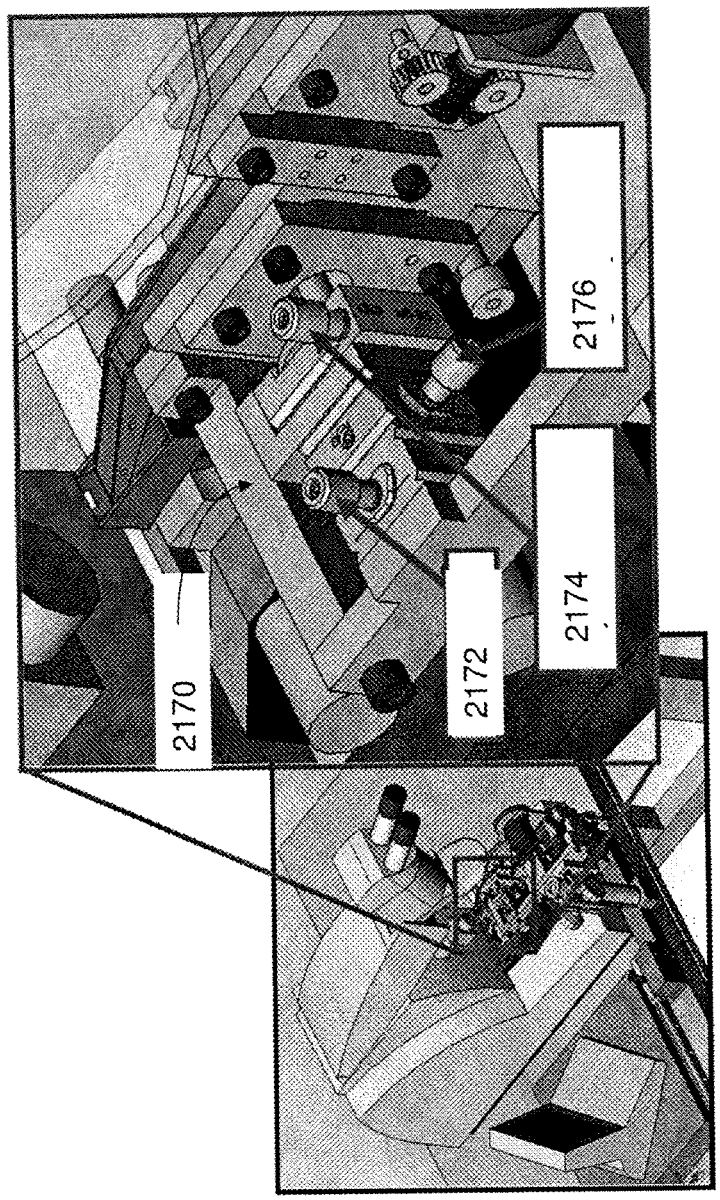
FIG. 18 is a perspective view of adjustment features of a collection apparatus in accordance with embodiments described.
Figure 19:
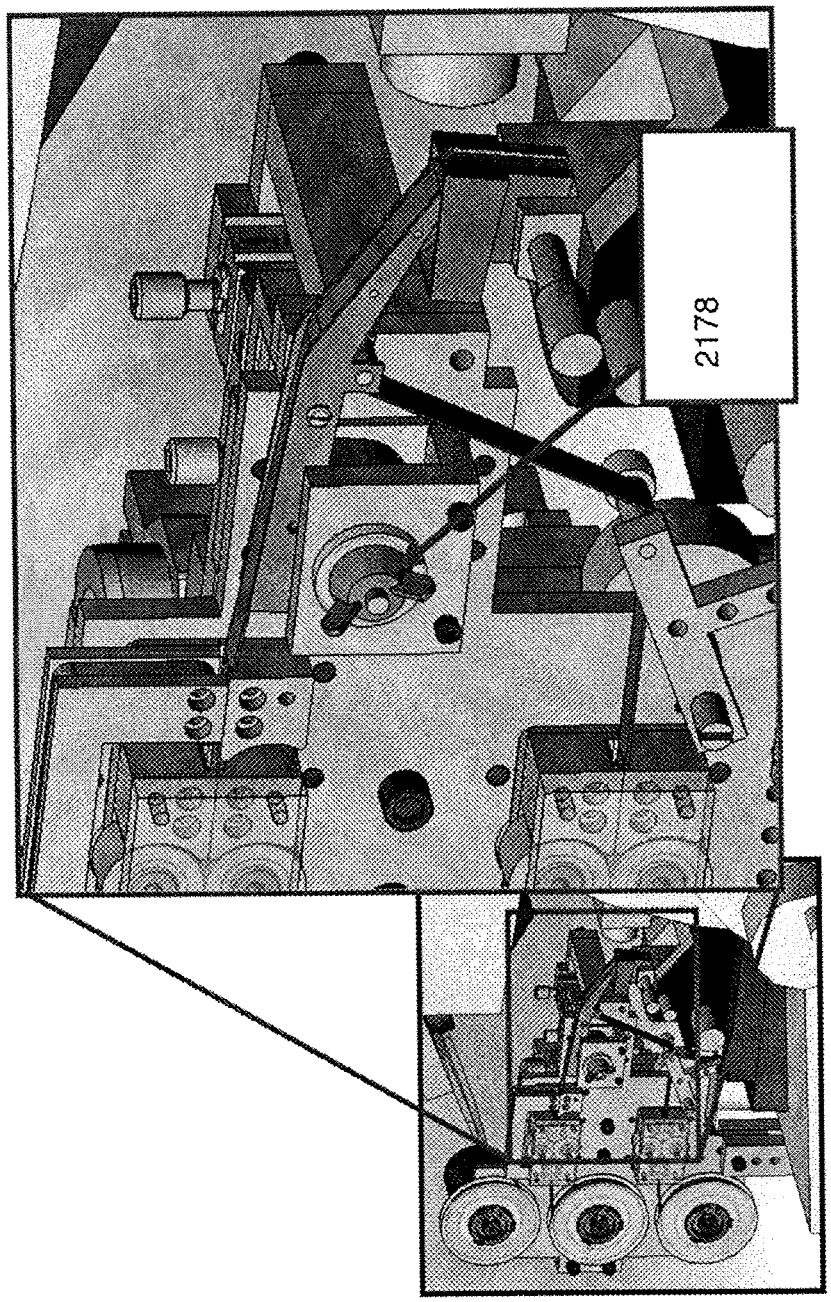
FIG. 19 is another perspective view of adjustment features of a collection apparatus in accordance with embodiments described.

The position of conveyor portion 2110 may be finely adjusted in any appropriate direction by any suitable manner. In some embodiments, a user may provide a fine adjustment of the height and/or the distance of the conveyor tip from the edge of the microtome knife and relative to the reservoir. Such fine adjustment may have a range, for example, over a distance of up to about 10 mm. An example shown in FIGS. 18 and 19 includes adjustment knobs 2170 that are conveniently accessible by a user for manipulating the position of conveyor portion 2110 with respect to the collection apparatus. As such, conveyor portion 2110 may be adjusted so that the conveyor tip 2116 is appropriately positioned with respect to the fluid in the reservoir 2210 and locked in place. In some cases, a height adjust knob 2172 may be used to manipulate the height of the conveyor portion 2110; an angle adjust knob 2174 may be suitable for changing the angle of orientation of the conveyor tip 2116 with respect to the fluid; and a forward-backward adjust knob 2176 may be employed for adjusting the distance of the conveyor portion 2110 relative to the microtome knife. When appropriate fine positional adjustments are made, the conveyor portion may be suitably locked in place, for example, with a tightening mechanism 2178 (e.g., wing nut), as shown in FIG. 19.

It should be appreciated for those of skill in the art that fine adjustments of the conveyor portion 2110 with respect to the collection apparatus 2100 may be automatic in nature. That is, a control system can determine what fine adjustments of the conveyor portion should be made for suitable positioning relative to the microtome knife. Accordingly, electrical signals may be sent to one or more actuators of the collection apparatus to provide for appropriate movement of the conveyor portion. Alternatively, a user can finely adjust the position of the conveyor portion relative to the collection apparatus without having to turn knobs, but by operating a control system that is suitably coupled with the collection apparatus.

In embodiments discussed, a collection apparatus may operate for over 12 hours; or days at a time. Accordingly, it may not be desirable for an operator to be required to observe the collection process over long periods of time. In some embodiments, video information of the collecting process may be suitably recorded to evaluate at what point there may have been lost or damaged tissue sections while the operator was away from the system. For example, a suitable video monitoring device may be used to verify correct operation of thin tissue sections as they come off of the knife edge and are collected. In an embodiment, the user interface of the fluid level control program described above includes a positionable box in the video images that records the light/dark contrast of each tissue section as it comes off the knife for collection. Video monitoring will make a record if a tissue section happens not to be sliced. Also, if a thin tissue section is too thin or thick, then the color of the section as recorded on the video image(s) will change, and be noted by the system. Monitoring collection of thin tissue sections by assessing the color of the sections is described in U.S. Patent Publication No. 2010/0093022 entitled "Methods and Apparatuses for Providing and Processing Sliced Thin Tissue."

Figure 20:
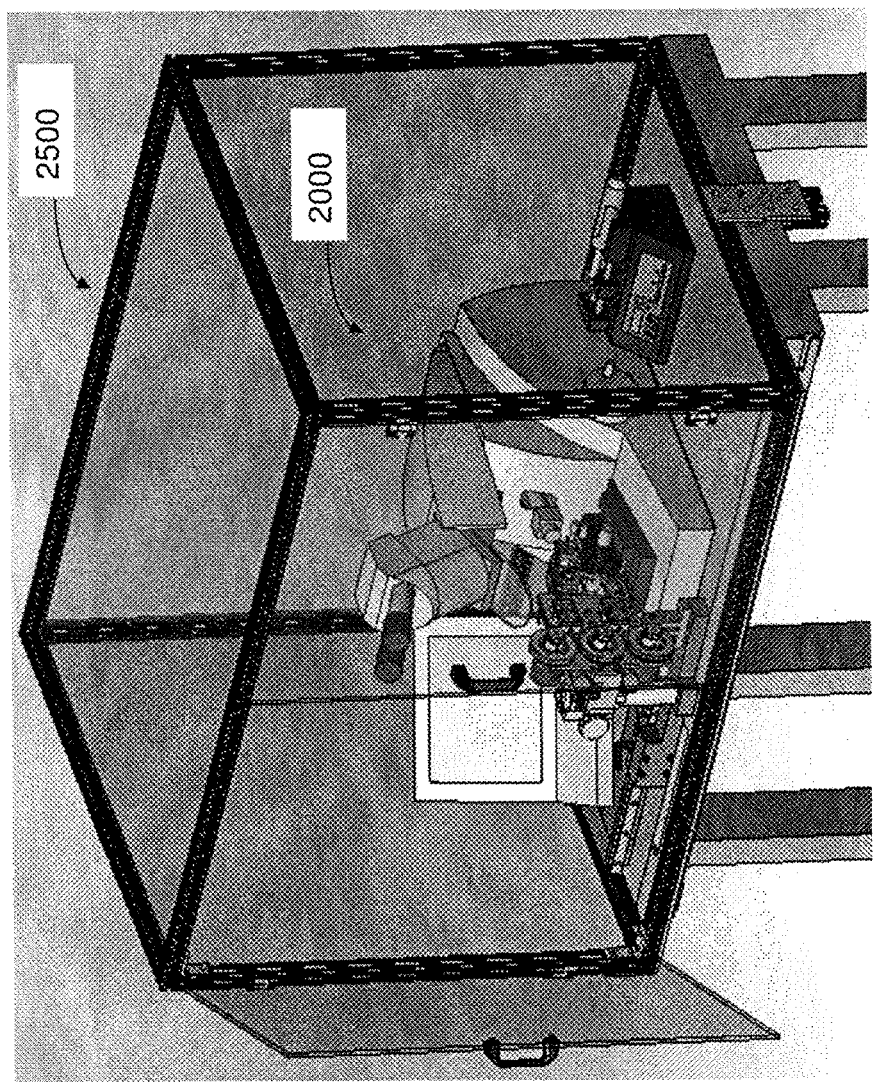
FIG. 20 is a perspective view of an enclosure for a system for processing tissue samples in accordance with embodiments described.

The system 2000 may be appropriately shielded from environmental disturbances, such as for example, air drafts or abrupt changes in temperature. In some embodiments, the system 2000 may be surrounded by an environmental enclosure 2500, such as that shown in FIG. 20, so that undesirable environmental occurrences do not detrimentally interfere with operation of the collection process. The environmental enclosure 2500 may, without limitation, be suitable a plexi-glass case, or other appropriate device.

IV. Conclusion

Having thus described various illustrative embodiments, it is to be appreciated that various alterations, modifications, and improvements will readily occur to those skilled in the art. Such alterations, modifications, and improvements are intended to be part of this invention, and are intended to be within the spirit and scope of this invention. While some examples presented herein involve specific combinations of functions or structural elements, it should be understood that those functions and elements may be combined in other ways according to the present invention to accomplish the same or different objectives. In particular, acts, elements, and features discussed in connection with one embodiment are not intended to be excluded from similar or other roles in other embodiments. Accordingly, the foregoing description and attached drawings are by way of example only, and are not intended to be limiting.

Any suitable embodiments described as well as implied herein can be implemented in any of numerous ways. For example, the embodiments may be implemented using hardware, software or a combination thereof. When implemented in software, the software code can be executed on any suitable processor or collection of processors, whether provided in a single computer or distributed among multiple computers.

Further, it should be appreciated that a computing device may be embodied in any of a number of forms, such as a rack-mounted computer, a desktop computer, a laptop computer, or a tablet computer. Additionally, a computing device may be embedded in a device not generally regarded as a computer but with suitable processing capabilities, including a Personal Digital Assistant (PDA), a smart phone or any other suitable portable or fixed electronic device.

Also, the computing device may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computing device may receive input information through speech recognition or in other audible format.

Also, the various methods or processes outlined herein may be coded as software that is executable on one or more processors that employ any one of a variety of operating systems or platforms. Additionally, such software may be written using any of a number of suitable programming languages and/or conventional programming or scripting tools, and also may be compiled as executable machine language code or intermediate code that is executed on a framework or virtual machine.

In this respect, embodiments may include a computer readable medium (or multiple computer readable media) (e.g., a computer memory, one or more floppy discs, compact discs, optical discs, magnetic tapes, flash memories, circuit configurations in Field Programmable Gate Arrays or other semiconductor devices, or other non-transitory medium or tangible computer storage medium, etc.) encoded with one or more programs that, when executed on one or more computing devices, computers, or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

The terms "program" or "software" are used herein in a generic sense to refer to any type of computer code or set of computer-executable instructions that can be employed to program a computing device, computer or other processor to implement various aspects of the present invention as discussed above. Additionally, it should be appreciated that according to one aspect of this embodiment, one or more computer programs that when executed perform methods of the present invention need not reside on a single computing device, computer or processor, but may be distributed in a modular fashion amongst a number of different computing devices, computers or processors to implement various aspects of the present invention.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Also, data structures may be stored in computer-readable media in any suitable form. For simplicity of illustration, data structures may be shown to have fields that are related through location in the data structure. Such relationships may likewise be achieved by assigning storage for the fields with locations in a computer-readable medium that conveys relationship between the fields. However, any suitable mechanism may be used to establish a relationship between information in fields of a data structure, including through the use of pointers, tags or other mechanisms that establish relationship between data elements.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Also, the invention may be embodied as a method, of which an example has been provided. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

The invention claimed is:

1. A system for processing a tissue sample, the system comprising:
    a microtome having a reservoir containing fluid automatically maintained at a substantially constant level within the reservoir, the microtome adapted to slice at least one thin tissue section from a tissue sample such that the at least one thin tissue section contacts the fluid within the reservoir;
    a collection apparatus for collecting the at least one thin tissue section from the fluid within the reservoir; and
    a video apparatus for monitoring video information to indicate a current level of the fluid contained within the reservoir.

2. The system of claim 1, wherein the microtome and the collection apparatus are physically coupled through the fluid within the reservoir.

3. The system of claim 1, wherein a surface of the fluid is in intermittent contact with a knife edge of the microtome.

4. The system of claim 1, wherein the fluid forms a meniscus with a knife edge of the microtome.

5. The system of claim 1, wherein the video information includes information regarding a reflection of light from a surface of the fluid.

6. The system of claim 5, wherein the video information comprises a light colored reflection of light from the surface of the fluid to indicate a presence of a substantially flat fluid surface.

7. The system of claim 5, wherein the video information comprises a dark colored reflection of light from the surface of the fluid to indicate a presence of a meniscus.

8. The system of claim 1, further comprising a fluid input apparatus coupled to the reservoir for inputting fluid into the reservoir.

9. A method for using a microtome including slicing a tissue sample with a microtome-quality knife to produce at least one thin tissue section, and bringing the at least one thin tissue section into contact with a fluid within the reservoir of the microtome, the method comprising:
    monitoring a current level of fluid within the reservoir with respect to an edge of the microtome-quality knife by monitoring video information to indicate the current level of fluid within the reservoir with respect to the edge of the microtome-quality knife; and
    automatically restoring the current level of fluid within the reservoir to an operating level of fluid when the current level of fluid within the reservoir is less than the operating level of fluid.

10. The method of claim 9, wherein a surface of the fluid is in intermittent contact with the edge of the microtome-quality knife.

11. The method of claim 9, wherein the operating level of fluid comprises formation of a meniscus with the edge of the microtome-quality knife to wet the edge of the microtome-quality knife when slicing the tissue sample to produce the at least one thin tissue section.

12. The method of claim 9, wherein monitoring the video information includes monitoring information regarding a reflection of light from a surface of the fluid.

13. The method of claim 12, wherein monitoring the information regarding the reflection of light from the surface of the fluid comprises monitoring a light colored reflection of light from the surface of the fluid to indicate a presence of a flat fluid surface and monitoring a dark colored reflection of light from the surface of the fluid to indicate a presence of a meniscus.

14. The method of claim 9, wherein the current level of fluid within the reservoir is determined based on a distance from a meniscus that wets the edge of the microtome-quality knife to the edge of the microtome-quality knife.

15. The method of claim 9, wherein automatically restoring the current level of fluid within the reservoir to the operating level of fluid comprises pumping additional fluid into the reservoir.

* * * * *